(12) United States Patent
Nishide et al.

(10) Patent No.: US 7,756,240 B2
(45) Date of Patent: Jul. 13, 2010

(54) X-RAY COMPUTED TOMOGRAPHY APPARATUS

(75) Inventors: Akihiko Nishide, Tokyo (JP); Makoto Gohno, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 241 days.

(21) Appl. No.: 11/956,813

(22) Filed: Dec. 14, 2007

(65) Prior Publication Data

US 2008/0144764 A1 Jun. 19, 2008

(30) Foreign Application Priority Data

Dec. 18, 2006 (JP) .............................. 2006-339313

(51) Int. Cl.
*A61B 6/00* (2006.01)
(52) U.S. Cl. ........................................ 378/5; 378/98.11
(58) Field of Classification Search .................... 378/5, 378/98.11, 98.12
See application file for complete search history.

(56) References Cited

U.S. PATENT DOCUMENTS

| 4,463,375 | A | * | 7/1984 | Macovski ................ 378/98.12 |
| 6,018,565 | A | * | 1/2000 | Ergun et al. .................... 378/95 |
| 6,661,873 | B2 | | 12/2003 | Jabri et al. |
| 6,816,572 | B2 | | 11/2004 | Jabri et al. |
| 7,272,429 | B2 | | 9/2007 | Walker et al. |
| 7,280,635 | B2 | * | 10/2007 | Toth ............................ 378/108 |
| 2002/0075997 | A1 | * | 6/2002 | Unger et al. ................ 378/98.9 |
| 2003/0142787 | A1 | * | 7/2003 | Jabri et al. ................ 378/98.12 |
| 2004/0066881 | A1 | * | 4/2004 | Reddy et al. .................... 378/5 |
| 2004/0234031 | A1 | * | 11/2004 | Francke et al. .................. 378/98 |
| 2005/0008115 | A1 | * | 1/2005 | Tsukagoshi .................... 378/4 |
| 2006/0109949 | A1 | * | 5/2006 | Tkaczyk et al. ................ 378/4 |
| 2006/0280281 | A1 | * | 12/2006 | Flohr et al. .................... 378/5 |
| 2009/0180585 | A1 | * | 7/2009 | Fujimoto et al. ............... 378/5 |

FOREIGN PATENT DOCUMENTS

JP 2003-244542 8/2003

* cited by examiner

*Primary Examiner*—Edward J Glick
*Assistant Examiner*—Alexander H Taningco
(74) *Attorney, Agent, or Firm*—Armstrong Teasdale LLP

(57) ABSTRACT

The present invention provides an X-ray CT apparatus capable of improving image quality of a dual energy image. The X-ray CT apparatus comprises an X-ray tube for applying X rays having a first energy spectrum and X rays having a second energy spectrum different from the first energy spectrum to a subject, an X-ray data acquisition unit for acquiring X-ray projection data of the first energy spectrum projected onto the subject and X-ray projection data of the second energy spectrum projected thereonto, dual energy image reconstructing unit for image-reconstructing tomographic images indicative of X-ray tube voltage-dependent information at X-ray absorption coefficients related to a distribution of atoms, based on the X-ray projection data of the first energy spectrum and the X-ray projection data of the second energy spectrum, and adjusting unit for adjusting conditions for the image reconstruction in order to optimize the tomographic images indicative of the X-ray tube voltage-dependent information.

19 Claims, 24 Drawing Sheets

(a)

(b)

STANDARD DEVIATION sd (UNIT: HU)
OF TOMOGRAPHIC IMAGE
SUBJECTED TO DUAL ENERGY SCAN

STANDARD DEVIATION sd (UNIT: HU)
OF TOMOGRAPHIC IMAGE
SUBJECTED TO DUAL ENERGY SCAN

TWO-DIMENSIONAL CORRELATION COMPUTATION (a)

(b)

(a)

(b)

(a)

(b)

X-RAY COMPUTED TOMOGRAPHY APPARATUS

CROSS REFERENCE TO RELATED APPLICATIONS

This application claims the benefit of Japanese Patent Application No. 2006-339313 filed Dec. 18, 2006.

BACKGROUND OF THE INVENTION

The present invention relates to techniques of an X-ray CT apparatus which optimizes spatial resolution and image noise of two-dimensional distribution tomographic images indicative of X-ray tube voltage-dependent information at X-ray absorption coefficients related to a distribution of atoms, tomographic images subjected to a so-called dual energy scan in a medical X-ray CT (Computed Tomography) apparatus or the like, and of an X-ray CT image reconstructing method used therefor.

In an X-ray CT apparatus using a two-dimensional X-ray area detector, tomogram imaging based on a low X-ray tube voltage and a high X-ray tube voltage has heretofore been performed upon obtaining tomographic images of a two-dimensional distribution of given atoms as shown in FIG. 4 to thereby obtain a tomographic image at the low X-ray tube voltage and a tomographic image at the high X-ray tube voltage. Then, the tomographic image at the low X-ray tube voltage and the tomographic image at the high X-ray tube voltage are subjected to a weight adding process in accordance with weighted addition coefficients prescribed or defined every atom for the two-dimensional distribution desired to see, whereby a two-dimensional distribution indicative of X-ray tube voltage-dependent information at X-ray absorption coefficients related to the distribution of the given atoms, tomographic images subjected to a so-called dual energy scan were obtained. As shown in FIG. 5, a low X-ray tube voltage and a high X-ray tube voltage are applied to obtain X-ray projection data of the low X-ray tube voltage and X-ray projection data of the high X-ray tube voltage. Then, the X-ray projection data of the low X-ray tube voltage and the X-ray projection data of the high X-ray tube voltage are subjected to a weight adding process in accordance with the weighted addition coefficients defined every atom to obtain tomographic images subjected to the so-called dual energy scan or imaging.

However, even in the case of the weight adding process for the tomographic images in FIG. 4 and the weight adding process for the X-ray projection data in FIG. 5, one of the weighted addition coefficients is a minus number. Therefore, image noise of the tomographic images subjected to the so-called dual energy scan, corresponding to the tomographic images indicative of the X-ray tube voltage-dependent information tend to become worse than image noise of the tomographic image at the original low X-ray tube voltage and image noise of the tomographic image at the high X-ray tube voltage. Therefore, it was difficult to ensure image quality of the final tomographic image subjected to the dual energy scan, i.e., ensure spatial resolution and image noise. Therefore, when the application of X rays is increased to improve the image quality, X-ray exposure increases. A problem arises in that when the dose of X rays is decreased in revere, the image quality falls short.

Patent Document 1. Japanese Unexamined Patent Publication No. 2003-244542.

SUMMARY OF THE INVENTION

However, the X-ray CT apparatus using the two-dimensional X-ray area detector has a tendency to need a new added value like a so-called dual energy scan in addition to the conventional imaging or scanning method for bringing the distribution of X-ray absorption coefficients by one X-ray tube voltage to each tomographic image as a two-dimensional distribution of CT values. Thus, tomographic images based on a high image-quality dual energy scan have also been expected.

Thus, an object of the present invention is to provide an X-ray CT apparatus that optimizes spatial resolution or image noise of two-dimensional distribution tomographic images indicative of X-ray tube voltage-dependent information at X-ray absorption coefficients related to a distribution of atoms, i.e., tomographic images subjected to a so-called dual energy scan.

In the present invention, imaging conditions are adjusted within the limits of imaging conditions for respective X-ray tube voltages in such a manner that upon photography of two-dimensional distribution tomographic images indicative of X-ray tube voltage-dependent information, i.e., a dual energy tomographic-image scan, the image quality of tomographic images at a low X-ray tube voltage and a high X-ray tube voltage are not degraded, i.e., they are brought to approximately the same image quality or image noise. Under the respective X-ray imaging conditions at this time, imaging conditions other than X-ray tube voltages and X-ray tube currents may differ. The imaging conditions under which the tomographic images of approximately the same image quality or image noise can be obtained at the respective X-ray tube voltages, can be set.

In FIG. 10 shown as one example, the image quality of once-photographed or scanned tomographic images indicative of X-ray tube voltage-dependent information, i.e., tomographic images subjected to a so-called energy scan are fed back to image reconstructing conditions for tomographic images at respective X-ray tube voltages in such a way as to satisfy at least one index value for image quality, of a noise index value, a spatial resolution index value and a slice thickness index value. Optimizing the image reconstructing conditions at the low and high X-ray tube voltages and executing image reconstruction again makes it possible to adjust the image quality of the tomographic images indicative of the X-ray tube voltage-dependent information, i.e., the tomographic images subjected to the so-called dual energy scan in such a way as to meet at least one index value for image quality, of the noise index value, spatial resolution index value and slice thickness index value.

An X-ray CT apparatus according to a first aspect comprises an X-ray tube for applying, to a subject, X rays having a first energy spectrum and X rays having a second energy spectrum different from the first energy spectrum, an X-ray data acquisition unit for acquiring X-ray projection data of the first energy spectrum applied to the subject and X-ray projection data of the second energy spectrum applied thereto, dual energy image reconstructing unit for image-reconstructing tomographic images indicative of X-ray tube voltage-dependent information at X-ray absorption coefficients related to a distribution of atoms, based on the X-ray projection data of the first energy spectrum and the X-ray projection data of the second energy spectrum; and adjusting unit for adjusting conditions for the image reconstruction to optimize the tomographic images indicative of the X-ray tube voltage-dependent information.

In the X-ray Ct apparatus according to the first aspect, the tomographic images indicative of the X-ray tube voltage-dependent information are determined by computations from the X-ray projection data of the first energy spectrum and the X-ray projection data of the second energy spectrum. If the tomographic images indicative of the X-ray tube voltage-information are not optimum, then the adjusting unit effects feedback to adjust the image reconstructing conditions for the X-ray projection data of the first and second energy spectrums. It is thus possible to optimize the image quality of each of the tomographic images indicative of the X-ray tube voltage-dependent information.

In a second aspect, the dual energy image reconstructing unit image-reconstructs a first tomographic image and a second tomographic image, based on the X-ray projection data of the first energy spectrum and the X-ray projection data of the second energy spectrum, and image-reconstructs the tomographic images indicative of the X-ray voltage-dependent information at the X-ray absorption coefficients related to the distribution of the atoms, based on the first tomographic image and the second tomographic image. And said adjusting unit adjusts image reconstructing conditions for the first and second tomographic images respectively to optimize the tomographic images indicative of the X-ray tube voltage-dependent information.

In the X-ray CT apparatus according to the second aspect, the tomographic images indicative of the X-ray tube voltage-dependent information are determined by computations from the first and second tomographic images. If the tomographic images indicative of the X-ray tube voltage-dependent information are not optimum, then the adjusting unit performs feedback to adjust the conditions for image-reconstructing the first tomographic image from the X-ray projection data of the first energy spectrum and the second tomographic image from the X-ray projection data of the second energy spectrum respectively. Thus, the image quality of each of the tomographic images indicative of the X-ray tube voltage-dependent information can be optimized.

The X-ray CT apparatus according to a third aspect is provided wherein in the second aspect, the adjusting unit adjusts imaging conditions at the application of the X rays having the first energy spectrum and the X rays having the second energy spectrum in order to optimize the tomographic images indicative of the X-ray tube voltage-dependent information.

In order to optimize the image quality of each of the tomographic images indicative of the X-ray tube voltage-dependent information, X rays can be applied in accordance with imaging conditions in which conditions for voltages or currents of the X-ray tube are adjusted, as well as the imaging conditions for image reconstruction.

The X-ray CT apparatus according to a fourth aspect adjusts image reconstructing conditions while being allowed to depend upon index values for image quality of the tomographic images indicative of the X-ray tube voltage-dependent information by the dual energy image reconstructing unit.

In the X-ray CT apparatus according to the fourth aspect, the tomographic images indicative of the X-ray tube voltage-dependent information are image-reconstructed once and the image reconstructing conditions are adjusted depending on the index values for image quality. When each of the index values for image quality is different from an optimized target value, the difference therebetween is fed back to adjust the image-reconstructing condition that becomes an image-reconstructed source, within a settable range, thereby performing image reconstruction again. Thus, the final image quality of each of the tomographic images indicative of the X-ray tube voltage-dependent information can be adjusted so as to reach a target value.

The X-ray CT apparatus according to a fifth aspect is provided wherein the X-ray tube applies the X rays having the first energy spectrum and the X rays having the second energy spectrum to the same region of the subject.

In the X-ray CT apparatus according to the fifth aspect, computational processing is performed between tomographic images or X-ray projection data based on the X rays having the first energy spectrum and the X rays having the second energy spectrum both applied to the same region of the subject, using the tomographic images or X-ray projection data upon the photography of the tomographic images indicative of the X-ray tube voltage information. The tomographic images indicative of the X-ray tube voltage-dependent information at the same region of the subject can be obtained by quickly switching between the rays having the first energy spectrum and the X rays having the second energy spectrum.

The X-ray CT apparatus according to a sixth aspect is provided wherein in the first or third aspect, the dual energy image reconstructing unit image-reconstructs X-ray projection data obtained by multiplying the X-ray projection data of the first energy spectrum by a first weighted coefficient, multiplying the X-ray projection data of the second energy spectrum by a second weighted coefficient corresponding to a minus number, and subjecting them to a weight adding process.

In the X-ray CT apparatus according to the sixth aspect, as one method for performing the image reconstruction of each of the tomographic images indicative of the X-ray tube voltage-dependent information, there is known a method of determining the X-ray projection data of the first energy spectrum and the X-ray projection data of the second energy spectrum by a weight adding process. When, in this case, an atom or region desired to be eliminated, i.e., an atom or region at which it is desired to bring a pixel value on each tomographic image to 0, is defined or prescribed, weighted coefficients therefor are determined. Executing the weight adding process using the weighted coefficients makes it possible to bring the pixel value of the atom or region to 0. Upon discrimination between, for example, a contrast agent close to a calcium component in CT value and the calcium component such as bones, the calcium component is left when iodine is eliminated, and iodine is left when the calcium component is eliminated. The element that one desires to see, can be brought into imaging by doing so.

The X-ray CT apparatus according to a seventh aspect is provided wherein in the second aspect, the dual energy image reconstructing unit multiplies the first tomographic image by a first weighted coefficient, multiplies the second tomographic image by a second weighted coefficient corresponding to a minus number and subjects the so-processed tomographic images to a weight adding process.

In the X-ray CT apparatus according to the seventh aspect, as one method of performing image reconstruction of each of the tomographic images indicative of the X-ray tube voltage-dependent information, there is known a method of determining the first and second tomographic images by a weight adding process. The tomographic images indicative of the X-ray tube voltage-dependent information are determined from the weight-added tomographic images. Since the first and second tomographic images are subjected to subtraction and thereby a signal component is reduced, image noise increases relatively. In this case, degradation of image noise of each of the tomographic images indicative of the X-ray tube voltage-dependent information becomes a problem. When the image quality is deteriorated in this way, it is necessary to improve the image quality every tomographic images at plural X-ray tube voltages such as described in the present embodiment.

The X-ray CT apparatus according to an eighth aspect is provided wherein the image reconstruction has at least one of an image reconstruction function, an image filter, an image reconstruction matrix number, a z filter, and a space filter for an X-ray projection data space.

The X-ray CT apparatus according to the eighth aspect needs an improvement in the image quality of each of the tomographic images indicative of the X-ray tube voltage-dependent information and an improvement in the image noise. Therefore, as ones for the image reconstruction, there are known approaches or techniques such as making the image reconstruction function as one reduced in image noise, making the image filter as one having an image noise reducing effect, a reduction in image reconstruction matrix number, expanding the z filter in a z direction to reduce image noise, making the space filter for the X-ray projection data space as one having an image noise reducing characteristic, etc. It is thus possible to perform an improvement in image quality of each of the tomographic images indicative of the X-ray tube voltage-dependent information and an improvement in image noise.

The X-ray CT apparatus according to a ninth aspect relates to the fifth aspect. The index values for the image quality have at least one of a noise index value, a spatial resolution index value or a slice thickness index value.

In the X-ray CT apparatus according to the ninth aspect, the minimum image quality is required to make a diagnosis with the tomographic images indicative of the X-ray tube voltage-dependent information. Therefore, as a target value for image quality, at least one of the noise index value, the spatial resolution index value and the slice thickness index value is set to manage the image quality.

In a tenth aspect, noise of the X-ray projection data of the first energy spectrum and noise of the X-ray projection data of the second energy spectrum are made approximately equal to each other, or made approximately equal to each other when weighted addition coefficients are multiplied.

In the X-ray CT apparatus according to the tenth aspect, in order to improve the image quality of each of the tomographic image indicative of the X-ray tube voltage-dependent information, the noise of the X-ray projection data of the first energy spectrum and the noise of the X-ray projection data of the second energy spectrum may be made approximately equal to each other or made approximately equal to each other when the weighted addition coefficients are multiplied. Therefore, the imaging or scanning conditions and image reconstructing conditions may be set in this way.

An eleventh aspect relates to the second aspect. Image noise of the first tomographic image and image noise of the second tomographic image are made approximately equal to each other, or made approximately equal to each other when weighted addition coefficients are multiplied.

In the X-ray CT apparatus according to the eleventh aspect, in order to improve the image quality of each of the tomographic images indicative of the X-ray tube voltage-dependent information, the image noise of the first tomographic image and the image noise of the second tomographic image may be made approximately equal to each other or made approximately equal to each other when the weighted addition coefficients are multiplied.

In the X-ray CT apparatus according to a twelfth aspect, when mis-registration artifacts are found at the tomographic images indicative of the X-ray tube voltage-dependent information, the first tomographic image and the second tomographic image are registered with each other and image-reconstructed again.

In the X-ray CT apparatus according to the twelfth aspect, when the tomographic images at the plural X-ray tube voltages cause mis-registration within a tomographic image plane, i.e., in an xy plane direction, mis-registration artifacts occur in the tomographic images indicative of the X-ray tube voltage-dependent information. In general, the mis-registration artifacts occur in the direction in which the profiles of respective regions for the tomographic images indicative of the X-ray tube voltage-dependent information are white or black, that is, the pixel values become excessively large or small. That is, the mis-registration artifacts appear as white or black profile lines or some of the profile lines along the profile lines of the respective regions. In such a case, the positions of the tomographic image at the low X-ray tube voltage and the tomographic image at the high X-ray tube voltage are subjected to a mis-registration correction so as to be in proper registration. That is, the mis-registration correction is carried out by executing a mis-registration correction based on coordinate transformation or a scaling magnification correction, whereby the mis-registration artifacts like the white or black profile lines, of the tomographic images indicative of the X-ray tube voltage-dependent information can be eliminated.

In a thirteenth aspect, when mis-registration occurs in a tomographic image plane when a display in the direction of a body axis of the subject or a three-dimensional display is effected on the tomographic images indicative of the X-ray tube voltage-dependent information, the first tomographic image and the second tomographic image are aligned with each other and image-reconstructed again.

In the X-ray CT apparatus according to the thirteenth aspect, when a conventional scan or a cine scan is effected on the tomographic images indicative of the X-ray tube voltage-dependent information at a plurality of z-direction coordinate positions of the subject, the tomographic images at the plural z-direction coordinate positions are shifted or displaced within a tomographic image plane, i.e., an xy plane due to respiration, beat or the like of the subject. When the tomographic images indicative of the X-ray tube voltage-dependent information are three-dimensionally displayed or MPR (Multi Plain Reformat)-displayed, splicing for a z-direction conventional (axial scan) or cine scan might be viewed. That is, since the tomographic images at the original plural X-ray tube voltages are shifted in the x or y direction upon photography at the plural z-direction coordinate positions, the slicing appears as slicing artifacts. In order to eliminate the slicing artifacts, the conventional scan or cine scan at each z-direction coordinate position is performed to correct mis-registration as viewed in x or y direction and the image reconstruction is carried out again. Consequently, the slicing artifacts can be eliminated. Thus, it is possible to optimize a three-dimensionally-displayed image for each tomographic image indicative of the X-ray tube voltage-dependent information or an MPR-displayed image therefor.

According to the X-ray CT apparatus of the present invention, an advantageous effect is brought about in that an X-ray CT apparatus which optimizes spatial resolution or image noise of tomographic images indicative of X-ray tube voltage-dependent information at X-ray absorption coefficients related to a distribution of atoms at a conventional scan, a helical scan, a cine scan, a variable pitch helical scan or a helical shuttle scan or the like can be realized.

DETAILED DESCRIPTION OF THE INVENTION

Overall Construction of X-Ray CT Apparatus.

Figure 1:
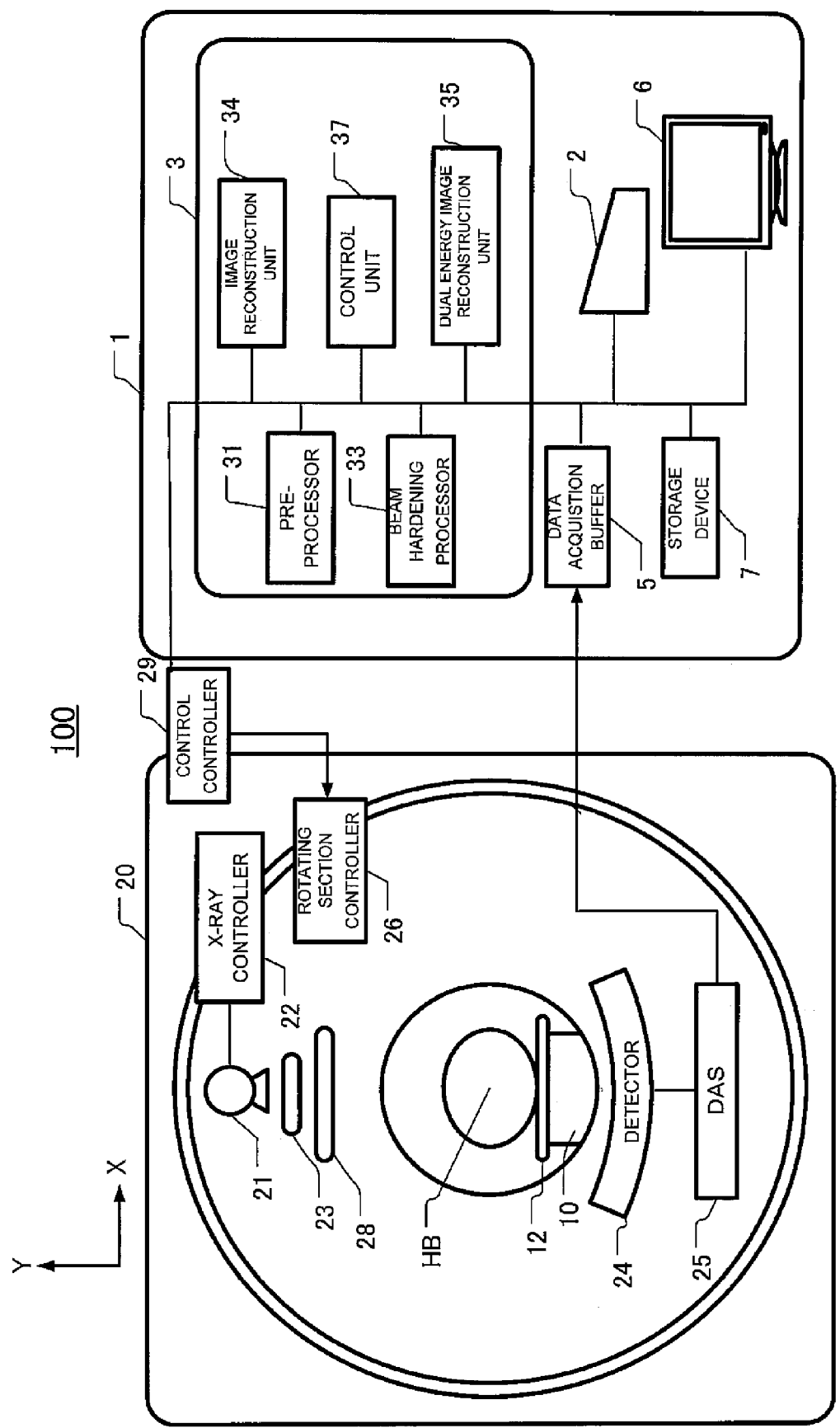
FIG. 1 is a block diagram showing an X-ray CT apparatus 100 according to an embodiment of the present invention.

FIG. 1 is a configuration block diagram showing an X-ray CT apparatus 100 according to one embodiment of the present invention. The X-ray CT apparatus 100 is equipped with an operation console 1, an imaging or photographing table 10 and a scan gantry 20.

The operation console 1 includes an input device 2 such as a keyboard or a mouse, which accepts an input from an operator, a central processing unit 3 which executes a pre-process, an image reconstructing process, a post-process, etc., and a data acquisition buffer 5 which acquires or collects X-ray detector data acquired by the scan gantry 20. Further, the operation console 1 is equipped with a monitor 6 which displays a tomographic image image-reconstructed from projection data obtained by pre-processing the X-ray detector data, and a storage device 7 which stores programs, X-ray detector data, projection data and X-ray tomographic images therein. An input for imaging or photographing conditions is inputted from the input device 2 and stored in the storage device 7. The photographing table 10 includes a cradle 12 that draws and inserts a subject from and into a bore or aperture of the scan gantry 20 with the subject placed thereon. The cradle 12 is elevated and moved linearly on the photographing table 10 by a motor built in the photographing table 10.

The scan gantry 20 includes an X-ray tube 21, an X-ray controller 22, a collimator 23, a beam forming X-ray filter 28, a multi-row X-ray detector 24, and a data acquisition system (DAS) 25. Further, the scan gantry 20 includes a rotating section controller 26 which controls the X-ray tube 21 or the like rotated about a body axis of the subject, and a control controller 29 which swaps control signals or the like with the operation console 1 and the photographing table 10. The beam forming X-ray filter 28 is an X-ray filter configured so as to be thinnest in thickness as viewed in the direction of X rays directed to the center of rotation corresponding to the center of imaging, to increase in thickness toward its peripheral portion and to be able to further absorb the X rays. Therefore, the body surface of the subject whose sectional shape is nearly circular or elliptic can be less exposed to radiation.

The central processing unit 3 has a pre-processor 31, a beam hardening processor 33, an image reconstruction unit 34, a dual energy image reconstruction unit 35 and an adjustment or control unit 37.

The pre-processor 31 executes a pre-process such as an X-ray dose correction for correcting ununiformity of sensitivity between channels and correcting an extreme reduction in signal intensity or a signal omission due to an X-ray strong absorber, principally, a metal portion on raw data acquired by the data acquisition system 25.

The beam hardening processor 33 correct-processes beam hardening of projection data. The beam hardening is of a phenomenon in which X-ray absorption changes according to a penetration thickness even in the case of the same quality of material and a CT value (brightness or luminance) on a CT image changes. Particularly, it unit that an energy distribution of radiation transmitted through the subject deviates to the high-energy side. Therefore, beam hardening is corrected with respect to a slice direction and a channel direction for projection data.

The image reconstruction unit 34 receives projection data pre-processed by the pre-processor 31 and reconstructs each image, based on the projection data. The projection data is subjected to fast Fourier transform (FFT) for performing transformation into a frequency domain or region and convolved with a reconstruction function Kernel (j), followed by being subjected to inverse Fourier transform. The image reconstruction unit 34 performs a three-dimensional back-projecting process on the projection data obtained by subjecting the reconstruction function Kernel (j) to a convolution process to determine each tomographic image (xy plane) every body-axis direction (Z direction) of a subject HB. The image reconstruction unit 34 stores the tomographic image in the storage device 7.

The dual energy image reconstruction unit 35 reconstructs two-dimensional distribution tomographic images indicative of X-ray tube voltage-dependent information related to an atom's distribution, i.e., tomographic images subjected to a so-called dual energy scan or photography from the projection data or tomographic images.

The control unit 37 adjusts conditions for image reconstruction to optimize each tomographic image subjected to the dual energy scan, or adjusts imaging or photographic conditions.

Operation Flowchart of X-Ray CT Apparatus.

Figure 2:
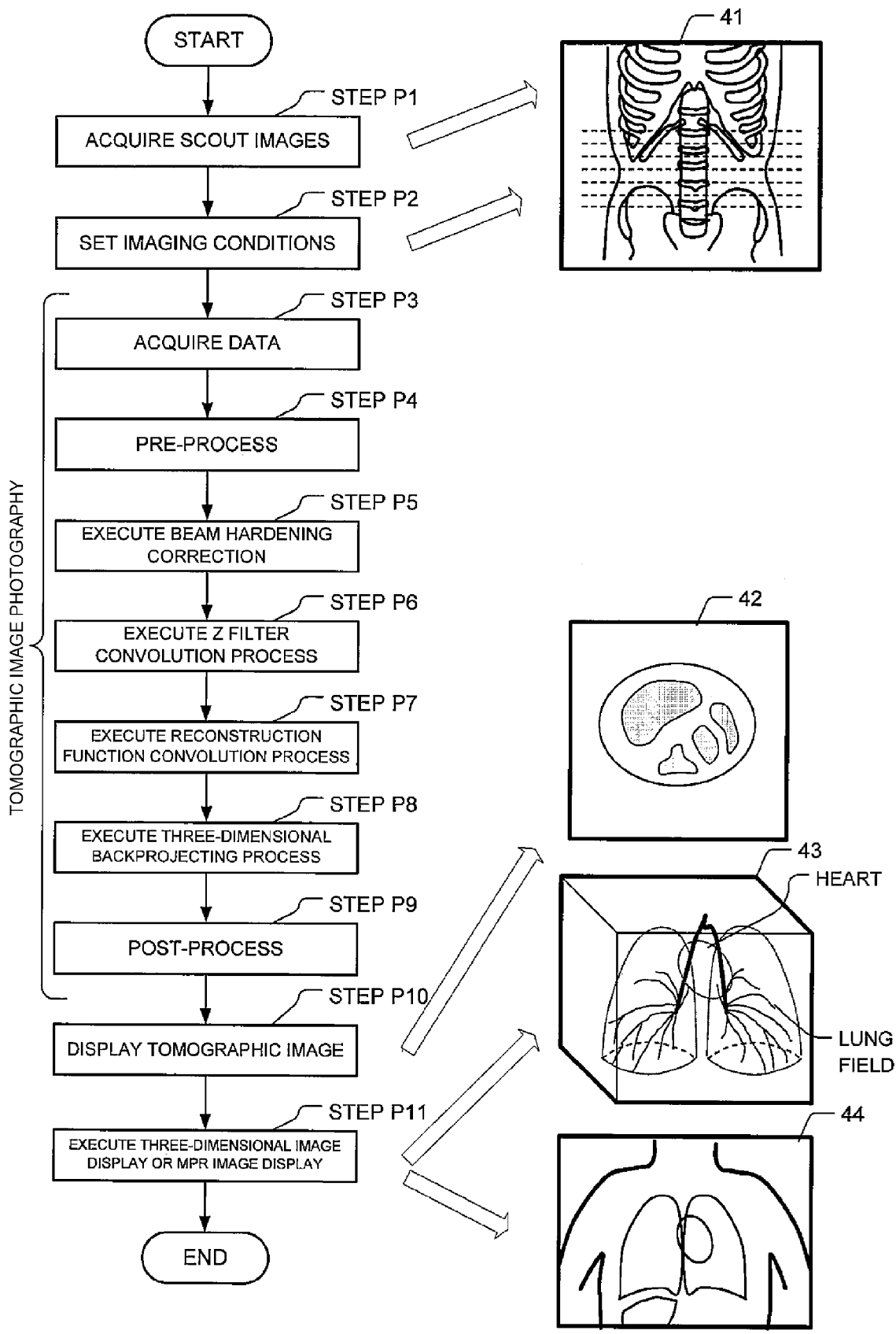
FIG. 2 is a flowchart illustrating an outline of operation of the X-ray CT apparatus according to the present embodiment.

FIG. 2 is a flowchart showing an outline of the operation of the X-ray CT apparatus according to the present embodiment.

At Step P1, a subject is placed on its corresponding cradle 12 and their alignment is performed. In the subject placed on the cradle 12, a slice light central position of the scan gantry 20 is aligned with a reference point of its each portion or region. Then, scout image (called also "scano image or X-ray penetrated image") acquisition is performed. The operation of fixing the X-ray tube 21 and the multi-row X-ray detector 24 and effecting data acquisition of X-ray detector data while the cradle 12 is being linearly moved, is performed upon scout image photography. Here, the scout image is normally imaged or photographed at view angular positions of 0° and 90°. Incidentally, only the 90° scout image might be taken depending upon the region as in the case of a head, for example. The right side shown in FIG. 2 is an example of a scout image 41 obtained by photographing the neighborhood of a chest region at 0°. The position of imaging or scanning of a tomographic image can be planned from above the scout image 41.

At Step P2, an imaging condition setting is performed while the position and size of each tomographic image to be photographed on the scout image 41 is being displayed. Dotted lines indicated in the scout image 41 indicate positions of tomographic images. The present embodiment has a plurality of scan patterns such as a conventional scan (axial scan), a helical scan, a variable pitch helical scan, a helical shuttle scan, etc. The conventional scan is a scan method of rotating the X-ray tube 21 and the multi-row X-ray detector 24 each time the cradle 12 is moved at predetermined intervals in a z-axis direction, thereby acquiring X-ray projection data. The helical scan is a photographing or imaging method of moving the cradle 12 at a constant velocity while an X-ray data acquisition system constituted of the X-ray tube 21 and the multi-row X-ray detector 24 is being rotated, thereby acquiring X-ray projection data. The variable pitch helical scan is an imaging method of varying the speed or velocity of the cradle 12 while the X-ray data acquisition system constituted of the X-ray tube 21 and the multi-row X-ray detector 24 is being rotated in a manner similar to the helical scan, thereby acquiring X-ray projection data. The helical shuttle scan is a scan method of accelerating/decelerating the cradle 12 while the X-ray data acquisition system constituted of the X-ray tube 21 and the multi-row X-ray detector 24 is being rotated in a manner similar to the helical scan, thereby to reciprocate it in the positive or negative direction of a z axis to acquire X-ray projection data. When these plural photographies are set, information about the whole X-ray dosage corresponding to once is displayed.

Upon setting the imaging conditions for tomographic images, radiation exposure of the subject can also be optimized by using an autoexposure mechanism of the X-ray CT apparatus 100. Upon the setting of the tomographic-image imaging conditions, an imaging condition at a low X-ray tube voltage of the X-ray tube 21, e.g., 80 kV, and an imaging condition at a high X-ray tube voltage, e.g., 140 kV can be set for the purpose of tomographic image photography corresponding to a so-called dual energy scan. In the autoexposure mechanism at the dual energy scan, the imaging condition for the low X-ray tube voltage and the imaging condition for the high X-ray tube voltage can be determined in such a manner that a noise index value of the final image for the dual energy tomographic image is approximately equal to a set noise index value. At this time, it is preferable to define the imaging conditions for the low and high X-ray tube voltages from the viewpoint of optimization of X-ray exposure in such a manner that image noise of a tomographic image at the low X-ray tube voltage and image noise of a tomographic image at the high X-ray tube voltage become approximately equal to each other.

At Steps P3 to P9, tomogram imaging is performed. At Step P3, X-ray data acquisition is executed. When the data acquisition is now carried out by the helical scan, the operation of acquiring X-ray detector data is performed while the X-ray tube 21 and the multi-row X-ray detector 24 are being rotated about the subject and the cradle 12 placed on the photographic table 10 is being linearly moved. Then, a z-direction coordinate position Ztable(view) is added to X-ray detector data D0(view, j, i) (where j=1 to ROW, and i=1 to CH) indicated by a view angle view, a detector row number j and a channel number i. Thus, the X-ray detector data acquisition relative to a range at a constant speed is performed upon the helical scan. The z-direction coordinate position may be added to X-ray projection data (X-ray detector data) or may be used in association with the X-ray projection data as another file. Information about the z-direction coordinate position is used where the X-ray projection data is three-dimensionally image-reconstructed upon the helical shuttle scan and the variable pitch helical scan. Using the same upon the helical scan, conventional scan or cine scan, an improvement in the accuracy of each image-reconstructed tomographic image and an improvement in its quality can be also realized.

The z-direction coordinate position may use position control data on the cradle 12 placed on the photographing table 10. Alternatively, z-direction coordinate positions at respective times, which are predicted from the imaging operation set upon the imaging condition setting, may also be used. Upon executing X-ray data acquisition by the conventional scan or the cine scan, the X-ray data acquisition system is rotated once or plural times while the cradle 12 placed on the photographing table 10 is being fixed to a given z-direction position, thereby to perform data acquisition of X-ray detector data. The cradle 12 is moved to the following z-direction position as needed and thereafter the X-ray data acquisition system is rotated once or plural times again to perform data acquisition of X-ray detector data.

At Step P4, the pre-processor 31 performs a pre-process. Here, the pre-processor 31 performs the pre-process on the X-ray detector data D0(view, j, i) and converts it into projection data. Described specifically, an offset correction is performed, logarithmic translation is performed, an X-ray dosage correction is performed, and a sensitivity correction is performed.

At Step P5, the beam hardening processor 33 performs a beam hardening correction. Here, the beam hardening processor 33 effects the beam hardening correction on the pre-processed projection data D1(view, j, i). Since, at this time, beam hardening corrections independent of one another every j row of detector can be performed, the differences in X-ray energy characteristics of the detectors for every row can be corrected if tube voltages of respective data acquisition systems are different depending on the imaging conditions.

At Step P6, the image reconstruction unit 34 performs a z-filter convolution process. Here, the image reconstruction unit 34 performs a z-filter convolution process for applying filters in the z direction (row direction) on the projection data D11(view, j, i) subjected to the beam hardening correction. That is, after the pre-process at each view angle and each X-ray data acquisition system, projection data of the multi-row X-ray detector D11(view, j, i) (where i=1 to CH and j=1 to ROW) subjected to the beam hardening correction is multiplied by filters in which, for example, row-direction filter sizes are five rows, in the row direction.

When row-direction filter coefficients are changed for every channel, slice thicknesses can be controlled depending upon the distance from an image reconstruction center. In a tomographic image, its peripheral portion generally becomes thick in slice thickness than the reconstruction center thereof. Therefore, the row-direction filter coefficients are changed at the central and peripheral portions so that the slice thicknesses can also be made uniform even at the peripheral portion and the image reconstruction central portion. When, for example, the row-direction filter coefficients are changed at the central and peripheral portions, the row-direction filter coefficients are changed extensively in width in the neighborhood of a central channel, and the row-direction filter coefficients are changed narrowly in width in the neighborhood of a peripheral channel, each slice thickness can be made approximately uniform even at both the peripheral portion and image reconstruction central portion.

By controlling the row-direction filter coefficients for the central and peripheral channels of the multi-row X-ray detector 24 in this way, each slice thickness can be controlled at the central and peripheral portions. Slightly thickening the slice thickness by the row-direction filters provides great improvements in both artifact and noise. Thus, the degree of an improvement in artifact and the degree of an improvement in noise can also be controlled. That is, the three-dimensionally image-reconstructed tomographic image, i.e., the image quality in the xy plane can be controlled. As another embodiment, a tomographic image having a thin slice thickness can also be realized by subjecting the row-direction (z-direction) filter coefficients to deconvolution filters. As the need arises, X-ray projection data for a fan beam is converted to X-ray projection data for a parallel beam.

At Step P7, the image reconstruction unit 34 performs a reconstruction function convolution process. That is, the image reconstruction unit 34 performs Fourier transform for transforming X-ray projection data into a frequency domain or region and multiplies it by a reconstruction function to perform inverse Fourier transform. Assuming that upon the reconstruction function convolution process, projection data subsequent to the z filter convolution process is defined as D12, projection data subsequent to the reconstruction function convolution process is defined as D13, and the convoluting reconstruction function is defined as Kernel(j), the reconstruction function convolution process is expressed as follows (Equation 1). Incidentally, a convolution computation or operation is expressed in "*" in the present embodiment.

Equation 1

$$D13(\text{view},j,i) = D12(\text{view},j,i) * Kernel(j) \quad (1)$$

That is, since the reconstruction function Kernel (j) performs reconstruction function convolution processes independent of one another for every j row of detector, the difference between noise characteristics set for every row and the difference between resolution characteristics can be corrected.

At Step P8, the image reconstruction unit 34 performs a three-dimensional backprojecting process. Here, the image reconstruction unit 34 effects the three-dimensional backprojecting process on the projection data D13(view, j, i) subjected to the reconstruction function convolution process to determine backprojection data D3(x, y, z). An image to be image-reconstructed is three-dimensionally image-reconstructed on an xy plane corresponding to a plane orthogonal to the z axis. A reconstruction area or plane P to be shown below is assumed to be parallel to the xy plane. The three-dimensional backprojecting process will be explained later referring to FIG. 3.

At Step P9, the image reconstruction unit 34 performs a post-process. The image reconstruction unit 34 effects a post-process such as image filter convolution, CT value conversion and the like on the backprojection data D3(x, y, z) to obtain a tomographic image D31(x, y, z). Assuming that upon the image filter convolution process in the post-process, a tomographic image subsequent to the three-dimensional backprojection is defined as D31(x, y, z), data subsequent to the image filter convolution is defined as D32(x, y, z), and a two-dimensional image filter subjected to convolution on the xy plane corresponding to a tomographic image plane is defined as Filter(z), the following equation (Equation 2) is established.

Equation 2

$$D32(x,y,z) = D31(x,y,z) * Filter(z) \quad (2)$$

That is, since the image filter convolution processes independent of one another for every tomographic image at each z-coordinate position can be carried out, the differences between noise characteristics and between resolution characteristics for every row can be corrected.

Alternatively, an image space z-direction filter convolution process shown below may be carried out after the two-dimensional image filter convolution process. This image space z-direction filter convolution process may be performed before the two-dimensional image filter convolution process. Further, a three-dimensional image filter convolution process may be performed to produce such an effect as to share both of the two-dimensional image filter convolution process and the image space z-direction filter convolution process.

Assuming that upon the image space z-direction filter convolution process, a tomographic image subjected to the image space z-direction filter convolution process is defined as D33 (x, y, z) and a tomographic image subjected to the two-dimensional image filter convolution process is defined as D32 (x, y, z), the following equation (Equation 3) is established as follows. In the equation (3), v(i) indicates an image space z-direction filter coefficient at which a z-direction width is 2l+1. v(i) is expressed in the form of such a coefficient row as shown below (Equation 4).

Equation 3 (3)
$$D33(x, y, z) = \sum_{i=-l}^{l} D32(x, y, z+i) \cdot v(i).$$

Equation 4 (4)
$$v(-l), v(-l+1), \ldots v(-l)v(0), v(1), \ldots v(l-1), v(l).$$

Upon the helical scan, the image space filter coefficient v(i) may be an image space z-direction filter coefficient independent upon the z-direction position. However, when the conventional scan or cine scan is performed using the two-dimensional X-ray area detector 24 or multi-row X-ray detector 24 or the like broad in detector width in the z direction in particular, the image space z-direction filter coefficient v(i) may preferably use an image space z-direction filter coefficient that depends upon the position of each X-ray detector row in the z direction. This is because it is further effective since detailed adjustments dependent on the row positions of respective tomographic images can be made.

At Step P10, an image-reconstructed tomographic image is displayed. As an example of the tomographic image, a tomographic image 42 is shown on the right side of FIG. 2.

At Step P11, a three-dimensional image display or an MRP (Multi Plain Reformat) image display is performed. Here, as tomographic images photographed continuously in the z direction, a three-dimensional image 43 and an MRP image 44 displayed by a three-dimensional MIP (Maximum Intensity Projection) image display method are shown. Although other various image display methods are known, an operator suitably makes proper use of image display methods according to diagnostic applications.

Flowchart of Three-Dimensional Backprojecting Process.

Figure 3:
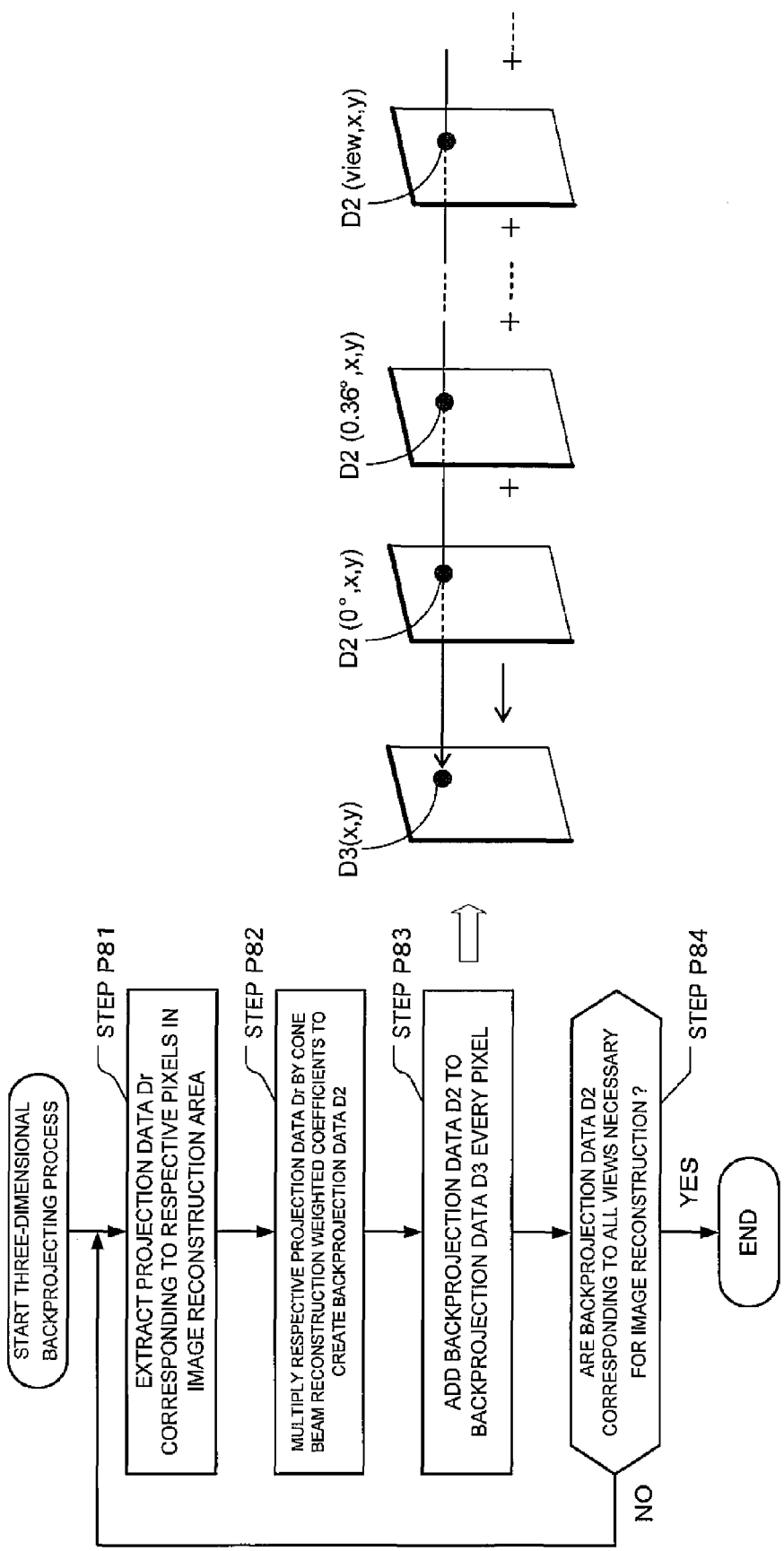
FIG. 3 is a flowchart depicting the details of a three-dimensional backprojecting process.

FIG. 3 is a flowchart showing the details of the three-dimensional backprojecting process (Step S8 in FIG. 2). In the present embodiment, an image to be image-reconstructed is three-dimensionally image-reconstructed on a plane, i.e., an xy plane orthogonal to the z axis. That is, the following reconstruction area is assumed to be parallel to the xy plane.

At Step P81, attention is paid to one of all views i.e., views corresponding to 360° or all views for X-ray fan beam projection data corresponding to 180°+fan angles necessary for image reconstruction of each tomographic image, or all views corresponding to 360° or 180° in the case of fan parallel-converted X-ray parallel beam projection data. Projection data Dr corresponding to respective pixels in the reconstruction area are extracted.

The X-ray penetration direction is determined depending on geometrical positions of the X-ray focal point of the X-ray tube 21, the respective pixels and the multi-row X-ray detector 24. The z coordinates z(view) of X-ray detector data D0(view, j, i) are known with being added to the X-ray detector data as a table linear movement z-direction position Ztable (view). Therefore, the X-ray penetration direction can be accurately determined within the X-ray focal point of the X-ray tube 21 and the data acquisition system of the multi-row X-ray detector 24 even in the case of the X-ray detector data D0(view, j, i) placed under acceleration and deceleration.

Incidentally, when some of lines are placed out of the multi-row X-ray detector 24 as viewed in the channel direction, the corresponding projection data Dr(view, x, y) is set to "0". When it is placed outside the multi-row X-ray detector 24 as viewed in the z direction, the corresponding projection data Dr(view, x, y) is determined by extrapolation.

At Step P82, the projection data Dr(view, x, y) are multiplied by cone beam reconstruction weighted addition coefficients ωa and ωb to create projection data D2(view, x, y). Cone-angle artifacts can be reduced by multiplying the same by the cone beam reconstruction weighted addition coefficients ωa and ωb and adding them. In the case of the fan beam image reconstruction, each pixel on the reconstruction area is further multiplied by a distance coefficient. Assuming that the distance from the focal point of the X-ray tube 21 to each of the detector row j and channel i of the multi-row X-ray detector 24 corresponding to the projection data Dr is r0, and the distance from the focal point of the X-ray tube 21 to each pixel on the reconstruction area P corresponding to the projection data Dr is r1, the distance coefficient is given as $(r1/r0)^2$. In the case of parallel beam image reconstruction, each pixel on the reconstruction area P may be multiplied by the cone beam reconstruction weighted addition coefficient w(i, j) alone. Incidentally, ωa+ωb=1.

At Step P83, the projection data D2(view, x, y) is added to its corresponding backprojection data D3(x, y) in association with each pixel. Described specifically, the projection data D2(view, x, y) is added to its corresponding backprojection data D3(x, y) cleared in advance in association with each pixel. The drawing indicated on the right side of FIG. 3 shows the concept that the projection data D2(view, x, y) is added for every pixel.

At Step P84, it is determined whether the backprojection data D2 corresponding to all views necessary for image reconstruction are added. When all are not added here, Steps P81 through S83 are repeated with respect to all views (i.e., views corresponding to 360° or views corresponding to "180°+fan angles") necessary for image reconstruction of each tomographic image. All the views necessary for the image reconstruction are added together. When all are added together, the present processing is terminated.

Dual Energy Scan or Photography.

In the above X-ray CT apparatus 100, a two-dimensional distribution tomographic image about X-ray tube voltage-dependent information related to a distribution of atoms is obtained. That is, a two-dimensional distribution tomographic image of a substance desired to be discriminated or a substance desired to be emphasized is obtained based on tomographic images subjected to a so-called dual energy scan. The present invention optimizes spatial resolution of each tomographic image indicative of the X-ray tube voltage-dependent information or image noise thereof. Embodiments related to it will be shown below.

First Embodiment

This is an embodiment in which in order to adjust the image quality of each tomographic image subjected to the dual energy scan in matching with an index value corresponding to a target for image quality, image reconstructing conditions for a plurality of X-ray tube voltage-based tomographic images are fed back to perform a readjustment.

Second Embodiment

This is an embodiment in which imaging conditions and image reconstructing conditions for a plurality of X-ray tube voltage-based tomographic images are adjusted in such a manner that an index value corresponding to a target for image quality is given to each tomographic image subjected to the dual energy scan and its index value is satisfied.

Third Embodiment

This is an embodiment in which when a mis-registration artifact is found in each tomographic image subjected to a dual energy scan, a registration or alignment correction is done to optimize the image quality of the tomographic image subjected to the dual energy scan to targeted image quality, i.e., an index value.

Fourth Embodiment

This is an embodiment in which when mis-registration or displacement (displacement in xy plane) in a tomographic-image plane direction is detected at a tomographic image subjected to a dual energy scan or upon a three-dimensional display or an MPR display, processing is returned to image reconstruction of a plurality of X-ray tube voltage-based tomographic images to perform their displacement corrections and plural X-ray tube voltage-based image reconstruction is redone, thereby optimizing the quality of each tomographic image subjected to the dual energy scan, the quality of a three-dimensionally displayed image, and the quality of an MPR-displayed image.

First Embodiment

Figure 4:
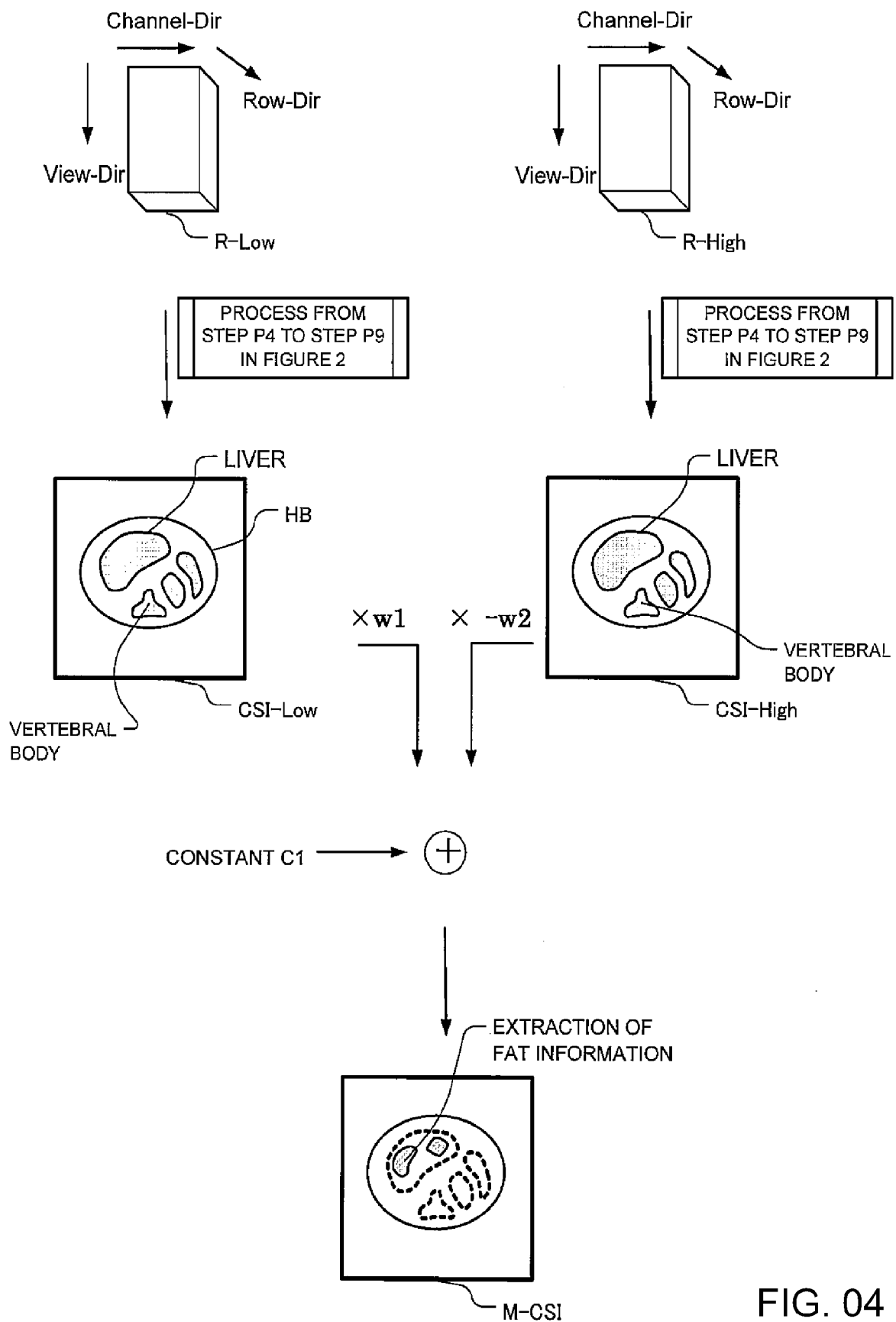
FIG. 4 is a diagram showing how to determine tomographic images of X-ray tube voltage-dependent information about X-ray absorption coefficients in an image space.

FIG. 4 is a diagram for determining tomographic images obtained by subjecting tomographic images corresponding to a low X-ray tube voltage and a high X-ray tube voltage to a weight adding process upon tomographic image photography at the low X-ray tube voltage and the high X-ray tube voltage and effecting a dual energy scan on the same.

As to the so-called dual energy scan, a tomographic image at a low X-ray tube voltage, for example, 80 kV and a tomographic image at a high X-ray tube voltage, for example, 140 kV are subjected to a weight adding process at a given z-direction coordinate position, thereby determining a tomographic image M-CSI corresponding to a quantitative distribution image of a desired substance.

As shown in FIG. 4, X-ray projection data R-Low of a low X-ray tube voltage and X-ray projection data R-High of a high X-ray tube voltage are first determined. The image reconstruction unit 34 performs Steps P4 to P9 as described in FIG. 2 from the X-ray projection data R-Low of the low X-ray tube voltage and the X-ray projection data R-High of the high X-ray tube voltage and thereby image-reconstructs a tomographic image CSI-Low at the low X-ray tube voltage and a tomographic image CSI-High at the high X-ray tube voltage. The dual energy image reconstruction unit 35 multiplies the tomographic image CSI-Low at the low X-ray tube voltage by a weighted addition coefficient w1 and multiplies the tomographic image CSI-High at the high X-ray tube voltage by a weighted addition coefficient −w2, and performs a weight adding process together with a constant C1. The weighted addition coefficients w1 and w2 and the constant C1 are determined depending on atoms desired to be extracted, atoms desired to be emphasized, and atoms or regions desired to be eliminated on the display. Supposing that where it is desired to separate a calcium component (Ca component) constituting a bone or calcification, which is close to a contrast agent in CT value and the contrast agent (Iodine component) with iodine as a principal component from each other, for example, weighted addition coefficients are adjusted to eliminate the calcium component on the display, i.e., a pixel value of the calcium component is set to 0, the Iodine component is extracted and displayed with being emphasized. When the contrast agent component is eliminated on the display in reverse, i.e., the pixel value of the Iodine component is set to 0, the calcium component is extracted and the bone or calcified portion or region is emphasized and displayed. FIG. 4 shows an emphasized image about fat information.

A CT value of a tomographic image image-reconstructed from projection data based on X rays of energy A, and a CT value of a tomographic image image-reconstructed from projection data based X rays of energy B are respectively given from the following equation (5).

Equation 5.

$$CT_A = \alpha_A X + \beta_A Y + \gamma_A$$
$$CT_B = \alpha_B X + \beta_B Y + \gamma_B \quad (5)$$

where X and Y respectively indicate desired substances (unknown quantity). αA, αB, βA, βB, γA and γB respectively indicate constants known by measurement in advance. The substances X and Y are respectively determined from such CT values in accordance with the following equations (6).

Equation 6 (6)

$$X = \frac{(CT_A - \gamma_A)\beta_B - (CT_B - \gamma_B)\beta_A}{\alpha_A \beta_B - \alpha_B \beta_A}$$

$$Y = \frac{(CT_A - \gamma_A)\alpha_B - (CT_B - \gamma_B)\alpha_A}{\alpha_B \beta_A - \alpha_A \beta_B}$$

Thus, an image related to the substance X, and an image related to the substance Y are respectively formed. The elements of X and Y or the substances X and Y are, for example, a calcium component, fat, an iron component and the like. Thus, a tomographic image M-CSI corresponding to a quantitative distribution image of a desired substance can be obtained from two tomographic images different in X-ray quality. That is, a tomographic image M-CSI corresponding to a distribution image in which the substances X and Y exist, is obtained by a weight adding process of a tomographic image CSI-Low at a low X-ray tube voltage and a tomographic image CSI-High at a high X-ray tube voltage.

The above description has shown a method of image-reconstructing each tomographic image subjected to a so-called dual energy scan in an image space and a tomographic image space.

Figure 5:
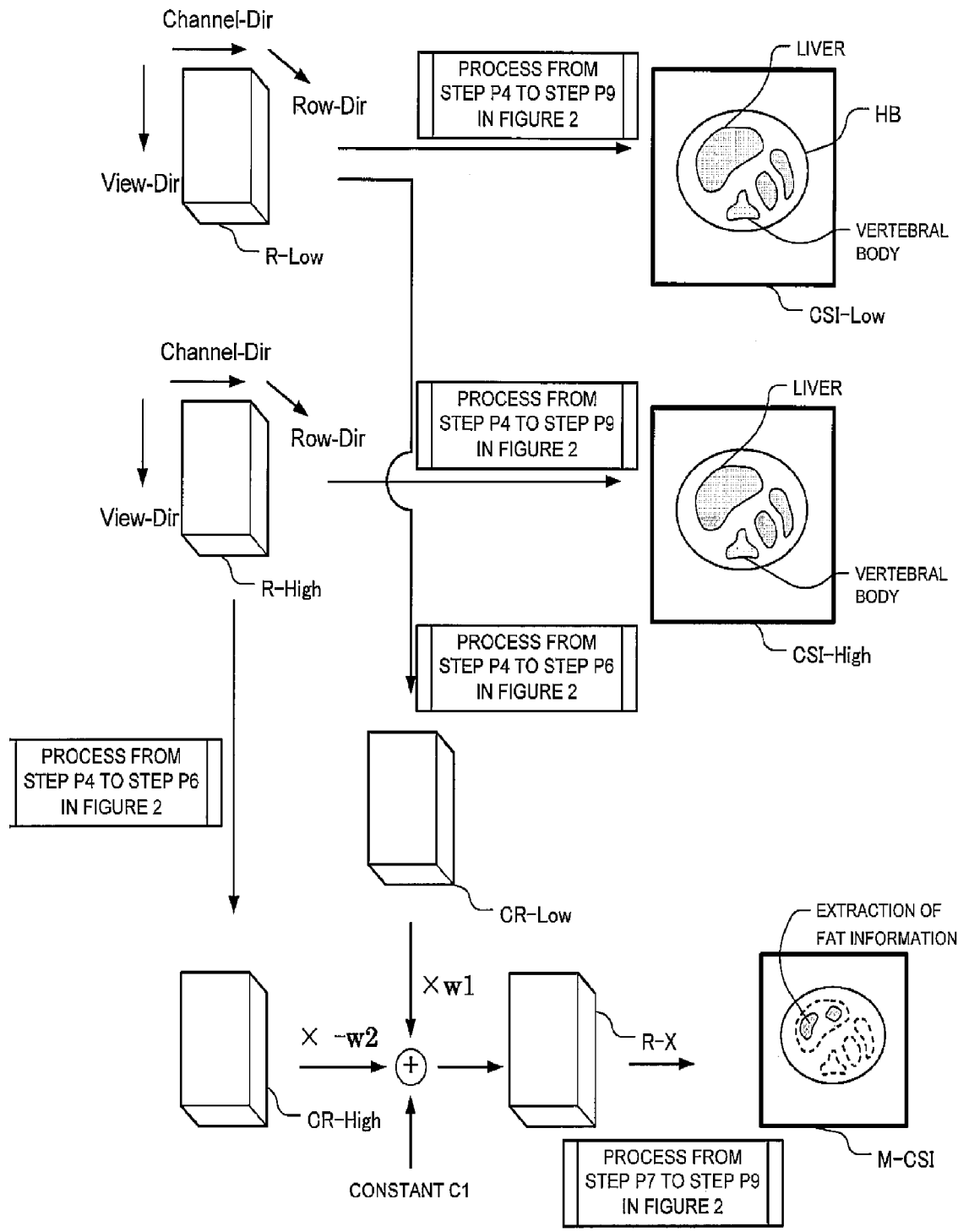
FIG. 5 is a diagram illustrating how to determine tomographic images of X-ray tube voltage-dependent information about X-ray absorption coefficients in a projection data space.

FIG. 5 is a diagram for determining a dual energy-photographed or scanned tomographic image M-CSI by subjecting respective X-ray projection data corresponding to X-ray projection data R-Low acquired at a low X-ray tube voltage and X-ray projection data R-High acquired at a high X-ray tube voltage to a weight adding process and image-reconstructing the X-ray projection data subjected to the weight adding process.

The method shown in FIG. 4 is susceptible to beam hardening when the sectional area of a subject becomes large, and weighted addition coefficients might slightly differ according to the size of the sectional area of the subject. In order to avoid it, a tomographic image subjected to a so-called dual energy scan is image-reconstructed in an X-ray projection data space, and a beam hardening correction is effected on either one of X-ray projection data prior or subsequent to their weight adding process to thereby obtain a tomographic image M-CSI subjected to the dual energy scan.

Here, the dual energy image reconstruction unit 35 multiplies the X-ray projection data R-Low of the low X-ray tube voltage by a weighted addition coefficient w1 and multiplies the X-ray projection data R-High of the high X-ray tube voltage by a weighted addition coefficient −w2, and performs a weight adding process together with a constant C1. However, w1−(−w2)=1.

In a manner similar to the tomographic images subjected to the dual energy scan in the image space and tomographic image space, which have been described in FIG. 4, the weighted addition coefficients w1 and w2 and the constant C1 are determined depending upon atoms desired to be extracted, atoms desired to be emphasized, and atoms or regions desired to be eliminated on the display. Supposing that where it is desired to separate a calcium component (Ca component) constituting a bone or calcification, which is close to a contrast agent in CT value and a contrast agent (Iodine component) with iodine as a principal component from each other, for example, the calcium component is eliminated on the display, i.e., a pixel value of the calcium component is set to 0, its Iodine component is extracted and displayed with being emphasized. When the contrast agent component is eliminated on the display in reverse, i.e., the pixel value of the contrast agent component is set to 0, the calcium component is extracted and the bone or calcified portion or region is emphasized and displayed.

How to determine the weighted addition coefficients w1 and w2 and the constant C1 at this time is shown below.

It is possible to determine X-ray projection data of substances X and Y by the weight adding process in a projection data space in FIG. 5. Obtaining tomographic images of the substances X and Y by image-reconstructing the X-ray projection data of the substances X and Y will be shown below. That is, assuming that X-ray projection data of a low X-ray tube voltage is defined as R-Low and X-ray projection data of a high X-ray tube voltage is defined as R-High, and the X-ray projection data of the subject X is defined as $R_X$ and the X-ray projection data of the substance Y is defined as $R_Y$, the X-ray projection data of the substance X and the X-ray projection data of the substance Y are determined as expressed in the following equation (7).

Equation 7.

$$R_X = w1 \cdot R_{Low} + w2 \cdot R_{High} + c1$$

$$R_Y = w3 \cdot R_{Low} + w4 \cdot R_{High} + c2 \quad (7)$$

By image-reconstructing the X-ray projection data $R_X$ of the substance X and the X-ray projection data $R_Y$ of the subject Y, tomographic images of the substances X and Y are obtained.

In the projection data space of FIG. 5, the image reconstruction unit 34 determines X-ray projection data R-Low of a low X-ray tube voltage and X-ray projection data R-High of a high X-ray tube voltage using the weight adding process for the X-ray projection data and image-reconstructs them thereby to determine a tomographic image CSI-Low at the low X-ray tube voltage and a tomographic image CSI-High at the high X-ray tube voltage. As the X-ray projection data R-Low or R-High used at this time, the X-ray projection data subjected to the pre-process and beam hardening correction is used. Setting penetration path lengths of X rays transmitted through water at the respective X-ray tube voltages upon the beam hardening correction in particular enables more correct evaluation of dependence of X-ray absorption coefficients of a substance other than water on the X-ray tube voltages.

Control method of X-ray tube voltage. A method for performing imaging at a low X-ray tube voltage and imaging at a high X-ray tube voltage in the present embodiment will next be explained.

Even in the case of the conventional X-ray CT apparatus, a region of a subject HB desired to be dual energy-photographed, i.e., its same region is photographed at a low X-ray tube voltage and a high X-ray tube voltage upon a conventional scan or the like, followed by being subjected to image reconstruction by the image reconstructing method based on the dual energy scan shown above, whereby tomographic images subjected to the dual energy scan could be obtained. In the normal conventional scan or the like, however, mis-registration due to body motion such as respiration, beat and the like of the subject occurs when temporal space is taken between imaging times necessary for a tomographic image at a low X-ray tube voltage and a tomographic image at a high X-ray tube voltage. Thus, mis-registration artifacts were easy to occur on the tomographic images subjected to the dual energy scan. In order to avoid it, the execution of faster imaging or photography by a recent X-ray CT apparatus capable of high-speed scan will be shown below.

Figure 6:
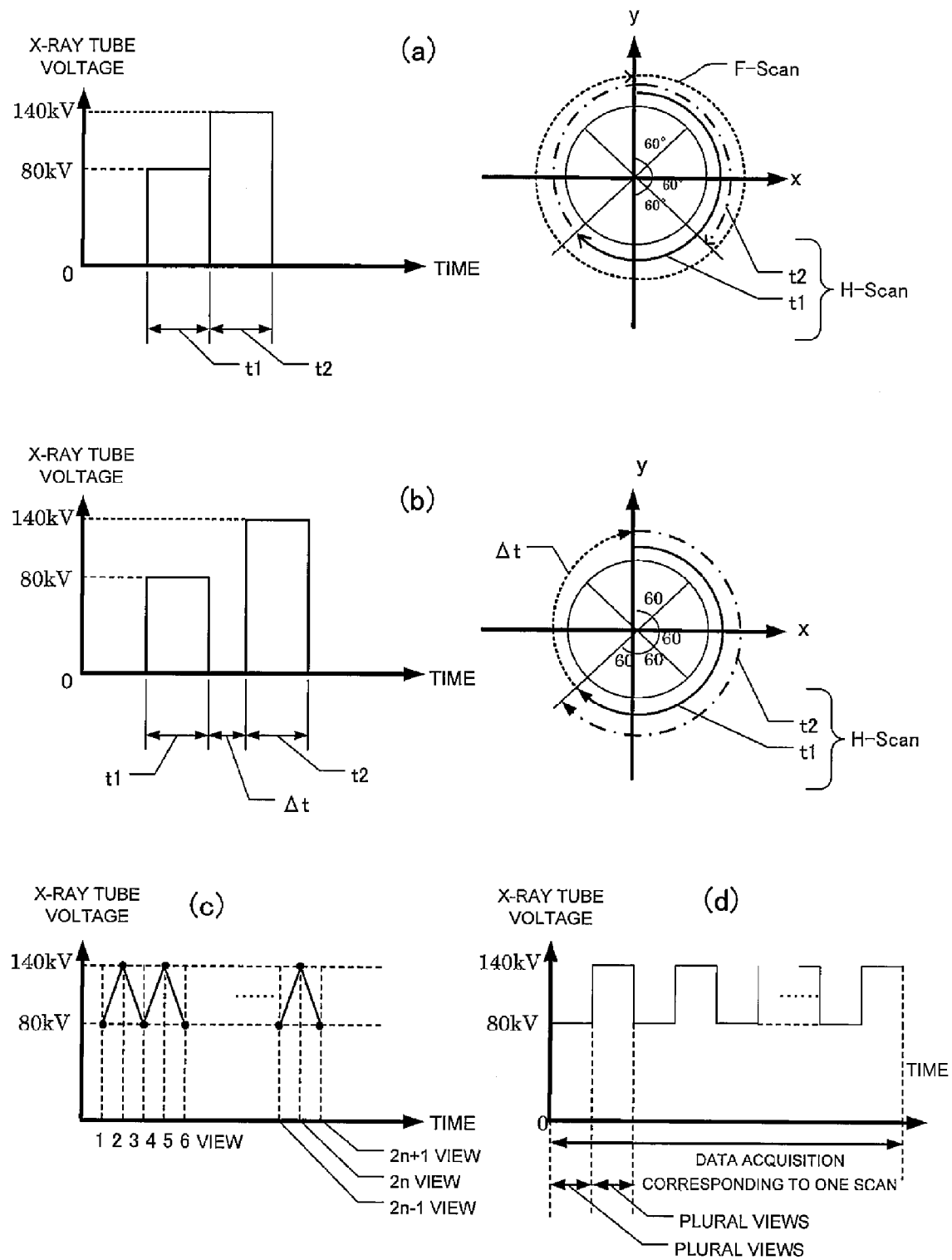
FIGS. 6(a) and 6(b) are examples in which X-ray tube voltages are respectively switched by continuous scans.
FIG. 6(c) is an example in which an X-ray tube voltage is switched every view.
FIG. 6(d) is an example in which an X-ray tube voltage is switched every data acquisition segment.

FIG. 6 is a diagram showing examples of switching between a low X-ray tube voltage and a high X-ray tube voltage.

As the first example, as shown in FIG. 6(a), imaging or photography at an imaging or scanning time t1 under an X-ray tube voltage 80 kV corresponding to a first scan, and imaging or photography at an imaging or scanning time t2 under an X-ray tube voltage 140 kC corresponding to a second scan are continuously performed. Conversely, the order of the imaging at the imaging time t1 under the X-ray tube voltage 140 kV corresponding to the first scan, the imaging at the imaging time t2 under the X-ray tube voltage 80 kV corresponding to the second scan, and the X-ray tube voltage may be reversed. In this case, the X-ray tube voltage is changed between the imaging time t1 and the imaging time t2. Normally, the same imaging time is set as in the case of t1=t2. At both imaging times t1 and t2, for example, X-ray projection data corresponding to 360° at a 360°-scan corresponding to a full scan F-Scan may be acquired. Alternatively, X-ray projection data corresponding to a scan of 180°+fan angles corresponding to a half scan H-Scan may be acquired at both imaging times t1 and t2.

Assuming that the fan angle of an X-ray fan beam of the multi-row X-ray detector 24 is 60°, X-ray projection data corresponding to 180°+fan angles=240°, i.e., ⅔ rotation are acquired at the half scan H-Scan. If the rotational velocity of the corresponding X-ray data acquisition system is 0.35 sec/rotation, then an imaging time of 1 sec or less is reached even in the case of imaging at the half scan H-Scan for a dual energy scan and imaging at the full scan. Therefore, the body motion of the subject can be substantially suppressed. Incidentally, in this case, the X-ray tube voltage is switched in a range of about 10 ms to 100 ms between the imaging time t1 and the imaging time t2. A rotational region (solid line) for the imaging time t1 at the half scan H-Scan, and a rotational region (one-dot chain line) for the imaging time t2 thereat are shown in the figure illustrative of an xy plane in FIG. 6(a).

Next, FIG. 6(b) is shown as the second example. When the time required to switch between the X-ray tube voltages is innegligible as compared with imaging times t1 and t2, the X-ray tube voltage is raised during Isd (Inter Scan Delay) of Δt between the imaging times t1 and t2. When it is desired to start acquisition of X-ray projection data from the same view angle at both first and second scans, the acquisition of X-ray projection data corresponding to 240° corresponding to the first scan at the imaging time t1 is performed, and the acquisition of X-ray projection data corresponding to a view angle of 120° at the time that Isd is Δt, is stopped, as shown in the figure of the xy plane in FIG. 6(b). Further, the acquisition of X-ray projection data corresponding to 240° associated with the second scan at the imaging time t2 is carried out. If done in this way, then the X-ray projection data acquisition can be started at the same view angle at both the first and second scans.

Incidentally, since the fan angle of the multi-row X-ray detector 24 is set as 60° in this case, the view angle reaches 240° in the case of the half scan during the imaging times t1 and t2. Thus, if the view angles for starting the acquisition of the X-ray projection data at the first and second scans are made coincident with each other, then a computation between the X-ray projection data at the half scan, e.g., a weight adding process of two X-ray projection data or the like makes it unnecessary trouble taken for a process of searching views and rearranging them, thereby making it easy to perform control.

Figure 7:
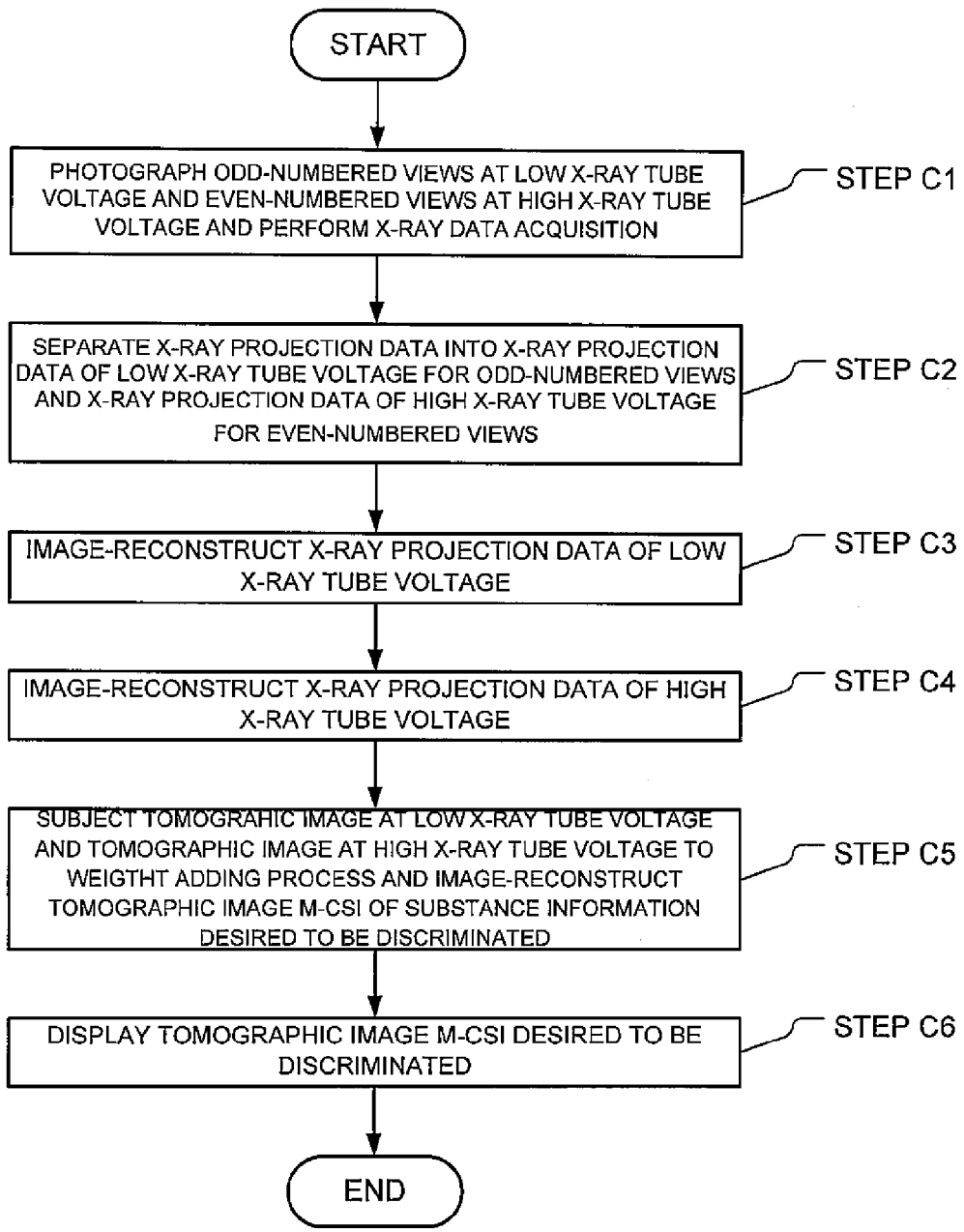
FIG. 7 is a flowchart showing an outline of image reconstruction where X-ray tube voltages are changed at odd/even views.

Next, FIG. 6(c) is shown as the third example. Another dual energy scan or photographing method almost unsusceptible to the body motion of the subject is shown. As shown in FIG. 6(c), for example, X-ray projection data of an X-ray tube voltage 80 kV are acquired every odd-numbered view and X-ray projection data of an X-ray tube voltage 140 kV are acquired every even-numbered view. FIG. 7 is a flowchart showing the outline of a process for image reconstruction in the case shown in FIG. 6(c).

At Step C1, odd-numbered views are imaged or photographed at a low X-ray tube voltage, and even-numbered views are imaged at a high X-ray tube voltage, whereby X-ray data acquisition is carried out.

At Step C2, X-ray projection data R-Low of the low X-ray tube voltage for every odd-numbered view, and X-ray projection data R-High of the high X-ray tube voltage for every even-numbered view are separated.

At Step C3, the X-ray projection data R-Low of the low X-ray tube voltage is image-reconstructed.

At Step C4, the X-ray projection data R-High of the high X-ray tube voltage is image-reconstructed.

At Step C5, each tomographic image at the low X-ray tube voltage and each tomographic image at the high X-ray tube voltage are subjected to a weight adding process, and a tomographic image indicative of substance information desired to be discriminated is image-reconstructed. The substance information desired to be discriminated is X-ray tube voltage-dependent information about an X-ray absorption coefficient of the substance desired to be discriminated. In other words, it is also an element distribution desired to be discriminated.

At Step C6, each tomographic image about the substance information desired to be discriminated is displayed.

As shown in FIG. 6(d), the acquisition of X-ray projection data of an X-ray tube voltage 80 kV and the acquisition of X-ray projection data of an X-ray tube voltage 140 kV may alternately be repeated every plural continuous views. Incidentally, even when the acquisition of the X-ray projection data of the low X-ray tube voltage and the acquisition of the X-ray projection data of the high X-ray tube voltage are performed in units of plural views as shown in FIG. 6(d), they are separated into X-ray projection data R-Low of the low X-ray tube voltage and X-ray projection data R-High of the high X-ray tube voltage, and the respective X-ray projection data may be image-reconstructed.

Thus, even when the 360° scan corresponding to the full scan or the "180°+fan angles" scan corresponding to the half scan are continuously carried out as shown in FIGS. 6(a) and 6(b), a tomographic image obtained by image-reconstructing the X-ray projection data obtained by subjecting the X-ray projection data R-Low of the low X-ray tube voltage and the X-ray projection data R-High of the high X-ray tube voltage to the weight adding process is brought to a tomographic image M-CSI subjected to a so-called dual energy scan or photography even by a method of performing switching between the X-ray tube voltages every view or every plural views. Further, a tomographic image obtained by subjecting the tomographic image CSI-Low at the low X-ray tube voltage and the tomographic image CSI-High at the high X-ray tube voltage to the weight adding process is brought to a tomographic image based on the so-called dual energy scan.

S/N ratio of tomographic image M-CSI based on dual energy photography.

Upon determining the tomographic image subjected to the dual energy scan or photography by the tomographic images at the plural X-ray tube voltages as described above, one of the weighted addition coefficients for the weight adding process becomes negative (minus). Therefore, there is a characteristic that the SN of each tomographic image subjected to the dual energy scan becomes poor as compared with the original tomographic images at the plural X-ray tube voltages, i.e., image noise gets worse or image quality is deteriorated. Therefore, the imaging conditions for the original tomographic images at the plural X-ray tube voltages must be determined in consideration of even image noise of each tomographic image subjected to the dual energy scan while exposure of the subject is being taken into consideration.

Figure 8:
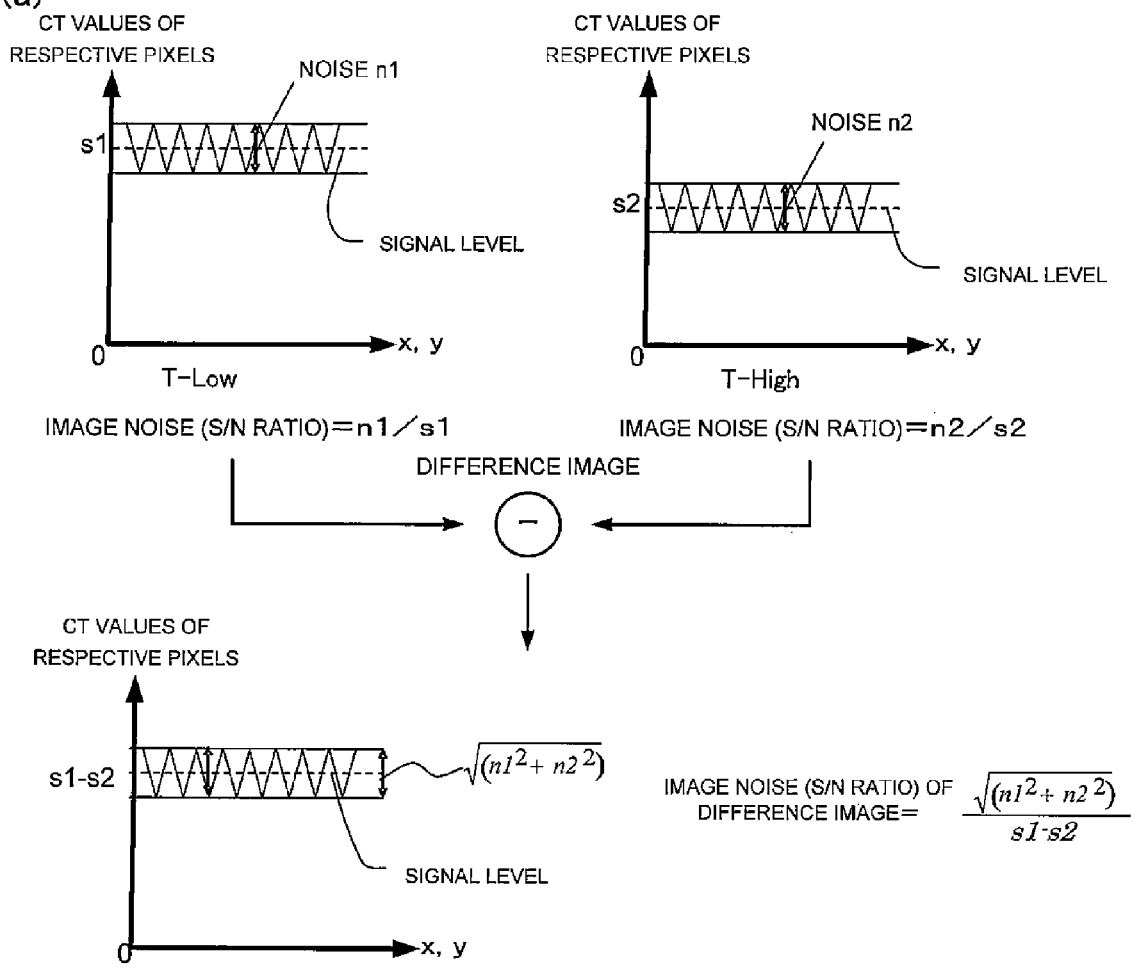
FIG. 8(a) is a diagram illustrating image noise at a difference image.
FIG. 8(b) is a diagram showing X-ray tube voltage-dependent characteristics of X-ray absorption coefficients.
Figure 8:
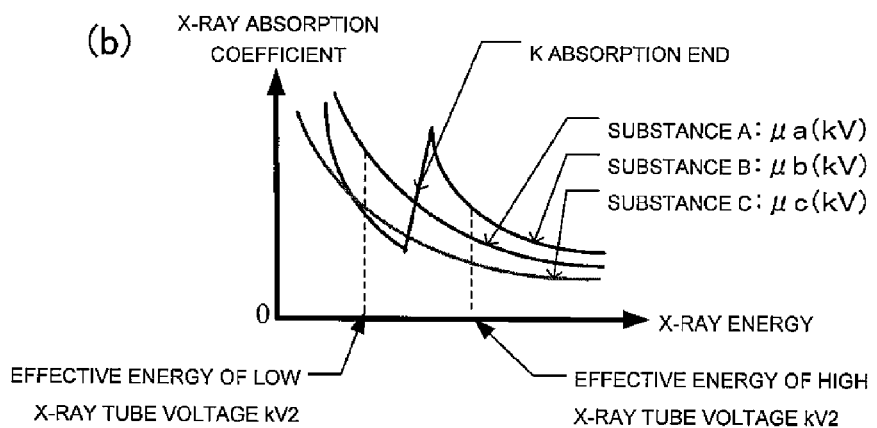

Determining, as shown in FIG. 8(a) in general, an image of difference between a tomographic image CSI-Low at a low X-ray tube voltage, in which image nose is N1, a signal is S1 and an S/N ratio thereof is N1/S1, and a tomographic image CSI-High at a high X-ray tube voltage, in which image noise is N2, a signal is S2 and an S/N ratio thereof is N2/S2 yields an S/N ratio of the difference image: SNSub as follows (Equation 8):

Equation 8 (8)

$$SNSub = \frac{\sqrt{(n1)^2 + (n2)^2}}{s1 - s2}$$

Incidentally, the following equation (9) is established by a theorem of arithmetic and geometric mean.

Equation 9

$$\sqrt{(n1)^2 + (n2)^2} \geq \sqrt{2 \cdot n1 \cdot n2} \qquad (9)$$

That is, when image noise N1 of a tomographic image at a low X-ray tube voltage kV1 and image noise N2 of a tomographic image at a high X-ray tube voltage kV2 are equal to each other, image noise NSub of the difference image is brought to the minimum.

Since the weighted addition coefficients w1 and w2 are included in the weight adding process in the present embodiment, the image noise is expressed like the following equation (10) in consideration of it with respect to the above.

Equation 10

$$N_{sub} \geq \frac{\sqrt{2 \cdot n1 \cdot n2}}{s1 \cdot s2} \tag{10}$$

That is, the image noise of the tomographic image CSI-Low at the X-ray tube voltage 80 kV and the image noise of the tomographic image CSI-High at the X-ray tube voltage 140 kV may be approximately equal to each other in consideration of the weighted addition coefficients.

A method of determining X-ray tube voltages for obtaining a better S/N ratio at X-ray exposed dose reduced as much as possible needs to be decided depending on a substance desired to be extracted and a substance to be emphasized.

FIG. 8(b) is a diagram showing X-ray tube voltage-dependence contained in each substance desired to be extracted. It is assumed that an X-ray absorption coefficient for each X-ray energy of a substance A is μa(kV), an X-ray absorption coefficient of each X-ray energy of a substance B is μb(kV), and an X-ray absorption coefficient of each X-ray energy of a substance C is μc(kV). It is also assumed that effective energy of a low X-ray tube voltage kV1 is ekV1, and effective energy of a high X-ray tube voltage kV2 is ekV2. Further, it is assumed that each of CT values of respective pixels in a tomographic image CSI of the X-ray CT apparatus 100 is ga(x, y), a conversion coefficient in the case of the X-ray tube voltage kV1 is CkV1, and a conversion coefficient in the case of the X-ray tube voltage kV2 is CkV2.

When the substance A is photographed at the low X-ray tube voltage kV1 and the high X-ray tube voltage kV2 in this case, the CT value of the substance A is given as CkV1·μa(ckV1) at kV1 and CkV2·μa(ekV2) at kV2.

At this time, the pixel value of each tomographic image subjected to the dual energy photography is expressed as follows (Equation 11):

Equation 11

$$ga(x,y) = w1 \cdot ckV1 \cdot \mu a(ekV1) - w2 \cdot ckV2 \cdot \mu a(ekV2) \tag{11}$$

This means that the substance A is eliminated and another substance is emphasized. When another substance B is eliminated, the substance A is emphasized.

Generally speaking, SN of the tomographic image subjected to the dual energy scan becomes better as Δμ shown below (Equation 12) becomes larger, and image noise is hence improved.

Equation 12

$$\Delta \mu a = \mu a(ekV1) - \mu a(ekV2) \tag{12}$$

Thus, in order to improve the image noise and SN of each tomographic image subjected to the dual energy scan, a substance, particularly, a contrast agent in which the difference between the X-ray absorption coefficient μ (ekV1) at the effective energy ekV1 of the low X-ray tube voltage kV1 and the X-ray absorption coefficient μ (ekV2) at the effective energy ekV2 of the high X-ray tube voltage kV2 is large, is selected. Further, the low X-ray tube voltage kV1 and the high X-ray tube voltage kV2 are selected in such a manner that the difference in the X-ray absorption coefficient of the substance becomes as large as possible. Thus, it is possible to improve the image noise and SN of the tomographic image subjected to the dual energy scan and reduce X-ray exposure.

In a substance B shown in FIG. 8(b) in particular, a sudden change in X-ray absorption coefficient occurs due to a K absorption end. Selecting the low X-ray tube voltage kV1 and the high X-ray tube voltage kV2 by making good use of such a sudden change in X-ray absorption coefficient makes it possible to improve image noise and SN of each tomographic image subjected to the dual energy imaging and reduce X-ray exposure.

There is a case in which the image noise of the tomographic image CSI-Low at the low X-ray tube voltage and the image noise of the tomographic image CSI-High at the high X-ray tube voltage cannot be made equal or approximately equal to each other depending on limiting conditions of the output of the X-ray tube 21 or the X-ray generator. In this case, upon image reconstruction of the tomographic image poor in image noise, image reconstruction is effected using each reconstruction function less reduced in image noise, or a noise filter with image space or a noise filter with X-ray projection data space is applied, thereby approximately equalizing the image noise of the tomographic image at the low X-ray tube voltage and the image noise of the tomographic image at the high X-ray tube voltage. Thus, a tomographic image indicative of X-ray tube voltage-dependent information about an X-ray absorption coefficient of a subject can be obtained with lesser exposure and better image quality.

However, the weighted addition coefficients w1 and w2 are determined depending upon what atom, substance and region should be eliminated and what atom, substance and region should be emphasized. When it is desired to eliminate calcium and iodine for a contrast agent using, for example, a tomographic image at an X-ray tube voltage 80 kV and a tomographic image at an X-ray tube voltage 140 kV, w1/w2 reaches a range from about 1/1.3 to 1/2. That is, the image noise of the tomographic image at the high X-ray tube voltage may be improved about two times or so.

If such an adjustment is made more correctly or automated, it may then be practiced to previously recognize to which extent each X-ray tube current value for a high X-ray tube voltage reaches image noise.

Figure 9:
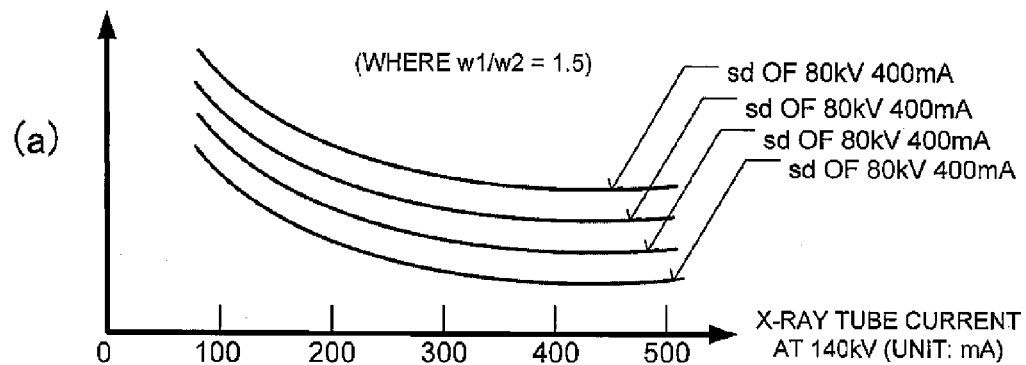
FIGS. 9(a) and 9(b) are graphs showing the relationship between respective X-ray tube current values for low X-ray tube voltages and respective X-ray tube current values for high X-ray tube voltages.
Figure 9:
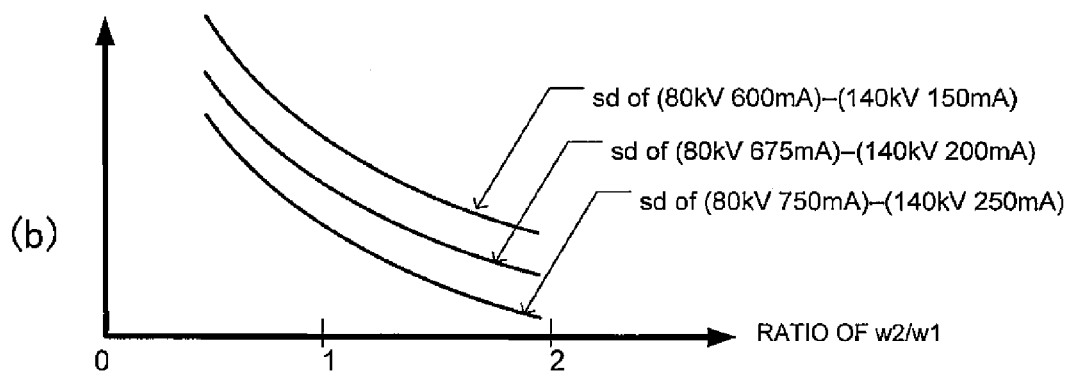

Relationship between respective X-ray current values at low X-ray tube voltage and respective X-ray tube current values at high X-ray tube voltage. FIG. 9 is a graph showing the relationship between respective X-ray tube current values at a low X-ray tube voltage and respective X-ray tube current values at a high X-ray tube voltage.

FIG. 9(a) shows results obtained where tomographic images corresponding to four types of 400 mA, 500 mA, 600 mA and 700 mA and tomographic images from X-ray tube currents 100 mA to 500 mA at an X-ray tube voltage 140 kV are combined together as imaging conditions at an X-ray tube voltage 80 kV. The results show measurements of standard deviations sd of respective pixel values of a water phantom whose diameter is 20 cm, for example.

FIG. 9(b) shows how the standard deviations sd of the respective pixel values of the water phantom whose diameter is 20 cm, change by combinations of imaging conditions at respective X-ray tube voltages 80 kV and imaging conditions at respective X-ray tube voltages 140 kV depending upon the ratio of w2/w1. FIG. 9(b) shows the standard deviations sd of the 20 cm-diameter water phantom where the ratio w2/w1 between the weighted addition coefficients is changed between 1.3 and 2.0 when the combinations of the imaging conditions at the X-ray tube voltages 80 kV and the imaging conditions at the X-ray tube voltages 140 kV are set as three combinations corresponding to a combination of an X-ray tube voltage 80 kV and an X-ray tube current 600 mA, and an X-ray tube voltage 140 kV and an X-ray tube current 150 mA, a combination of an X-ray tube voltage 80 kV and an X-ray tube current 675 mA, and an X-ray tube voltage 140 kV and an X-ray tube current 200 mA, and a combination of an X-ray tube voltage 80 kV and an X-ray tube current 750 mA, and an X-ray tube voltage 140 kV and an X-ray tube current 250 mA.

These information are stored in the storage device 7. Tomographic image photographing conditions at a plurality of X-ray tube voltages under a dual energy scan are determined and reconstructing conditions for tomographic images at a plurality of X-ray tube voltages are determined, in such a manner that noise index values of image quality at the dual energy scan, i.e., standard deviations sd of pixel values of tomographic images subjected to the dual energy scan can reach target values.

Figure 10:
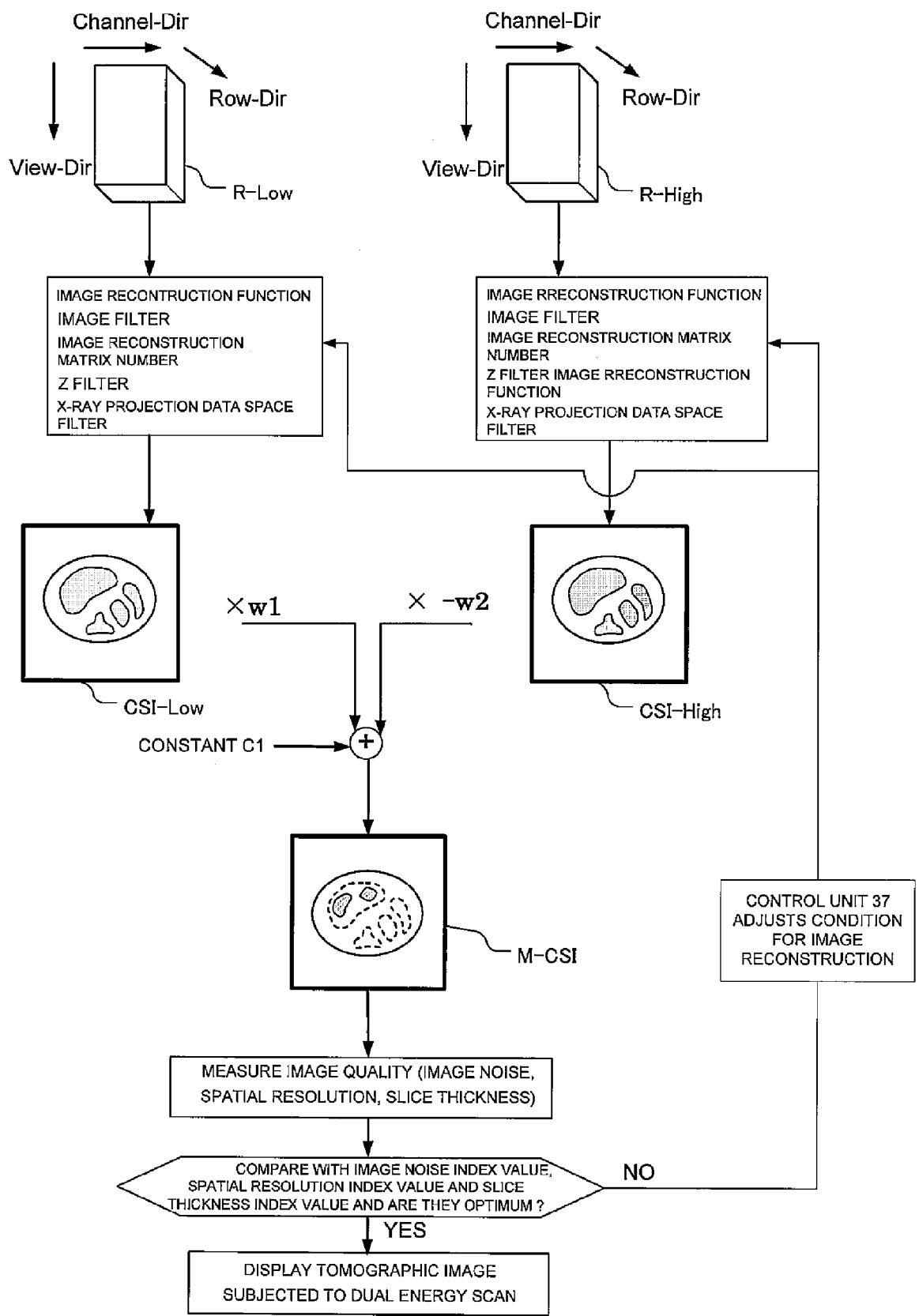
FIG. 10 is a diagram illustrating an outline of a dual energy scan in which image reconstructing conditions for a tomographic image at a low X-ray tube voltage and a tomographic image at a high X-ray tube voltage are fed back.

Feedback of image reconstructing conditions. FIG. 10 is a diagram showing the outline of a dual energy scan in which image reconstructing conditions for a tomographic image CSI-Low at a low X-ray tube voltage and a tomographic image CSI-High at a high X-ray tube voltage are fed back.

First, X-ray projection data R-Low acquired at a low X-ray tube voltage and X-ray projection data R-High acquired at a high X-ray tube voltage are obtained. An image reconstruction process is effected on these X-ray projection data R-Low and X-ray projection data R-High. A predetermined image filter, an image reconstruction function and the like are used in the image reconstruction. Thus, the tomographic image CSI-Low at the low X-ray tube voltage and the tomographic image CSI-High at the high X-ray tube voltage are image-reconstructed.

Then, the tomographic image CSI-Low at the low X-ray tube voltage is multiplied by a weighted addition coefficient w1 and the tomographic image CSI-High at the high X-ray tube voltage is multiplied by a weighted addition coefficient −w2, and a weight adding process is carried out along with a constant C1. The weighted addition coefficients w1 and w2 and the constant C1 are determined depending on atoms desired to be extracted, atoms desired to be emphasized, and atoms or regions desired to be eliminated on the display. Supposing that where it is desired to separate a calcium component (Ca component) constituting a bone or calcification, which is close to a CT value and a contrast agent (Iodine component) with iodine as a principal component, from each other, for example, the calcium component is eliminated on the display, i.e., a pixel value of the calcium component is set to 0, the Iodine component is extracted and displayed with being emphasized, whereby a tomographic image M-CSI corresponding to a distribution image of the contrast agent component is obtained.

Image quality such as image noise, spatial resolution, a slice thickness and the like are measured in relation to the tomographic image M-CSI. It is determined whether they are optimum by comparison with their index values. If not so, then a feedback for changing the condition for the image reconstruction is performed. That is, the control unit 37 adjusts the image reconstructing condition. Then, the control unit 37 adjusts the image filter, image reconstruction function and the like to image-reconstruct the tomographic image CSI-Low at the low X-ray tube voltage and the tomographic image CSI-High at the high X-ray tube voltage again. If the image quality such as the image noise, spatial resolution, slice thickness and the like are most suitable, then a tomographic image M-CSI subjected to the dual energy scan is displayed. Variables for the image reconstructing condition will be described in detail at Step C10 of FIG. 11.

Figure 11:
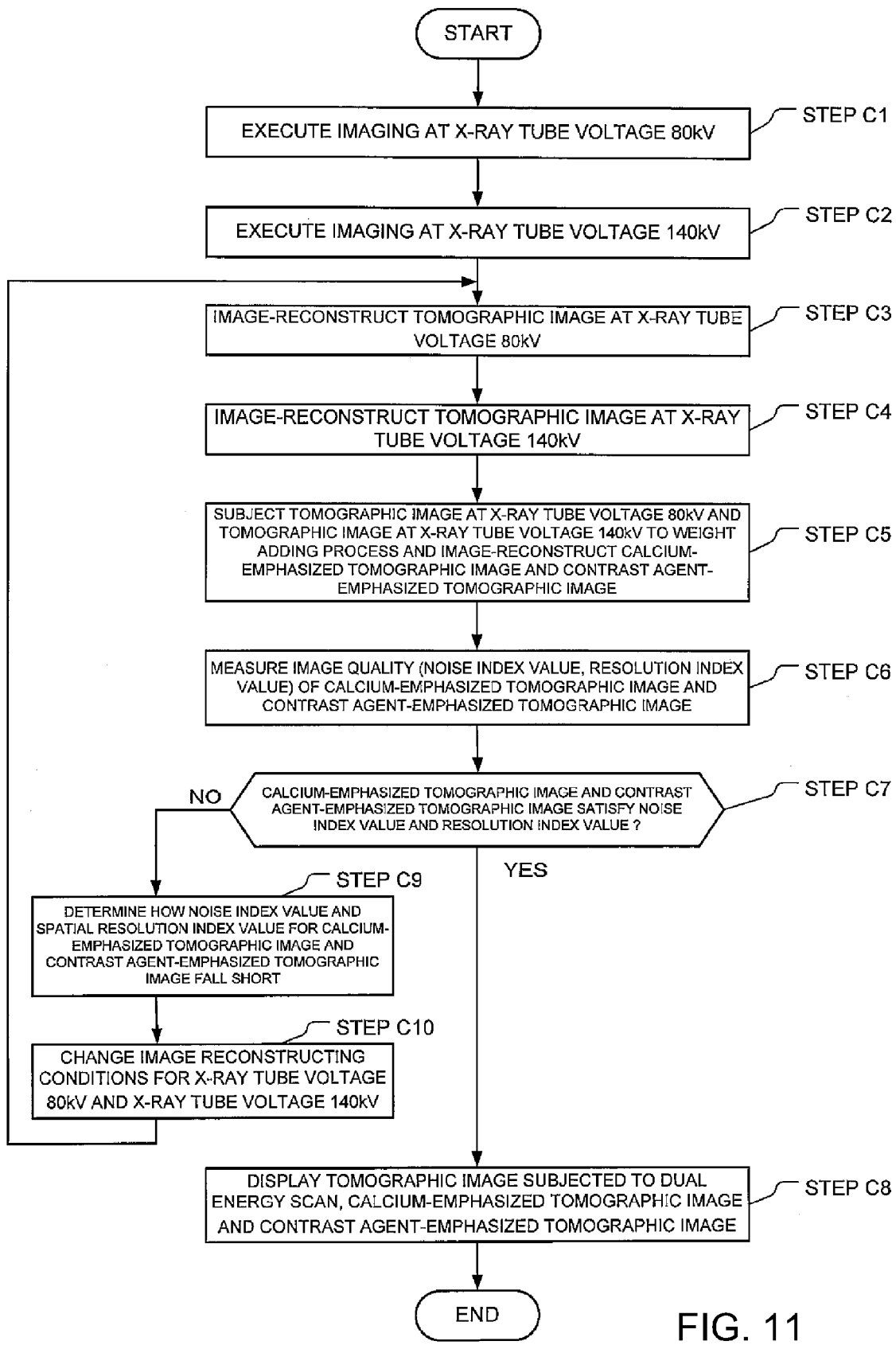
FIG. 11 is a flowchart illustrative of a tomographic image reconstructing method based on a dual energy scan, for feeding back and changing image reconstructing conditions for a tomographic image at a low X-ray tube voltage and a tomographic image at a high X-ray tube voltage.

A more specific flow of the outline of the dual energy scan shown in FIG. 10 is shown in FIG. 11. FIG. 11 is a flowchart illustrative of a tomographic image reconstructing method based on a dual energy scan, for feeding back and changing image reconstructing conditions for tomographic images at a plurality of X-ray tube voltages.

FIG. 11 is an embodiment in which since a tomographic image at an X-ray tube voltage 80 kV and a tomographic image at an X-ray tube voltage 140 kV by a dual energy scan do not satisfy sufficient image quality after their dual energy scans have been carried out, the tomographic images at the X-ray tube voltages 80 kV and 140 kV are image-reconstructed again under image reconstructing conditions changed by feeding back image reconstructing conditions for the tomographic images at the X-ray tube voltages 80 kV and 140 kV.

At Step C1, imaging or photography at an X-ray tube voltage 80 kV is performed.

At Step C2, imaging at an X-ray tube voltage 140 kV is performed.

At Step C3, each tomographic image at the X-ray tube voltage 80 kV is image-reconstructed.

At Step C4, each tomographic image at the X-ray tube voltage 140 kV is image-reconstructed.

At Step C5, the tomographic image at the X-ray tube voltage 80 kV and the tomographic image at the X-ray tube voltage 140 kV are subjected to a weight adding process, and a calcium-emphasized tomographic image and a contrast agent-emphasized tomographic image are image-reconstructed.

At Step C6, the image quality of each of the calcium-emphasized tomographic image and the contrast agent-emphasized tomographic image is measured. As an index value for the image quality, there is known a noise index value or a resolution index value. As to the noise index value, a standard deviation sd of each pixel of a tomographic image is generally used as the index value. As to the resolution index value, an MTF (Modulation Transfer Function) for an xy plane corresponding to one lying within a tomographic image of a wire phantom placed in a z direction, an MTF of a slit phantom placed in an xy plane corresponding to a tomographic image plane, a standard deviation sd, etc. are used as the index values.

At step C7, it is determined whether the calcium-emphasized tomographic image and the contrast agent-emphasized tomographic image satisfy the noise index value and the resolution index value. If the answer is found to be YES, then the flowchart proceeds to Step C8. If the answer is found to be NO, then the flowchart returns to Step C3.

At Step C8, the calcium-emphasized tomographic image, the contrast agent-emphasized tomographic image and the like each corresponding to a tomographic image M-CSI subjected to the dual energy scan are displayed.

At Step C9, it is determined how the noise index values and spatial resolution index values of the calcium-emphasized tomographic image and the contrast agent-emphasized tomographic image fall short.

At Step C10, image reconstructing conditions at the X-ray tube voltage 80 kV and X-ray tube voltage 140 kV are changed.

Conditions for image reconstruction. When the noise index value falls short upon changing the image reconstructing condition for each tomographic image at the X-ray tube voltage 80 kV or each tomographic image at the X-ray tube voltage 140 kV at Step C10, a reconstruction function for emphasizing a low frequency region or domain without emphasizing a high frequency region or domain is used as a reconstruction function.

As an image filter, an image filter for emphasizing the low frequency domain, an image filter for suppressing a high frequency domain selectively, or the like is used. While 512× 512 pixels are normally used as an image reconstruction matrix, a reduction in image reconstruction matrix number also produces an effect as in the case of 256×256 pixels in order to improve the noise index value. At this time, however, the average of 2×2 pixels in the conventional image reconstruction matrix 512×512 pixels needs to reach one pixel of the image reconstruction matrix 256×256 pixels. To this end, respective X-ray detector data corresponding to X-ray projection data used at the image reconstruction matrix 512×512 pixels are added two by two in a channel direction, and a backprojecting process is performed using the respective X-ray detector data in which the size in the channel direction, of an X-ray beam aperture becomes twice, thereby making it possible to sufficiently exert the effect of raising a noise index value with the image reconstruction matrix as the 256×256 pixels.

Figure 12:
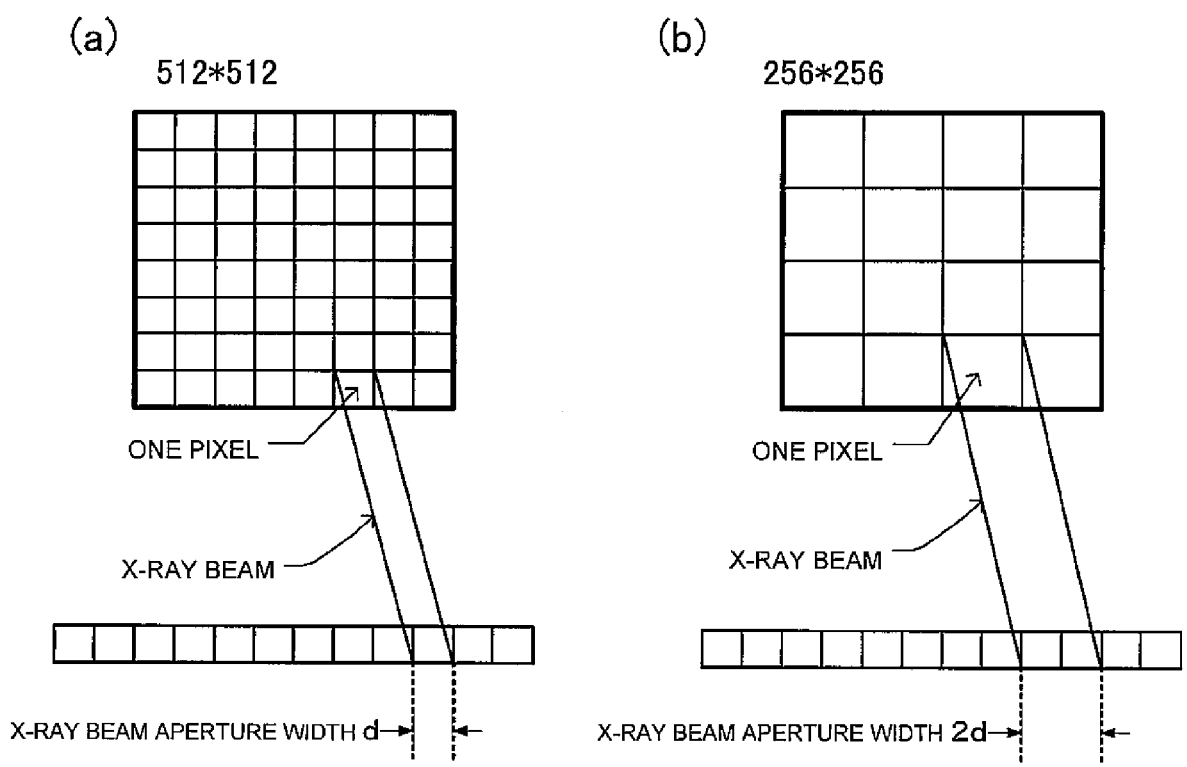
FIGS. 12(a) and 12(b) show shows control on X-ray beam aperture widths by image reconstruction matrix numbers.

FIG. 12 show control of X-ray beam aperture widths by image reconstruction matrix numbers. Now assume that the sizes of the multi-row X-ray detector 24 and the image reconstruction matrix are so designed that the width of one channel of the multi-row X-ray detector 24, i.e., a channel-direction X-ray beam aperture width becomes d in accordance with the size of one pixel of a 512×512 image reconstruction matrix. Considering a 256×256 image reconstruction matrix in this case, the size of one pixel of the 256×256 image reconstruction matrix results in a width corresponding to two channels of the multi-row X-ray detector 24, i.e., a channel-direction X-ray beam aperture width 2D as shown in FIG. 12. Therefore, it is necessary to effect a backprojecting process on X-ray detector data of the multi-row X-ray detector 24 after a process for bundling two channels into one data in the case of the 256×256 image reconstruction matrix. Alternatively, it is necessary to perform the backprojecting process after convolution of (½, ½) spatial filters in the channel direction. Controlling the size of one pixel of the image reconstruction matrix and the size of the channel width of the X-ray detector data, i.e., the X-ray beam aperture width as viewed in the channel direction in such a manner that they are approximately identical in size as described above, yields the optimization of image noise in the image reconstructing process.

In order to improve the noise index value by adjusting the coefficient of a z filter, the slice thickness is slightly increased in the z direction to improve the noise index value. When a $\frac{1}{10}$ width FWTM (Full Width Tenth Maximum) is expanded without expanding a full width half maximum FWHM if possible, the noise index value can be improved without having the feeling so much that the slice thickness increases visually.

As a space filter for X-ray projection data space, a space filter for emphasizing a low frequency without emphasizing a high frequency in the X-ray projection data space expanded in channel, row and view directions may be used. When the low frequency is excessively emphasized only in the channel direction in this case, spatial resolution of an xy plane is deteriorated. Alternatively, when the low frequency is excessively emphasized only in the row direction, spatial resolution in the z direction is deteriorated. Therefore, X-ray projection data space filters may be caused to act selectively while adapting to the characteristics of data in the X-ray projection data space and data adjacent thereto, for example, as in the case of execution of a stronger low-frequency emphasis in the z direction where a change due to a structure exists in the channel direction and a change due to the structure does not exist in the z direction, and execution of a stronger low-frequency emphasis in the channel direction where a change due to the structure exists in the z direction and a change due to the structure does not exist in the channel direction.

At Step C10, target values for image quality set every tomographic image at plural X-ray tube voltages, e.g., targeted noise index values can be defined in the following manner in such a way that the final tomographic image subjected to the dual energy scan coincides with a targeted index value of image quality.

It is first determined at what mA of X-ray tube current each of tomographic images at a plurality of X-ray tube voltages should be made equivalent to image quality on the basis of the standard deviations sd of the tomographic images subjected to the dual energy scan under the respective imaging conditions for the phantom measured data shown in FIG. 9(a). At least one of the reconstruction function, image filter, image reconstruction matrix number, z filter, and space filter for the X-ray projection data space is adjusted in such a manner that the tomographic image reaches the image quality corresponding to the X-ray tube current. Incidentally, at this time, there might be a case wherein it is necessary to well sort targets for noise index values to the tomographic images at the respective X-ray tube voltages in such a way as to fall within X-ray tube current values in an outputtable range of the X-ray generator.

Thus, using the image reconstructing conditions for the tomographic image CSI-Low at the low X-ray tube voltage and the tomographic image CSI-High at the high X-ray tube voltage, each tomographic image indicative of the X-ray tube voltage-dependent information, i.e., each tomographic image subjected to the so-called dual energy scan is adjusted in accordance with the target value of image quality. That is, the image quality of each image-reconstructed tomographic image subjected to the dual energy scan is measured, and the image reconstructing conditions for the tomographic images at the plural X-ray tube voltages are fed back in such a way that the measured image quality coincides with the target value of the image quality of the final tomographic subjected to the dual energy scan, whereby the image quality of each of the tomographic images at the plurality of X-ray tube voltages can be readjusted.

Incidentally, in the above embodiment, the image reconstructing conditions for each tomographic image at the X-ray tube voltage 80 kV and each tomographic image at the X-ray tube voltage 140 kV are respectively changed to reconstruct the tomographic image at the X-ray tube voltage 80 kV and the tomographic image at the X-ray tube voltage 140 kV respectively and optimize the image quality of the dual energy image. When, however, image reconstruction is performed in projection space obtained by subjecting the projection data of the low X-ray tube voltage and the projection data of the high X-ray tube voltage to the weight adding process, the condition for image reconstruction in the projection space is changed to optimize the image quality of the dual energy image.

Second embodiment. The second embodiment shows an embodiment in which the imaging conditions for the plurality of X-ray tube voltage-based tomographic images are adjusted in such a manner that the index value corresponding to the target for image quality is given to each tomographic image subjected to the dual energy scan and its index value is satisfied.

Figure 13:
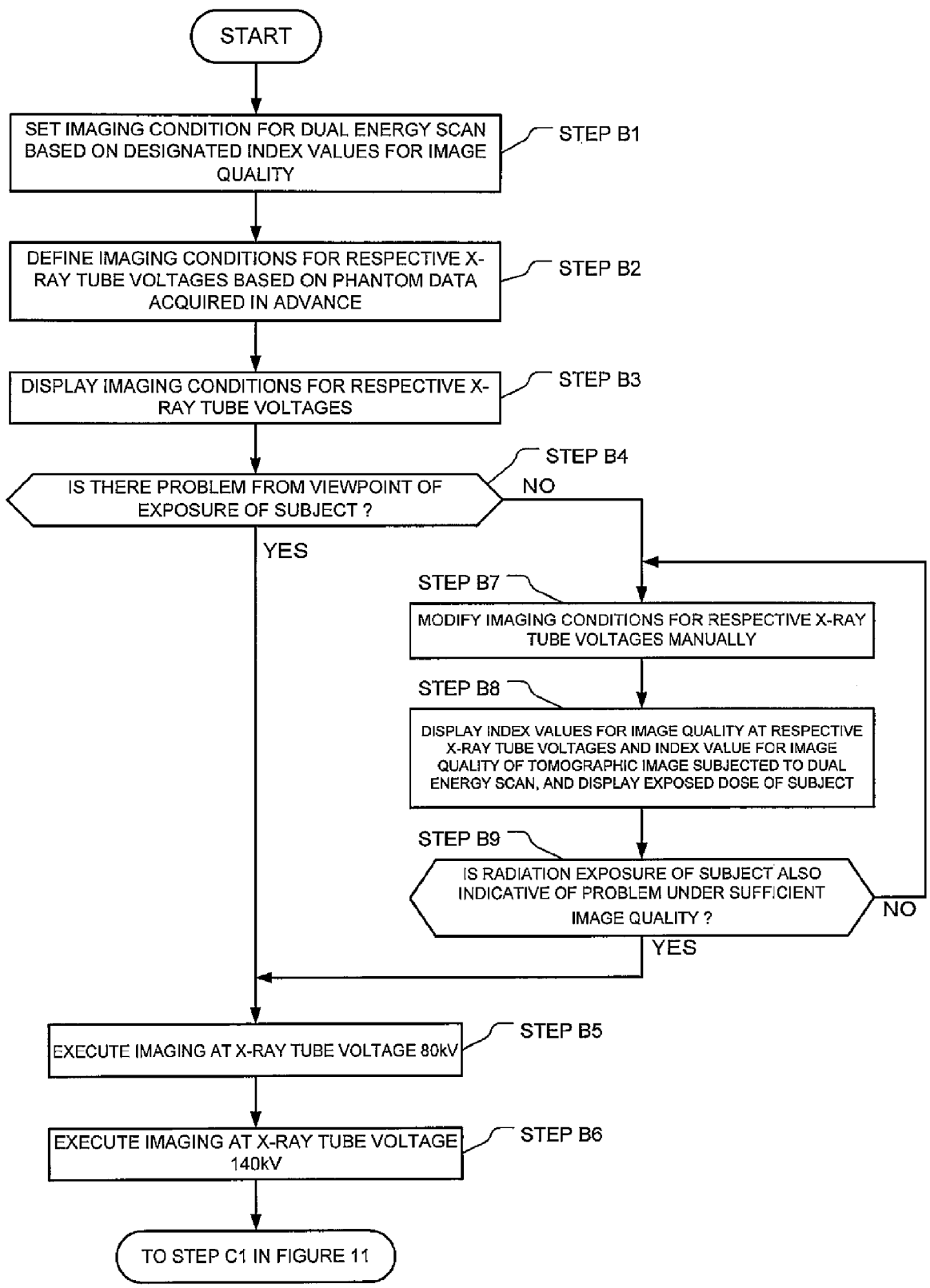
FIG. 13 is a flowchart showing tomographic image reconstruction for a dual energy scan based on designated index values for image quality.

FIG. 13 is a flowchart showing image reconstruction of each tomographic image subjected to a dual energy scan, based on designated index values for image quality.

At Step B1, an imaging condition for the dual energy scan is set based on the designated index values for image quality.

At Step B2, imaging conditions for respective X-ray tube voltages are set based on phantom data acquired in advance.

At Step B3, the imaging conditions for the respective X-ray tube voltages are displayed.

At Step B4, it is determined whether a problem arises from the viewpoint of subject's exposure. If the answer is found to be YES, then the flowchart proceeds to Step B5. If the answer is found to be NO, then the flowchart proceeds to Step B7.

At Step B5, imaging at an X-ray tube voltage 80 kV is performed.

At Step B6, imaging at an X-ray tube voltage 140 kV is performed.

Thereafter, the flowchart proceeds to Step C1 of FIG. 11. That is, when the corresponding tomographic image subjected to the dual energy scan does not satisfy a targeted index value for image quality, e.g., an image noise index value as described in the first embodiment, the image reconstructing condition is changed by the image reconstructing process in such a manner that the index value for image quality is satisfied, and the image reconstruction is carried out again.

At Step B7, the imaging conditions for the respective X-ray tube voltages are modified manually.

At Step B8, the index values for image quality at the respective X-ray tube voltages and the index value for image quality of each tomographic image subjected to the dual energy scan are displayed, and exposed dose of the subject is displayed.

At Step B9, it is judged whether the radiation exposure of the subject shows no problem either under sufficient image quality. If the answer is found to be YES, then the flowchart proceeds to Step B5. If the answer is found to be NO, then the flowchart returns to Step B7.

At Steps B1 to B4, and Steps B7 to B9, the imaging conditions for the dual energy scan are set based on the previously-designated index values for image quality. How CT's standard deviation sd corresponding to the image noise of the phantom changes when the X-ray tube current placed under the imaging condition at the high X-ray tube voltage changes with respect to the imaging conditions for the respective low X-ray tube voltages, is stored in the storage device 7 in advance every sizes of various phantoms and ratios w1/w2 of various weighted addition coefficients. The index values for image quality of the tomographic images at the plural X-ray tube voltages are assigned every tomographic images at the respective X-ray tube voltages from the index values for image quality of the final tomographic images subjected to the dual energy scan. If no particular restrictions are placed on the X-ray generator, then the image quality of each tomographic image at the low X-ray tube voltage and the image quality of each tomographic image at the high X-ray tube voltage are set approximately identical as much as possible.

Upon the photography of the subject, a profile area corresponding to an integral value of an X-ray penetration path length of the subject is found upon the scout image photography. Using imaging condition tables each based on the dual energy scan of phantoms each corresponding to a profile area approximately equal to the profile area of the subject, imaging conditions at a plurality of X-ray tube voltages for satisfying the targeted image-quality index values of the tomographic images subjected to the dual energy scan, e.g., noise index values, that is, an X-ray tube current value for a low X-ray tube voltage and an X-ray tube current value for a high X-ray tube voltage can be determined or defined. Incidentally, at this time, image noise of each tomographic image at the low X-ray tube voltage and image noise of each tomographic image at the high X-ray tube voltage may preferably be set approximately equal to each other.

Therefore, it is preferable to store a graph or table from which exposed dose of each tomographic image at the low X-ray tube voltage and exposed dose of each tomographic image at the high X-ray tube voltage are known, in the storage device 7 in advance. Further, the exposed dose of the tomographic image at the low X-ray tube voltage and the exposed dose of the tomographic image at the high X-ray tube voltage may be set approximately equal or may be made approximately identical in consideration of weighted addition coefficients.

Figure 14:
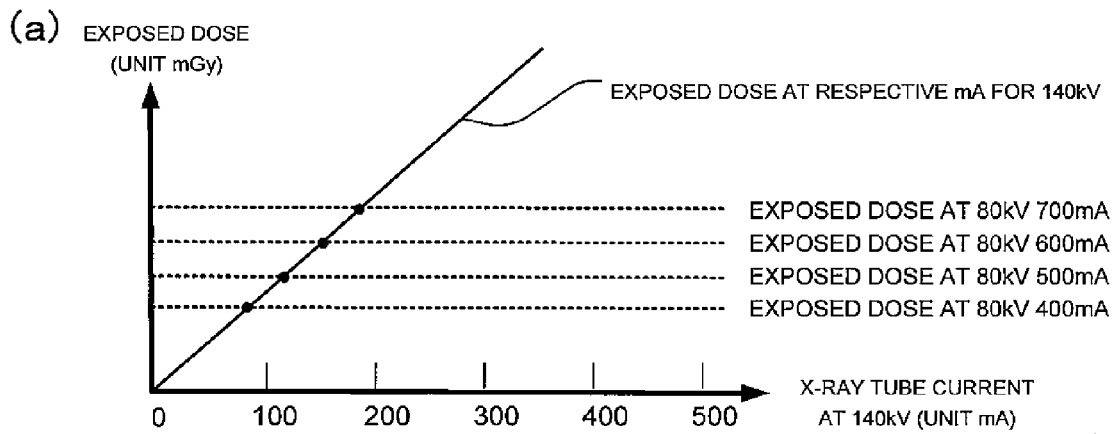
FIG. 14(a) is a diagram showing exposed dose at respective imaging conditions.
FIG. 14(b) is a flowchart for determining X-ray tube currents for respective X-ray tube voltages, based on a target image-quality index value for a tomographic image subjected to a dual energy scan.
Figure 14:
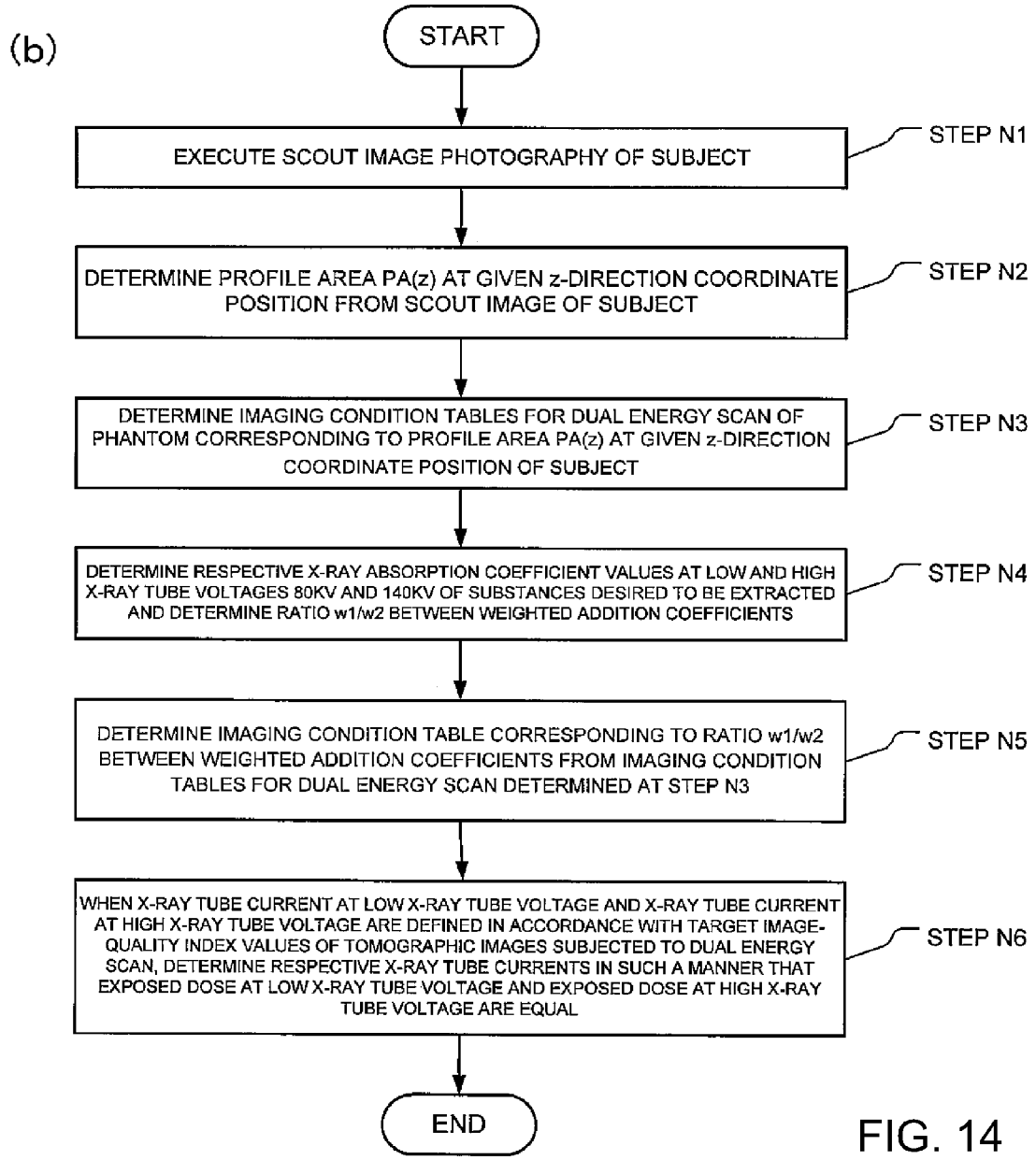

FIG. 14(a) is a graph showing exposed dose at respective imaging conditions. A flow of processing at this time is shown in FIG. 14(b).

At Step N1, scout image photography of a subject is executed.

At Step N2, a profile area PA(z) at a given z-direction coordinate position is determined from a scout image of the subject.

At Step N3, imaging condition tables for dual energy scanning of phantoms each corresponding to the profile area PA(z) at the given z-direction coordinate position of the subject are determined.

At Step N4, respective X-ray absorption coefficient values at X-ray tube voltages 80 kV and 140 kV, of substances desired to be extracted are determined and a ratio w1/w2 between weighted addition coefficients is determined.

At Step N5, an imaging condition table equivalent to the ratio w1/w2 is determined from the imaging condition tables for the dual energy scan determined at Step N3.

At Step N6, when an X-ray tube current at a low X-ray tube voltage and an X-ray tube current at a high X-ray tube voltage are determined or defined in accordance with target image-quality index values of tomographic images subjected to the dual energy scan, the respective X-ray tube currents are determined or defined in such a manner that exposed dose at the low X-ray tube voltage and exposed dose at the high X-ray tube voltage become equal to each other.

In the second embodiment, the imaging conditions for the tomographic images at the plural X-ray tube voltages and the image reconstructing conditions can be adjusted in the above-described manner such that the index values targeted for the image quality are given to the tomographic images subjected to the dual energy scan, and the index values for the image quality are satisfied.

Third embodiment. The third embodiment indicates an embodiment in which when the positions of the tomographic image at the low X-ray tube voltage and the tomographic image at the high X-ray tube voltage are displaced or shifted at the tomographic images subjected to the dual energy scan, and a mis-registration artifact is found in each tomographic image subjected to the dual energy scan, a registration or alignment correction is done, thereby optimizing the image quality of the tomographic image subjected to the dual energy scan to an index value for targeted image quality. A flow of its processing is shown in FIG. 15.

Figure 15A:
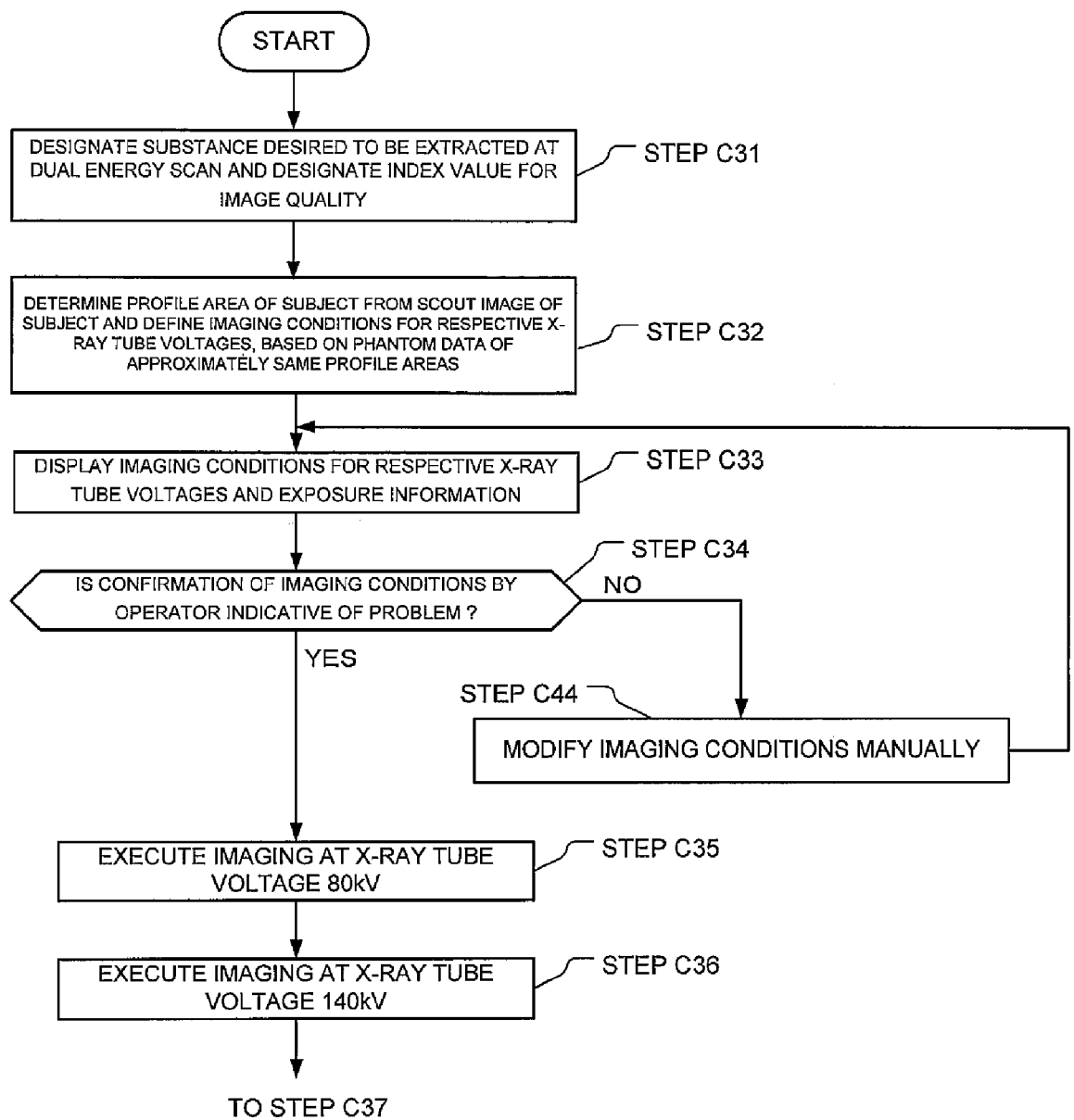
FIG. 15A is a flowchart for describing tomographic image reconstruction for a dual energy scan based on a designated image-quality index value.
Figure 15B:
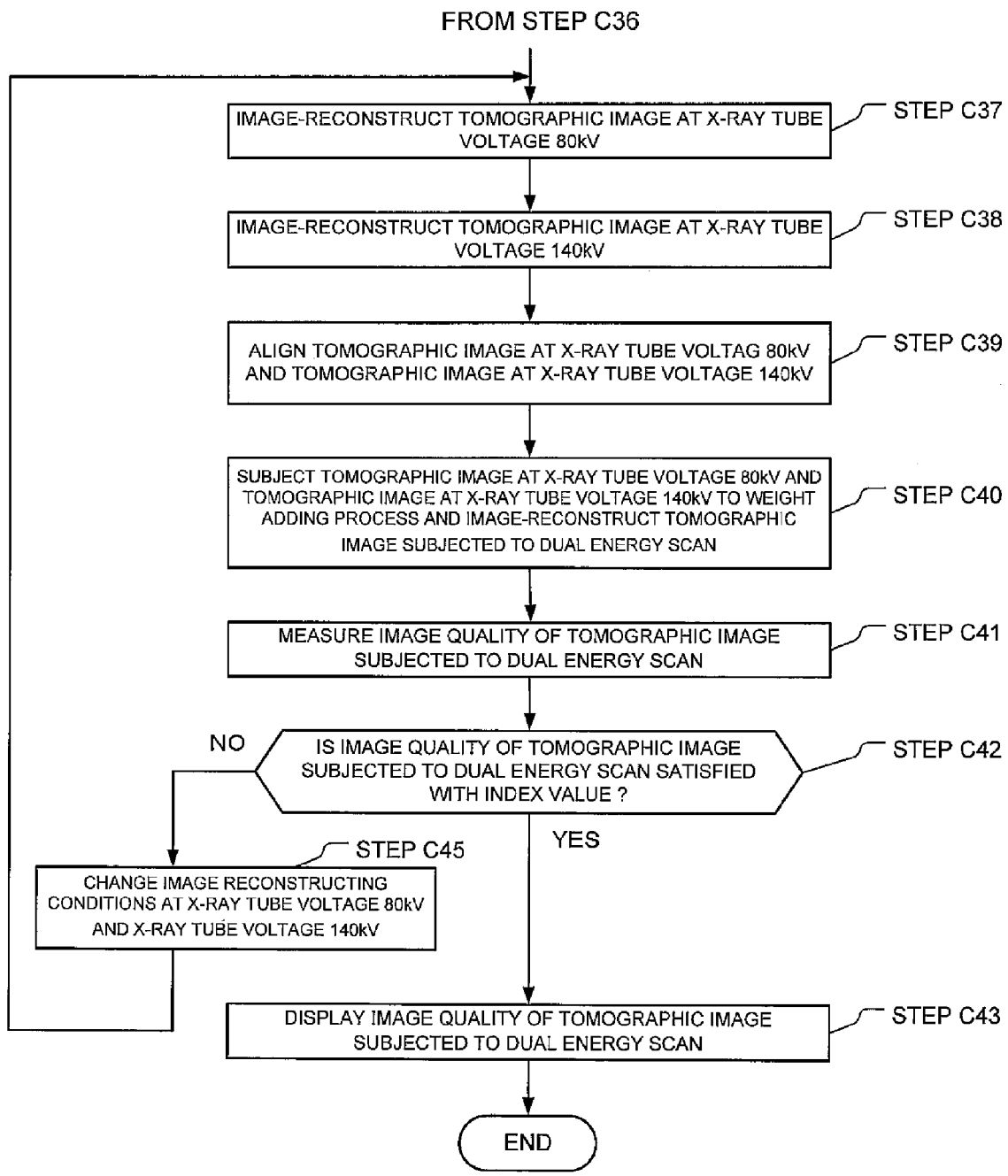
FIG. 15B is a flowchart following FIG. 15A.

FIG. 15 is a flowchart showing image reconstruction for a dual energy scan in which tomographic images are aligned.

At Step C31, a substance desired to be extracted upon a dual energy scan is designated, and an index value for image quality is designated. When it is desired to extract or emphasize a contrast agent, for example, a calcium component such as calcification, a bone or the like close to the contrast agent in CT value may be removed. When it is desired to extract the calcium component such as calcification, a bone or the like or emphasize the calcium component in reverse, the contrast agent close to the calcium component in CT value may be eliminated. When it is desired to extract a fat component or emphasize the fat component, a water content constituting soft tissues may be removed identically. When it is desired to extract a water content or emphasize the same in like manner, a fat content may be removed. Thus, the substance desired to be extracted and the substance desired to be removed are designated or specified and the corresponding imaging condition is set. Image noise, i.e., standard deviations sd of CT values at respective pixels are well used as index values for image quality.

At Step C32, each profile area of a subject is determined from a scout image of the subject. Imaging conditions for respective X-ray tube voltages are defined based on phantom data of approximately the same profile areas. In order to determine the profile area of the subject's scout image, the portion lying in the channel-direction range of the subject may be added to or integrated with respect to the X-ray projection data already subjected to the logarithmic transformation after the pre-process at Step P4 in the image reconstruction flowchart of FIG. 2.

At Step C33, the imaging conditions for the respective X-ray tube voltages and information about radiation exposure are displayed. A CTDI (CT Dose Index) and DLP (Dose Length Products) are normally displayed as the exposure information.

At Step C34, it is determined whether confirmation of imaging conditions by an operator presents a problem. If the answer is found to be YES, then the flowchart proceeds to Step C35. If the answer is found to be NO, then the flowchart proceeds to Step C44.

At Step C35, imaging at an X-ray tube voltage 80 kV is performed.

At Step C36, imaging at an X-ray tube voltage 140 kV is performed.

At Step C37, each tomographic image at the X-ray tube voltage 80 kV is image-reconstructed.

At Step C38, each tomographic image at the X-ray tube voltage 140 kV is image-reconstructed.

At Step C39, the tomographic image at the X-ray tube voltage 80 kV and the tomographic image at the X-ray tube voltage 140 kV are aligned with each other. This alignment will be described later using FIGS. 16 and 17.

At Step C40, the tomographic image at the X-ray tube voltage 80 kV and the tomographic image at the X-ray tube voltage 140 kV are subjected to a weight adding process to image-reconstruct each tomographic image subjected to the dual energy scan.

At Step C41, the image quality of each tomographic image subjected to the dual energy scan is measured.

At Step C42, it is determined whether the image quality of each tomographic image subjected to the dual energy scan satisfies an index value. If the answer is found to be YES, then the flowchart proceeds to Step C43. If the answer is found to be NO, then the flowchart proceeds to Step C45.

At Step C43, each tomographic image subjected to the dual energy scan is displayed.

At Step C44, the imaging conditions are modified or corrected manually and the flowchart returns to Step C33.

At Step C45, image reconstructing conditions for the tomographic images at the respective X-ray tube voltages are changed and the flowchart returns to Step C37.

At Step C31 to Step C34, and Step C44, such X-ray tube currents at the respective X-ray tube voltages that the index values for image quality, which are determined for the tomographic images subjected to the dual energy scan can be satisfied, are defined in a manner similar to the second embodiment, thereby determining imaging conditions. The operator is caused to confirm the imaging conditions at the X-ray tube voltages, which are determined at this time. If it is necessary to correct the imaging conditions from the viewpoint of subject's exposure or the like, then the operator modifies or corrects the imaging conditions manually.

At Step C35 to Step C43, and Step C45, when the finally-obtained tomographic image subjected to the dual energy scan does not satisfy a targeted index value for image quality, e.g., an image noise index value in a manner similar to the first and second embodiments, an image reconstructing process is performed on the X-ray projection data acquired at the plural X-ray tube voltages again, and the conditions for the image reconstructing process are changed such that the index values for image quality of the respective tomographic images at the plural X-ray tube voltages are satisfied, thereby satisfying the image quality of the tomographic images at the plural X-ray tube voltages. As a result, the image quality of the final tomographic image subjected to the dual energy scan can be satisfied.

Alignment of tomographic image at X-ray tube voltage 80 kV and tomographic image at X-ray tube voltage 140 kV.

Figure 16:
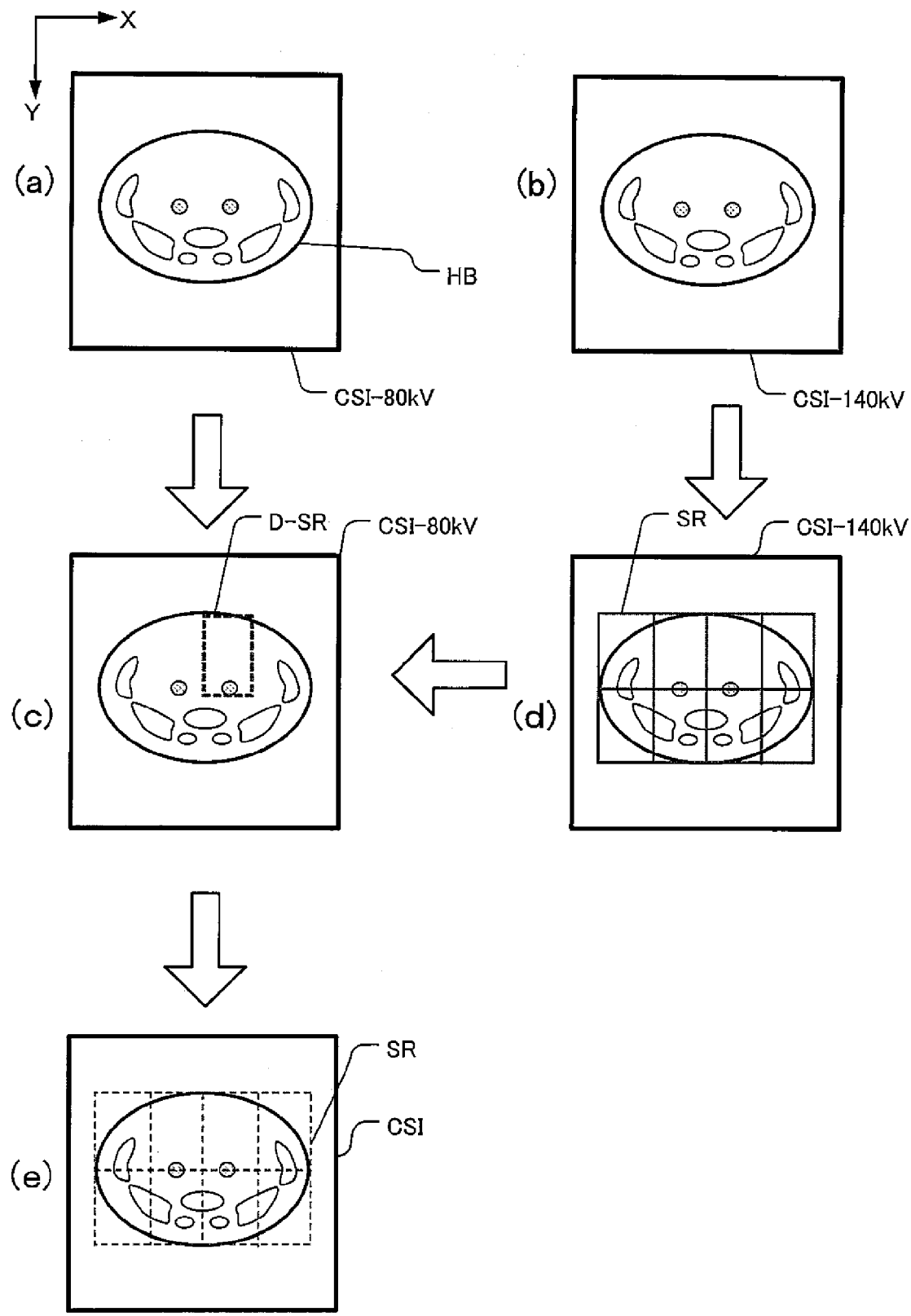
FIGS. 16(a), 16(b), 16(c), 16(d), and 16(e) are diagrams showing an outline of a process for performing alignment every divided area for a circumscribed rectangle SR.

FIG. 16 is a diagram showing the outline of a process for performing alignment every divided area for a circumscribed rectangle SR. This is a schematic diagram showing alignment of the tomographic image CSI-80 kV at the X-ray tube voltage 80 kV and the tomographic image CSI-140 kV at the X-ray tube voltage 140 kV both shown in Step C39.

FIG. 16(a) shows the tomographic image CSI-140 kV at the X-ray tube voltage 140 kV, and FIG. 16(b) shows the tomographic image CSI-140 kV at the X-ray tube voltage 140 kV. The tomographic image CSI-140 kV at the X-ray tube voltage 140 kV is extracted by performing a binarizing process or the like on the profile or contour of the subject as shown in FIG. 16(d). Then, the circumscribed rectangle SR including the profile is divided into eight, for example.

One of the divided circumscribed rectangles D-SR at the X-ray tube voltage 140 kV is aligned with the tomographic image CSI-80 kV at the X-ray tube voltage 80 kV as shown in FIG. 16(c). A correlation operation or computation is effected upon its alignment. Other divided circumscribed rectangles D-SR at the X-ray tube voltage 140 kV are also sequentially aligned with the tomographic image CSI-80 kV at the X-ray tube voltage 80 kV. Thus, the circumscribed rectangles D-SR at the X-ray tube voltage 140 kV, which are divided as shown in FIG. 16(e), are united with the tomographic image CSI-80 kV at the X-ray tube voltage 80 kV. A flow of above processing is shown in FIG. 17.

Figure 17:
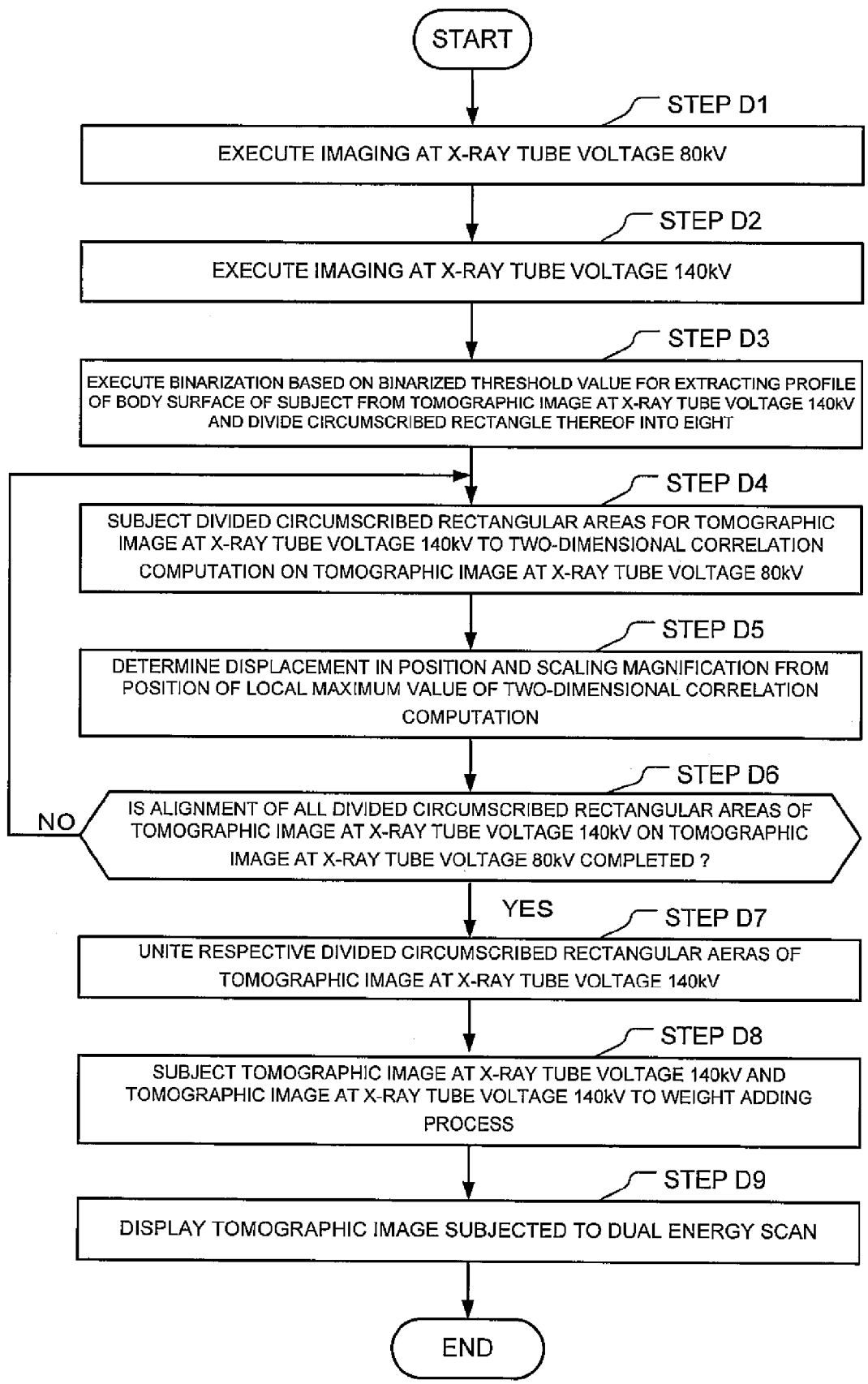
FIG. 17 is a flowchart showing image reconstruction for a dual energy scan where tomographic images are aligned.

FIG. 17 is a flowchart showing a dual energy scanning process in which alignment is performed every divided area for the circumscribed rectangle SR.

At Step D1, imaging at the X-ray tube voltage 80 kV is executed.

At Step D2, imaging at the X-ray tube voltage 140 kV is executed.

At Step D3, binarization is performed based on a binarized threshold value for extracting the profile or contour of a body surface of the subject from the tomographic image CSI-140 kV at the X-ray tube voltage 140 kV and the circumscribed rectangle SR is divided into eight. A flow of processing for determining eight-divided areas of the circumscribed rectangle SR of the subject at Step D3 will be described later using FIG. 18.

At Step D4, the areas for the divided circumscribed rectangles D-SR of the tomographic image CSI-140 kV at the X-ray tube voltage 140 kV are subjected to a two-dimensional correlation arithmetic operation or computation on the tomographic image CSI-80 kV at the X-ray tube voltage 80 kV. Then, a displacement quantity $\Delta x$ in an x direction and a displacement quantity $\Delta y$ in a y direction are determined from the position of the maximum value or local maximum value of the two-dimensional correlation computation, or the spread of its peak. A scaling magnification is determined from a full width half maximum FWHM indicative of the spread of the peak of the maximum value or local maximum value of the two-dimensional correlation computation. The details thereof will be explained later using FIG. 19.

At Step D5, a displacement or shift in position and a scaling magnification are determined from the position of the local maximum value of the two-dimensional correlation computation.

At Step D6, it is judged whether the alignment of all the areas for the divided circumscribed rectangles D-SR of the tomographic image CSI-140 kV at the X-ray tube voltage 140 kV on the tomographic image CSI-80 kV at the X-ray tube voltage 80 kV is completed. If the answer is found to be YES, then the flowchart proceeds to Step D7. If the answer is found to be NO, then the flowchart returns to Step D4.

At Step D7, the areas for the divided circumscribed rectangles D-SR of the tomographic image CSI-140 kV at the X-ray tube voltage 140 kV are united.

At Step D8, the tomographic image CSI-80 kV at the X-ray tube voltage 80 kV and the tomographic image CSI-140 kV at the X-ray tube voltage 140 kV are subjected to a weight adding process.

At Step D9, a tomographic image subjected to the dual energy scan is displayed.

Figure 18:
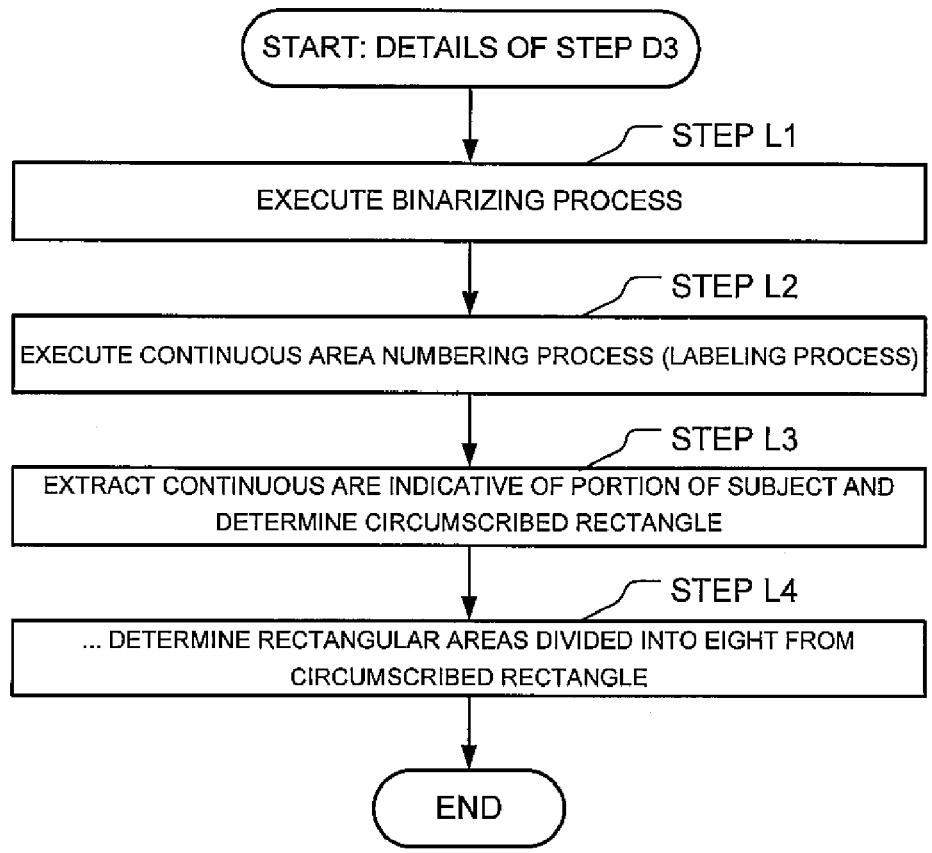
FIG. 18 is a flowchart for describing a process for determining areas obtained by dividing a circumscribed rectangle SR into eight.

Division of circumscribed rectangle SR of subject. FIG. 18 is a flowchart showing a process for determining 8-divided areas of the circumscribed rectangle SR of the subject and shows the details of Step D3.

At Step L1, a binarizing process is performed. Upon the binarizing process at Step L1, a binarized threshold value capable of performing separation between the subject and air may be taken to extract the profile or contour of the body surface of the subject. Therefore, values such as CT values: −50, −100 and the like may be used. Binarized images result in label regions numbered every continuous two-dimensional area by a continuous area numbering process (labeling process) at Step L2.

At Step L2, the continuous area numbering process (labeling process) is performed.

At Step L3, a continuous area indicative of each portion of the subject is extracted and a circumscribed rectangle SR is determined. At Step L3, one assumed to be a subject's continuous two-dimensional area, of the continuous two-dimensional area is extracted according to the area, the size of the circumscribed rectangle SR, the degree of a circular form, and the like.

At Step L4, rectangular areas D-SR divided into eight from the circumscribed rectangle SR are determined. At Step L4, the circumscribed rectangle SR can be divided into eight rectangular areas by a start point (xS, yS) and an end point (xS+Lx, yS+Ly) of the circumscribed rectangle SR of the continuous two-dimensional area of the subject extracted at Step L3.

Two-dimensional correlation computation. The two-dimensional correlation computation at Step D4 in FIG. 17 will be explained.

Figure 19:
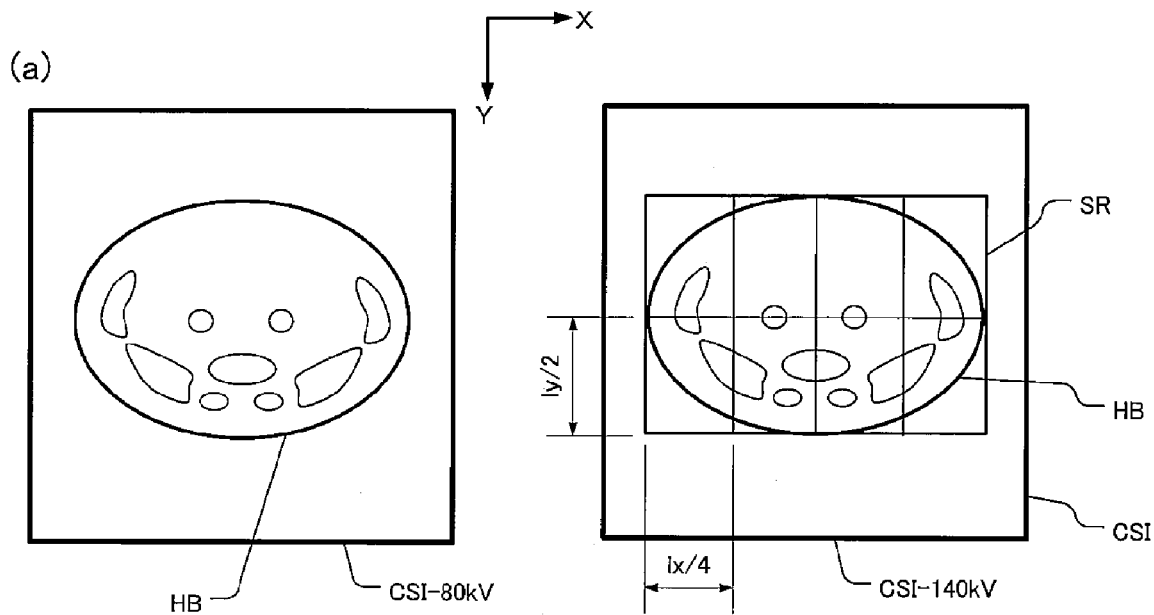
FIGS. 19(a) and 19(b) are diagrams showing an outline of a process for performing alignment by a two-dimensional correlation operation.
Figure 19:
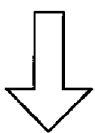
Figure 19:
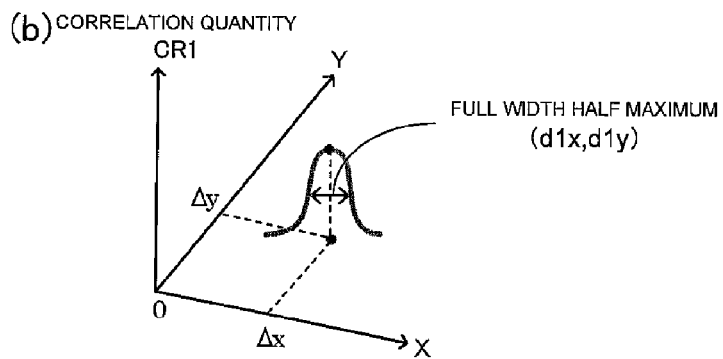

FIG. 19 is a diagram showing the outline of a process of alignment by the two-dimensional correlation computation. A tomographic image CSI-80 kV at an X-ray tube voltage 80 kV and a tomographic image CSI-140 kV at an X-ray tube voltage 140 kV, which is subjected to rectangular division, are shown in FIG. 19(a). One example of a change in correlation quantity CR1 (x, y) is shown in FIG. 19(b).

Assuming that respective pixel values of the tomographic image on the divided circumscribed rectangle SR at the X-ray tube voltage 140 kV are defined as g140(x, y), and respective pixel values of the tomographic image CSI-80 kV at the X-ray tube voltage 80 kV are defined as g80(x, y), a correlation quantity CR1(x, y) obtained by effecting the two-dimensional correlation computation on the areas for the circumscribed rectangle SR of the tomographic image CSI-140 kV at the X-ray tube voltage 140 kV on the tomographic image CSI-80 kV at the X-ray tube voltage 80 kV is expressed as shown below (Equation 13). However, the area for the tomographic image at the X-ray tube voltage 140 kV is assumed to be Ar140, and the area for the tomographic image at the X-ray tube voltage 80 kV is assumed to be Ar80.

Equation 13

$$CR1(x, y) = \frac{\int\int_{Ar80} g140(x, y) \cdot g(x-s, y-t) ds dt}{(\int\int_{Ar140} g140(x, y) dx dy)(\int\int_{Ar80} g80(x, y) dx dy)}. \qquad (13)$$

In FIG. 19(b), the correlation quantity CR1(x, y) takes the peak of a local maximum value at a position shifted or displaced by ($\Delta x$, $\Delta y$) from the origin 0 of the xy plane. A full width half maximum FWHM of its peak takes D1x in an x direction and D1y in a y direction.

$\Delta x$ and $\Delta y$ shown in FIG. 19(b) indicate a divided rectangular area of the tomographic image CSI-140 kV at the X-ray tube voltage 140 kV, and a displacement quantity of the tomographic image CSI-80 kV at the X-ray tube voltage 80 kV. A scaling magnification in the x direction and a scaling magnification in the y direction are respectively determined from the full width half maximum of the peak as shown below (Equation 14). Incidentally, Lx and Ly in the following equations respectively correspond to the length of the side in the x direction of the divided rectangular area and the length of the side in the y direction thereof.

Equation 14 (14)

$$r1x = \frac{lx + d1x}{lx}$$

$$r1y = \frac{ly + d1y}{ly}.$$

The x and y coordinates of the rectangular area g140(x, y) of the tomographic image at the X-ray tube voltage 140 kV are coordinate-transformed into new coordinates X and Y by these scaling magnifications r1x and r1y and the displacement quantities ($\Delta x$, $\Delta y$) in accordance with the following (Equation 15). Consequently, the rectangular area of the tomographic image CSI-140 kV at the X-ray tube voltage 140 kV can be aligned with the corresponding pixel values g(x, y) of the tomographic image at the X-ray tube voltage 80 kV. However, (xC, yC) indicates the center coordinates of the rectangular area of the tomographic image CSI-140 kV at the X-ray tube voltage 140 kV.

Equation 15 (15)

$$\begin{bmatrix} X - xc \\ Y - yc \end{bmatrix} = \left[ \begin{bmatrix} 1 + r1x & 0 \\ 0 & 1 + r1y \end{bmatrix} \begin{bmatrix} x - xc \\ y - yc \end{bmatrix} + \begin{bmatrix} \Delta x \\ \Delta y \end{bmatrix} \right]$$

Incidentally, at this time, although the scaling magnification r1x in the x direction and the scaling magnification r1y in the y direction are defined like the (Equation 14), the scale-up magnifications in the x and y directions may be multiplied by correction coefficients kx and ky due to the degree of the spread of the peak of the two-dimensional correlation computation depending on the image quality of each tomographic image such that the scale-up magnification in the x direction is defined as kx·r1x and the scale-up magnification in the y direction is defined as ky·r1y. Therefore, if the correction coefficients kx and ky are required depending on the image quality of each tomographic image, then the scale-up magnifications may be multiplied by the correction coefficients as described above. Incidentally, the correction coefficients kx and ky are expected to reach a value approximately close to 1, which corresponds to a value lying within a range of (0, 2). Incidentally, although the tomographic image CSI-140 kV at the X-ray tube voltage 140 kV is divided into the eight rectangular areas corresponding to the two division in the x direction and the four division in the y direction and aligned with the tomographic image CSI-80 kV at the X-ray tube voltage 80 kV in the present embodiment, the tomographic image CSI-80 kV at the X-ray tube voltage 80 kV may be divided and aligned with the tomographic image CSI-140 kV at the X-ray tube voltage 140 kV.

It is not necessary to set the number of divisions to eight. Even though the number of divisions is changed depending on a matrix size of each tomographic image, its image quality and the like, a similar effect can be obtained. Although all values lying in the CT-value range are used in the two-dimensional correlation computation, a similar effect can be obtained even though only some values in the CT-value range, e.g., only values greater than the CT value 0 are used in the two-dimensional correlation computation.

Figure 20:
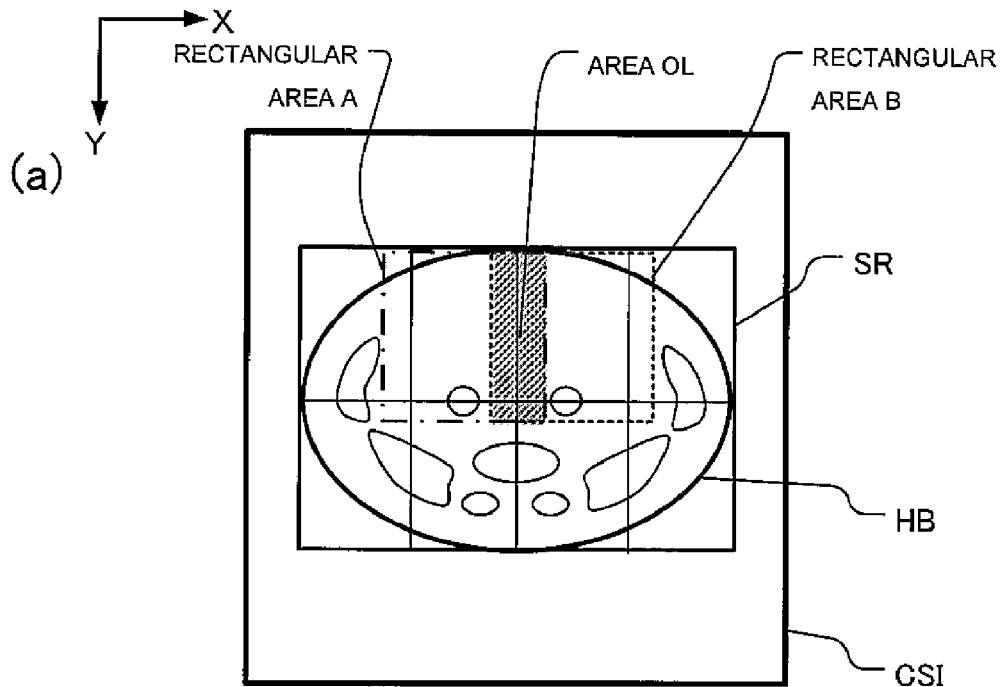
FIG. 20(a) is a diagram showing overlapped areas for a circumscribed rectangle SR.
FIG. 20(b) is a diagram showing weighted addition coefficients at overlapped sector areas.
Figure 20:
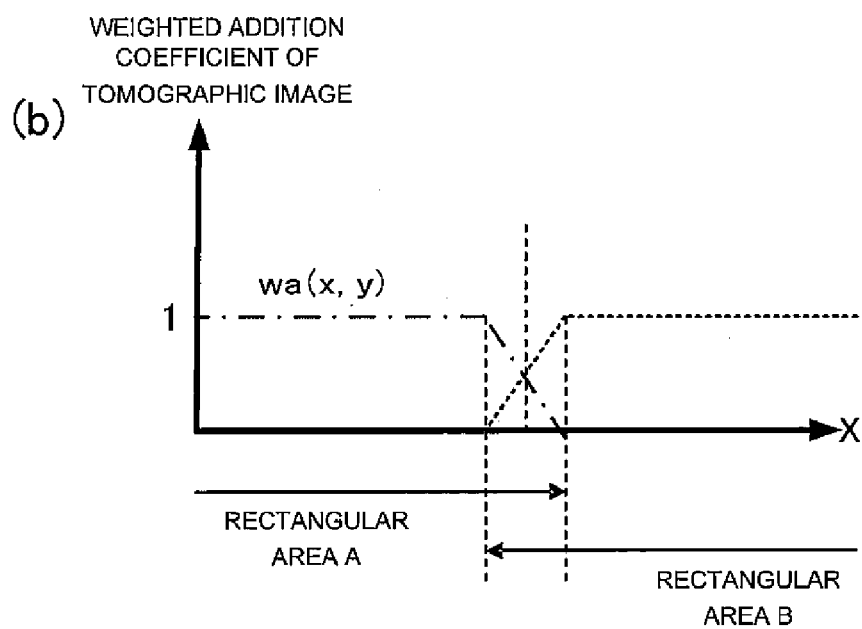

FIG. 20 is a diagram showing a case in which circumscribed rectangular areas are caused to overlap.

At Step D4 to Step D7 in FIG. 17, the areas for the eight-divided rectangles D-SR of the tomographic image at the X-ray tube voltage 140 kV are united. There is, however, a case in which discontinuous artifacts occur in the united boundary line and the united tomographic images at the junction portion are not joined continuously. In order to avoid it, the respective divided rectangular areas of the tomographic image are set to larger areas as shown in FIG. 20(a) and their alignment process may be carried out. As indicated by a rectangular area A and a rectangular area B in FIG. 20(a) by way of example, their alignment process is performed while they are being caused to overlap each other. That is, the process of aligning the rectangular areas for the tomographic image at the X-ray tube voltage 140 kV in the rectangular areas A and B is effected on both of the enlarged rectangular areas A and B.

At the boundary portion between the so-processed rectangular areas A and B, such weighted addition coefficients wa(x, y) and wb(x, y) as shown in FIG. 20(b) are applied to perform a weight adding process. The sum of the weighted addition coefficients wa(x, y) and wb(x, y) is always taken as "1" and held constant as expressed in the following equation:

$$wa(x,y)+wb(x,y)=1$$

By performing the weight addition process of the weighted addition coefficients wa(x, y) and wb(x, y) on the eight divided rectangular areas, the aligned tomographic images at the X-ray tube voltage 140 kV are joined continuously and smoothly. Although the linear weighted addition coefficients are used in FIG. 20(b), multidimensional and polynomial weighted addition coefficients that change smoother may be used.

Fourth embodiment. The fourth embodiment is an embodiment illustrative of optimization of a shift or displacement in a tomographic-image plane direction, i.e., a displacement in xy plane upon a three-dimensional display or an MPR display of a tomographic image indicative of X-ray tube voltage information, a tomographic image subjected to a dual energy scan or tomographic images at a plurality of X-ray tube voltages. That is, the fourth embodiment indicates an embodiment in which when a displacement in xy plane is detected, displacements in tomographic images at a plurality of X-ray tube voltages are corrected, thereby optimizing the image quality of each tomographic image subjected to a dual energy scan and the image quality of a three-dimensional display image and/or MPR display image.

When a tomographic image CSI-Low at a low X-ray tube voltage and a tomographic image CSI-High at a high X-ray tube voltage are photographed by a conventional scan or a cine scan in particular, the positions of the tomographic images lying within the xy plane at the conventional scan or cine scan might be shifted or displaced every z-direction coordinate position. At this time, an effective tomographic image alignment correction and a dual energy scanning method reduced in mis-registration artifact are adopted.

Figure 21:
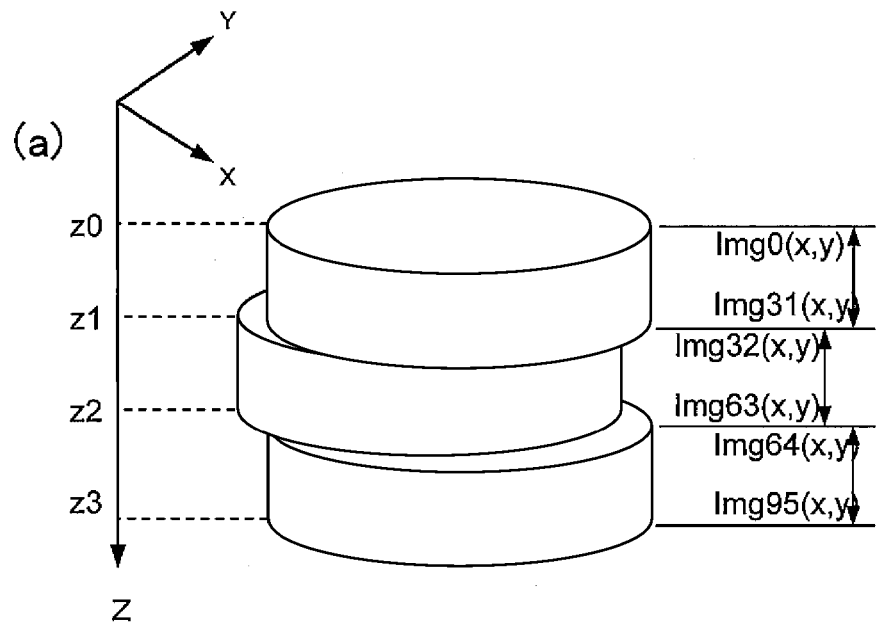
FIG. 21(a) is a diagram showing a three-dimensional display of tomographic images displaced within an xy plane at a conventional scan or a cine scan.
FIG. 21(b) is a diagram showing a display in which the tomographic images displaced within the xy plane at the conventional scan or cine scan are reprojected on the xy plane.
Figure 21:
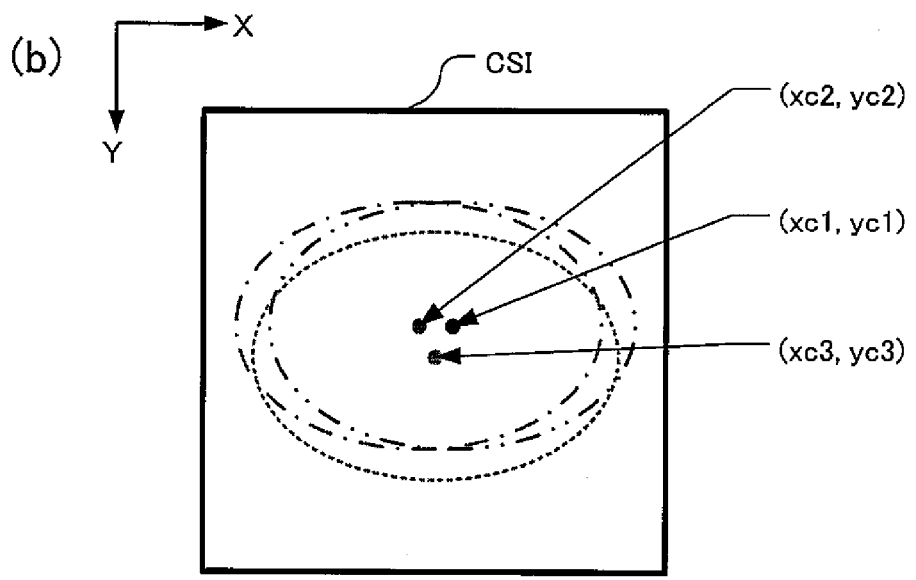

FIG. 21 is a diagram for describing displacements in the positions of tomographic images lying within an xy plane at the conventional scan or cine scan.

There are cases where when the conventional scan or cine scan is carried out three times over a range of a z-direction coordinate (z0, z1), a range of a z-direction coordinate (z1, z2) and a range of a z-direction coordinate (z2, z3) as shown in FIG. 21(a) by way of example, the positions in xy plane are shifted or displaced during the respective conventional scans or cine scans and thereby tomographic images are not made continuous as viewed in a z direction. In the case of the dual energy scan, the position in the xy plane, of each tomographic image at an X-ray tube voltage 80 kV and the position in the xy plane, of each tomographic image at an X-ray tube voltage 140 kV might be displaced.

The number of tomographic images photographed by a conventional scan or a cine scan at, for example, a first z-direction coordinate position is 32. They are assumed to be Img0(x, y) through Img31(x, y). The number of tomographic images photographed by a conventional scan or a cine scan at, for example, a second z-direction coordinate position is also 32. They are assumed to be Img32(x, y) through Img63(x, y). The number of tomographic images photographed by a conventional scan or a cine scan at, for example, a third z-direction coordinate position is also 32. They are assumed to be Img64(x, y) through Img95(x, y).

When the center positions of conventional scans or cine scans at the respective z-direction coordinate positions are defined below at this time, the center positions of tomographic images photographed by the conventional scans or cine scans at the respective z-direction coordinate positions are shifted or displaced even in the case of ones identical in shape as viewed in the z direction.

When the tomographic images are reprojection-displayed in the xy plane direction, they are represented as shown in FIG. 21(b). The center coordinate positions of the tomographic images Img0(x, y) through Img31(x, y) obtained by the conventional scan or cine scan at the first z-direction coordinate position in the range of the z-direction coordinate position (z0, z1) are assumed to be (xc1, yc1). The center coordinate positions of the tomographic images Img32(x, y) through Img63(x, y) obtained by the conventional scan or cine scan at the second z-direction coordinate position in the range of the z-direction coordinate position (z1, z2) are assumed to be (xc2, yc2). The center coordinate positions of the tomographic images Img64(x, y) through Img95(x, y) obtained by the conventional scan or cine scan at the third z-direction coordinate position in the range of the z-direction coordinate position (z2, z3) are assumed to be (xc3, yc3).

The respective (xc1, yc1), (xc2, yc2) and (xc3, yc3) are expressed as follows (Equation 16). However, an image matrix size of each tomographic image is assumed to be N×N pixels.

Equation 16 (16)

$$(xc1, yc1) \left[ \frac{1}{32} \sum_{i=0}^{31} \sum_{y=0}^{N-1} \sum_{x=0}^{N-1} x \cdot \mathrm{Img}i(x, y), \right.$$

$$\left. \frac{1}{32} \sum_{i=0}^{31} \sum_{y=0}^{N-1} \sum_{x=0}^{N-1} y \cdot \mathrm{Img}i(x, y) \right]$$

$$(xc2, yc2) = \left[ \frac{1}{32} \sum_{i=32}^{63} \sum_{y=0}^{N-1} \sum_{x=0}^{N-1} x \cdot \mathrm{Img}i(x, y), \right.$$

$$\left. \frac{1}{32} \sum_{i=32}^{63} \sum_{y=0}^{N-1} \sum_{x=0}^{N-1} y \cdot \mathrm{Img}i(x, y) \right]$$

$$(xc3, yc3) = \left[ \frac{1}{32} \sum_{i=64}^{95} \sum_{y=0}^{N-1} \sum_{x=0}^{N-1} x \cdot \mathrm{Img}i(x, y), \right.$$

$$\left. \frac{1}{32} \sum_{i=64}^{95} \sum_{y=0}^{N-1} \sum_{x=0}^{N-1} y \cdot \mathrm{Img}i(x, y) \right]$$

In the case of subjects identical in shape as viewed in the z direction or subjects approximately identical in shape, the center positions of tomographic images at second and third conventional scans or cine scans are caused to coincide with the center position of a tomographic image at a first conventional scan or cine scan. That is, the tomographic image at the second conventional scan or cine scan is shifted or displaced in accordance with vectors (xc1-xc2, yc1-yc2) without moving the tomographic image at the first conventional scan or cine scan. Further, the tomographic image at the third conventional scan or cine scan is shifted in accordance with vectors (xc1-xc3, yc1-yc3). Thus, the tomographic images displaced in the positions thereof in the xy plane can be aligned by the above tomographic image alignment correction at the conventional scans or cine scans taken every z-direction coordinate position. There is also known a position correcting method for performing a position correction so as to eliminate displacements between tomographic images at a z-direction boundary at conventional sans or cine scans for respective z-direction coordinate positions where a region greatly changed in shape as viewed in the z direction is photographed or a subject greatly changed in shape as viewed in the z direction is photographed.

Figure 22:
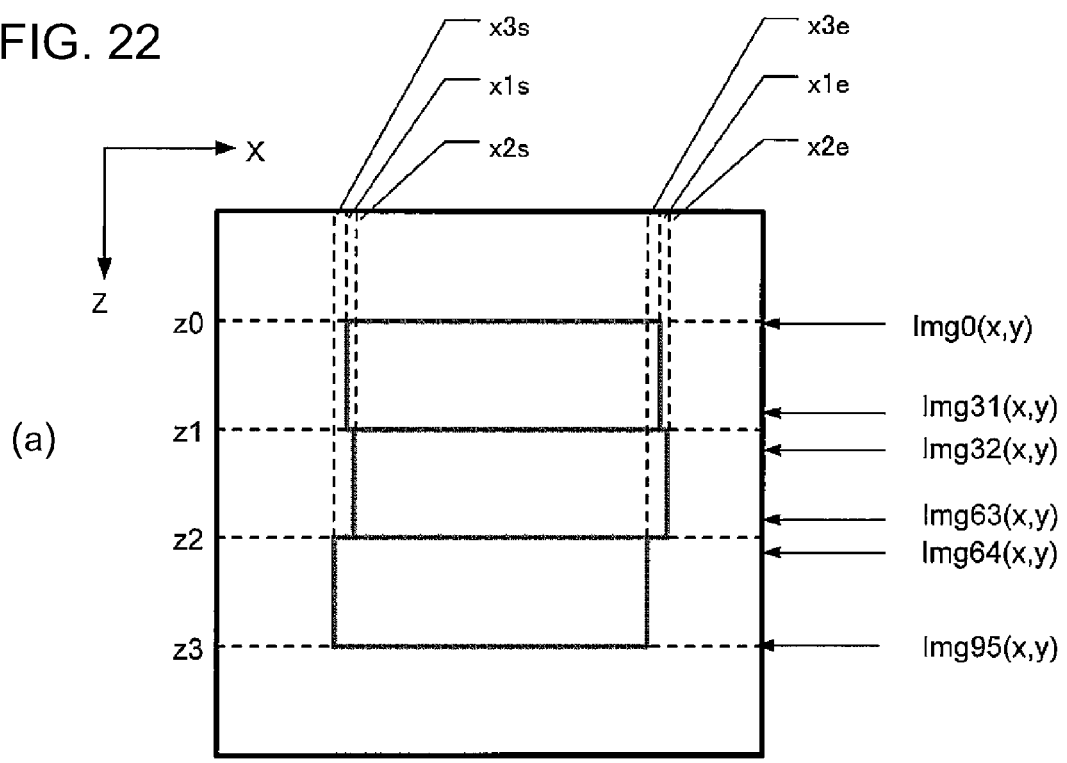
FIG. 22(a) is a diagram showing an xz-plane MPR image.
FIG. 22(b) is a diagram showing a yz-plane MPR image.
Figure 22:
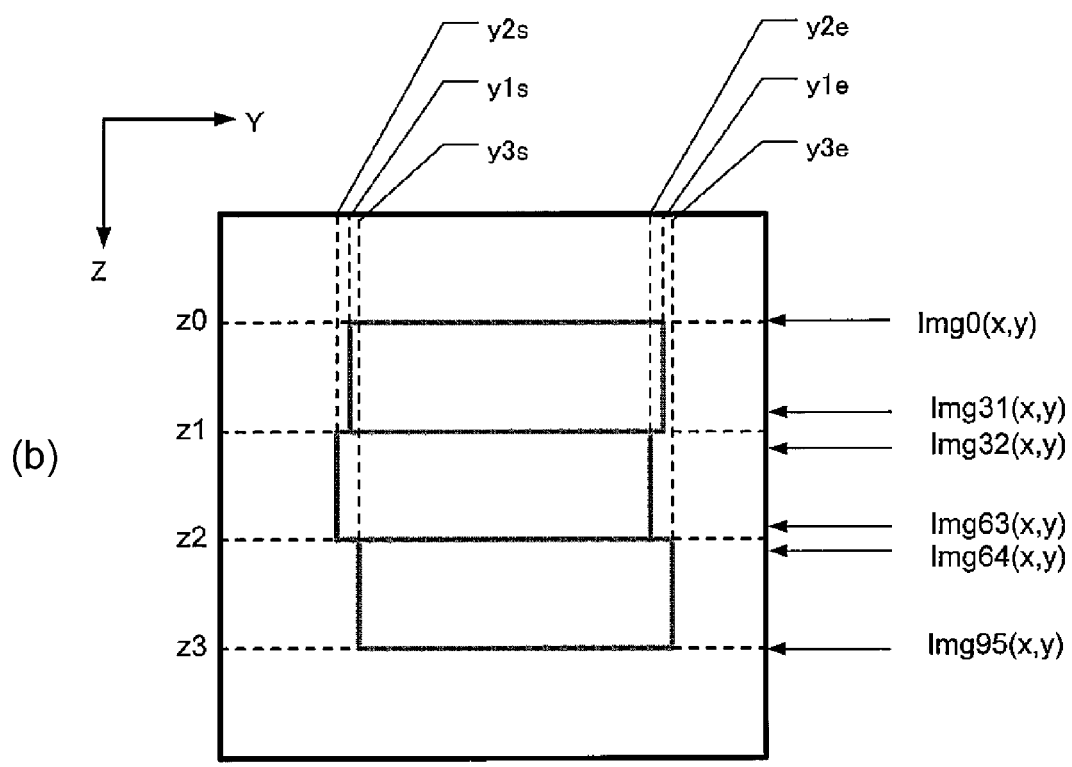

FIG. 22 is a diagram for describing a position correction for eliminating a displacement between tomographic images at a z-direction boundary, wherein FIG. 22(a) is a diagram showing an xz-plane MPR image thereof, and FIG. 22(b) is a diagram showing a yz-plane MPR image.

As shown in FIGS. 22(a) and 22(b) by way of example, the number of tomographic images each photographed by a conventional scan or cine scan at a z-direction coordinate position is 32. They are assumed to be Img0(x, y) through Img31(x, y). The number of tomographic images each photographed by a conventional scan or cine scan at a second z-direction coordinate position is also 32. They are assumed to be Img32(x, y) through Img63(x, y). The number of tomographic images each photographed by a conventional scan or cine scan at a third z-direction coordinate position is also 32. They are assumed to be Img64(x, y) through Img95(x, y).

In this case, in order to align a tomographic image at a first conventional scan or cine scan with a tomographic image at a second conventional scan or cine scan, the tomographic image Img31 at a boundary portion under the first conventional scan or cine scan and the tomographic image Img32 at a boundary portion under the second conventional scan or cine scan are brought into alignment with each other. In order to align the tomographic image at the second conventional scan or cine scan with the tomographic image at the third conventional scan or cine scan, the tomographic image Img63 at a boundary portion under the second conventional scan or cine scan, and the tomographic image Img64 at a boundary portion under the third conventional scan or cine scan may be aligned with each other. A method using each MPR image to perform this alignment will next be shown.

At an MPR image at y=yc1 particularly within MPR images in an xz plane as shown in FIG. 22(a), an x coordinate of a subject's boundary at the tomographic image Img31(x, y) is assumed to be x1s and x1e. When an x coordinate of a subject's boundary at the tomographic image Img32(x, y) is defined as x2s and x2e, the tomographic image Img32(x, y), and the tomographic image taken by the conventional scan or cine scan at the second z-direction coordinate position are shifted or displaced by the following (Equation 17) in the x direction.

Equation 17 (17)

$$\frac{x1s + x1e}{2} - \frac{x2s + x2e}{2}$$

At an MPR image at y=yc2 particularly within the MPR images in an xz plane as shown in FIG. 22(a) in like manner, an x coordinate of a subject's boundary at the tomographic image Img63(x, y) is assumed to be x2s and x2e. When an x coordinate of a subject's boundary at the tomographic image Img64(x, y) is defined as x3s and x3e, the tomographic image Img64(x, y), and the tomographic image taken by the conventional scan or cine scan at the third z-direction coordinate position are shifted by the following (Equation 18) in the x direction.

Equation 18 (18)

$$\frac{x1s + x1e}{2} - \frac{x2s + x2e}{2} + \frac{x2s + x2e}{2} - \frac{x3s + x3e}{2} =$$

$$\frac{x1s + x1e}{2} - \frac{x3s + x3e}{2}$$

At an MPR image at x=xc1 particularly within the MPR images in a yz plane as shown in FIG. 22(b) in like manner, a y coordinate of a subject's boundary at the tomographic image Img31(x, y) is assumed to be y1s and y1e. When a y coordinate of a subject's boundary at the tomographic image Img32(x, y) is defined as y2s and y2c, the tomographic image Img32(x, y), and the tomographic image taken by the conventional scan or cine scan at the second z-direction coordinate position are displaced by the following (Equation 19) in the y direction.

Equation 19 (19)

$$\frac{y1s + y1e}{2} - \frac{y2s + y2e}{2}$$

At an MPR image at x=xc2 particularly within the MPR images in the yz plane as shown in FIG. 22(b) in like manner, a y coordinate of a subject's boundary at the tomographic image Img63(x, y) is assumed to be y2s and y2e. When a y coordinate of a subject's boundary at the tomographic image Img64(x, y) is defined as y3s and y3e, the tomographic image Img64(x, y), and the tomographic image taken by the conventional scan or cine scan at the third z-direction coordinate position are displaced by the following (Equation 20) in the y direction.

Equation 20 (20)

$$\frac{y1s + y1e}{2} - \frac{y2s + y2e}{2} + \frac{y2s + y2e}{2} - \frac{y3s + y3e}{2} = \frac{y1s + y1e}{2} - \frac{y3s + y3e}{2}$$

Thus, the positions in the xy plane, of the tomographic images taken by the conventional scans or cine scans at the second and third z-direction coordinate positions can be subjected to the position displacement correction in accordance with the position in the xy plane, of each tomographic image taken by the conventional scan or cine scan at the first z-direction coordinate position.

Figure 23:
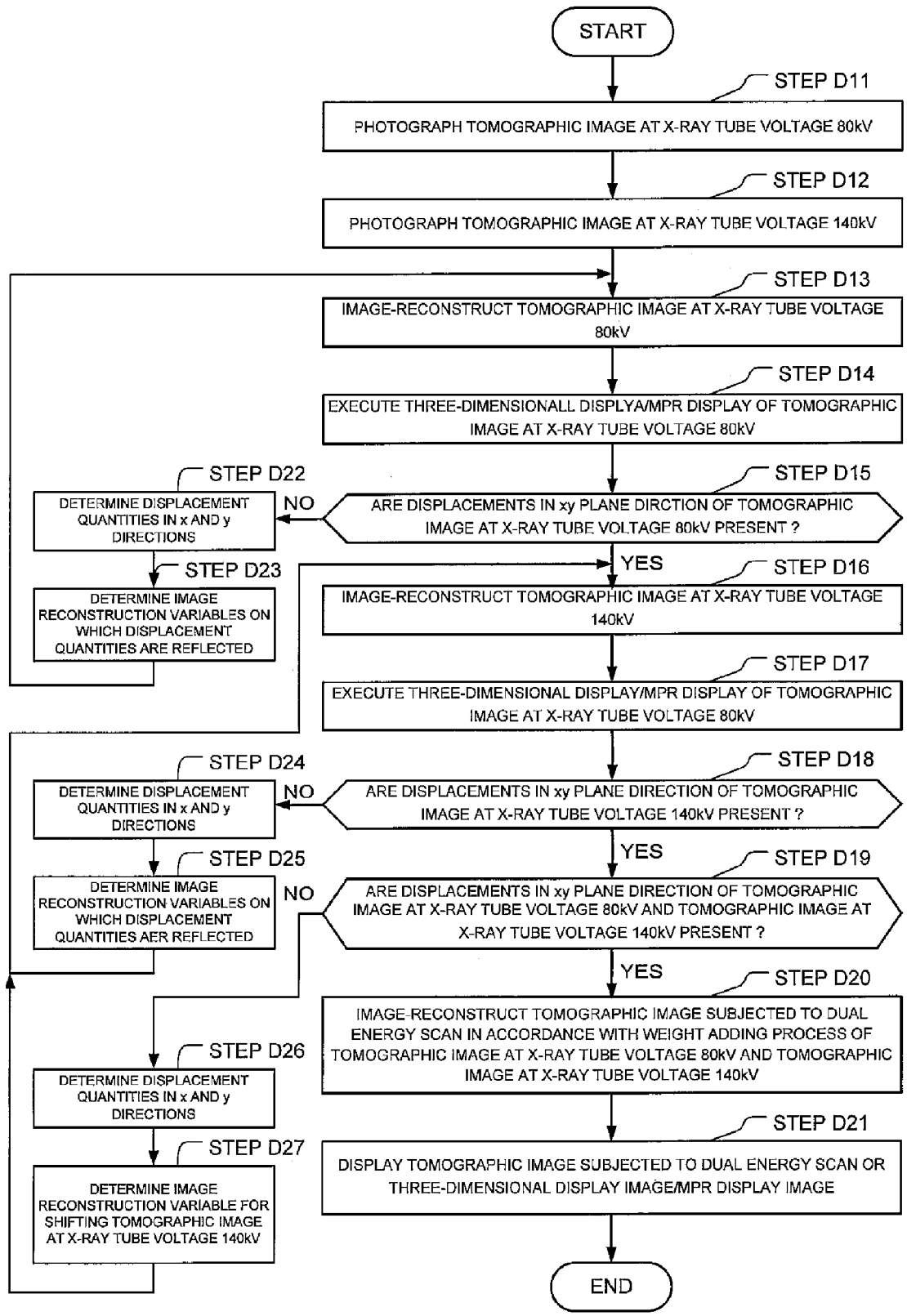
FIG. 23 is a flowchart for describing a process of a dual energy scan at which displacements in xy plane are corrected.

FIG. 23 is a flowchart showing a process of a dual energy scan which has corrected displacements in the xy plane.

At Step D11, a tomographic image at an X-ray tube voltage 80 kV is imaged or photographed.

At Step D12, a tomographic image at an X-ray tube voltage 140 kV is imaged or photographed.

At Step D13, the tomographic image at the X-ray tube voltage 80 kV is image-reconstructed.

At Step D14, the tomographic image at the X-ray tube voltage 80 kV is three-dimensionally displayed/MPR displayed.

At Step D15, it is determined whether displacements in an xy plane direction, of the tomographic image at the X-ray tube voltage 80 kV exist. If the answer is found to be YES, then the flowchart proceeds to Step D16. If the answer is found to be NO, then the flowchart proceeds to Step D22.

At Step D16, the tomographic image at the X-ray tube voltage 140 kV is image-reconstructed.

At Step D17, the tomographic image at the X-ray tube voltage 140 kV is three-dimensionally displayed/MPR displayed.

At Step D18, it is determined whether displacements in the xy plane direction, of the tomographic image at the X-ray tube voltage 140 kV exist. If the answer is found to be YES, then the flowchart proceeds to Step D19. If the answer is found to be NO, then the flowchart proceeds to Step D24.

At Step D19, it is determined whether displacements in the xy plane direction, of the tomographic image at the X-ray tube voltage 80 kV and the tomographic image at the X-ray tube voltage 140 kV exist. If the answer is found to be YES, then the flowchart proceeds to Step D20. If the answer is found to be NO, then the flowchart proceeds to Step D26.

At Step D20, each tomographic image at the dual energy scan is image-reconstructed in accordance with a weight adding process of the tomographic image at the X-ray tube voltage 80 kV and the tomographic image at the X-ray tube voltage 140 kV.

At Step D21, the tomographic image at the dual energy scan or a three-dimensional display image/MPR display image is displayed.

At Step D22, displacement quantities in xy directions are determined.

At Step D23, image reconstruction variables on which the displacement quantities are reflected, are determined, and the flowchart returns to Step D13.

At Step D24, displacement quantities in the xy directions are determined.

At Step D25, image reconstruction variables on which the displacement quantities are reflected, are determined, and the flowchart returns to Step D16.

At Step D26, displacement quantities in the xy directions are determined.

At Step D27, an image reconstruction variable for shifting or displacing the tomographic image at the X-ray tube voltage 140 kV is determined, and the flowchart returns to Step D16.

At Steps D15, 18 and 19, it is checked in accordance with the above processing whether there are displacements in the xy plane, of the tomographic images. The displacement quantities in the xy directions are determined at Steps D22, D24 and D26 as described above.

The position displacement or mis-registration correction may be performed by shifting these displacement quantities by changes in the image reconstruction variables for image reconstruction processing as in the case of Steps D23, D25 and D27. Alternatively, a position shifting or displacement process based on a tomographic image plane may be performed.

In the above X-ray CT apparatus 100, according to the X-ray CT apparatus of the present invention or the X-ray CT image reconstructing method, it produces the effect of being capable of realizing an X-ray CT apparatus which optimizes spatial resolution of each tomographic image subjected to the dual energy scan and the image noise thereof. Incidentally, weighted addition coefficients for a weight adding process are determined by X-ray absorption coefficients at a plurality of X-ray tube voltages, of atoms depending on atoms desired to be emphasized and atoms desired to be eliminated, even in the case of any image reconstructing method.

Although 80 kV is used as the low X-ray tube voltage and 140 kV is used as the high X-ray tube voltage in the above embodiment, a similar effect can be produced even at other X-ray tube voltages. Although the calcium such as the bone or the calcified portion, and iodine contained in the contrast agent are used as the atoms desired to be extracted or the atoms desired to be emphasized in the present embodiment, a similar effect can be brought about even when other atoms are extracted or emphasized. Incidentally, the image reconstructing method employed in the present embodiment may be a three-dimensional image reconstructing method based on the conventionally known Feldkamp method. Further, another three-dimensional image reconstructing method may be used. Alternatively, two-dimensional image reconstruction may be adopted.

Although the above embodiment has described the case in which the X-ray autoexposure mechanism for the X-ray CT apparatus is not used, a similar effect can be brought about even where the X-ray autoexposure mechanism of the X-ray CT apparatus is used. That is, geometrical characteristic values such as profile areas and ellipticity or the like of a subject at respective z-direction coordinate positions are determined from the scout image. X-ray tube currents at the z-direction coordinate positions are adjusted depending on changes in the profile areas and ellipticity or the like in the z direction thereof, thereby allowing image noise of tomographic images at the z-direction coordinate positions to be held constant. Image noise index values targeted for an X-ray tube voltage 80 kV and an X-ray tube voltage 140 kV are defined corresponding to each tomographic image at the X-ray tube voltage 80 kV and each tomographic image at the X-ray tube voltage 140 kV, whereby the tomographic image at the X-ray tube voltage 80 kV and the tomographic image at the X-ray tube voltage 140 kV are also brought to constant image noise at the respective z-direction coordinate positions. Therefore, each tomographic image subjected to a dual energy scan, which is image-reconstructed by a weight adding process of the tomographic image at the X-ray tube voltage 80 kV and the tomographic image at the X-ray tube voltage 140 kV, can be also brought to constant image noise in the z direction.

Although the above embodiment has described the case in which the scan gantry 20 is not tilted, a similar effect can be brought about even in the case of a so-called tilt-scan in which the scan gantry 20 is tilted. Although the present embodiment has also described the case in which X-ray data acquisition is not synchronized with a biological signal, a similar effect can be brought about even though the X-ray data acquisition is synchronized with the biological signal, particularly, a cardiac signal.

Although the above embodiment has described the X-ray CT apparatus having the two-dimensional X-ray area detector, a similar effect can be brought about even in the case of an X-ray CT apparatus having a row of X-ray detectors. Incidentally, in the present embodiment, the helical scan, variable pitch helical scan and helical shuttle scan are realized by moving the cradle 12 of the photographing table 10 in the z direction. Shifting between the respective z-direction scan positions of the conventional scan or the cine scan is realized. However, a similar effect can be obtained relatively even by moving the scan gantry 20 or the rotating section 15 lying in the scan gantry 20 relative to the cradle 12 of the photographing table 10.

In the above embodiment, coefficients of row-direction (z-direction) filters different in coefficient every row are convolved in a row direction of pre-processed or beam hardening-corrected X-ray projection data for respective channels to adjust variations in image quality, thereby providing a uniform slice thickness at each row, suppressing artifacts and realizing noise-reduced image quality. While various z-direction filter coefficients are considered therefor, a similar effect can be brought about in any case.

Although the present embodiment has been described on the basis of the medical X-ray CT apparatus, it can be made available to an X-ray CT-PET apparatus utilized in combination with an industrial X-ray CT apparatus or another apparatus, an X-ray CT-SPECT apparatus utilized in combination therewith, etc.

The invention claimed is:

1. An X-ray CT apparatus comprising:
    an X-ray tube for applying, to a subject, X rays having a first energy spectrum and X rays having a second energy spectrum different from the first energy spectrum;
    an X-ray data acquisition unit for acquiring X-ray projection data of the first energy spectrum applied to the subject and X-ray projection data of the second energy spectrum applied thereto;
    a dual energy image reconstructing unit for reconstructing tomographic images indicative of X-ray tube voltage-dependent information at X-ray absorption coefficients related to a distribution of atoms based on the X-ray projection data of the first energy spectrum and the X-ray projection data of the second energy spectrum; and
    an adjusting unit for adjusting conditions related to the X-ray projection data of the first energy spectrum and for adjusting conditions related to the X-ray projection data of the second energy spectrum such that noise of the X-ray projection data of the first energy spectrum and noise of the X-ray projection data of the second energy spectrum are made approximately equal to each other.

2. The X-ray CT apparatus according to claim 1, wherein the dual energy image reconstructing unit reconstructs a first tomographic image and a second tomographic image based on the X-ray projection data of the first energy spectrum and the X-ray projection data of the second energy spectrum, and reconstructs the tomographic images indicative of the X-ray tube voltage-dependent information at the X-ray absorption coefficients related to the distribution of the atoms based on the first tomographic image and the second tomographic image, and wherein the adjusting unit includes adjusting image reconstruction conditions for the first and second tomographic images respectively to optimize the tomographic images indicative of the X-ray tube voltage-dependent information.

3. The X-ray CT apparatus according to claim 2, wherein the adjusting unit adjusts imaging conditions at an application of the X rays having the first energy spectrum and the X rays having the second energy spectrum in order to optimize the tomographic images indicative of the X-ray tube voltage-dependent information.

4. The X-ray CT apparatus according to claim 1, wherein image reconstruction conditions are adjusted while being allowed to depend upon index values for image quality of the tomographic images indicative of the X-ray tube voltage-dependent information by the dual energy image reconstructing unit.

5. The X-ray CT apparatus according to claim 2, wherein image reconstruction conditions are adjusted while being allowed to depend upon index values for image quality of the tomographic images indicative of the X-ray tube voltage-dependent information by the dual energy image reconstructing unit.

6. The X-ray CT apparatus according to claim 3, wherein image reconstruction conditions are adjusted while being allowed to depend upon index values for image quality of the tomographic images indicative of the X-ray tube voltage-dependent information by the dual energy image reconstructing unit.

7. The X-ray CT apparatus according to claim 1, wherein the X-ray tube applies the X rays having the first energy spectrum and the X rays having the second energy spectrum to a same region of the subject.

8. The X-ray CT apparatus according to claim 2, wherein the X-ray tube applies the X rays having the first energy spectrum and the X rays having the second energy spectrum to a same region of the subject.

9. The X-ray CT apparatus according to claim 1, wherein the dual energy image reconstructing unit reconstructs X-ray projection data obtained by multiplying the X-ray projection data of the first energy spectrum by a first weighted coefficient, multiplying the X-ray projection data of the second energy spectrum by a second weighted coefficient corresponding to a minus number, and subjecting the reconstructed X-ray projection data and the multiplied X-ray projection data to a weight adding process.

10. The X-ray CT apparatus according to claim 2, wherein the dual energy image reconstructing unit multiplies the first tomographic image by a first weighted coefficient, multiplies the second tomographic image by a second weighted coefficient corresponding to a minus number and subjects the multiplied first tomographic image and the multiplied second tomographic image to a weight adding process.

11. The X-ray CT apparatus according to claim 1, wherein the image reconstruction uses at least one of an image reconstruction function, an image filter, an image reconstruction matrix number, a z filter, and a space filter for an X-ray projection data space.

12. The X-ray CT apparatus according to claim 4, wherein the index values for image quality have at least one of a noise index value, a spatial resolution index value, or a slice thickness index value.

13. The X-ray CT apparatus according to claim 1, wherein noise of the X-ray projection data of the first energy spectrum and noise of the X-ray projection data of the second energy spectrum are made approximately equal to each other to isolate iodine by eliminating certain tissue components.

14. The X-ray CT apparatus according to claim 2, wherein image noise of the first tomographic image and image noise of the second tomographic image are made approximately equal to each other, or made approximately equal to each other when weighted addition coefficients are multiplied.

15. The X-ray CT apparatus according to claim 10, wherein image noise of the first tomographic image and image noise of the second tomographic image are made approximately equal to each other, or made approximately equal to each other when weighted addition coefficients are multiplied.

16. The X-ray CT apparatus according to claim 1, wherein when mis-registration artifacts are observed at the tomographic images indicative of the X-ray tube voltage-dependent information, the first tomographic image and the second tomographic image are aligned with each other for additional image reconstruction.

17. The X-ray CT apparatus according to claim 1, wherein when displacements occur in a tomographic image plane when one of a display in the direction of a body axis of the subject is effected or a three-dimensional display is effected on the tomographic images indicative of the X-ray tube voltage-dependent information, the first tomographic image and the second tomographic image are aligned with each other for additional image reconstruction.

18. A method of assembling an X-ray CT apparatus, said method comprising:

providing an X-ray tube configured to apply, to a subject, X rays having a first energy spectrum and X rays having a second energy spectrum different from the first energy spectrum;

providing an X-ray data acquisition unit configured to acquire X-ray projection data of the first energy spectrum applied to the subject and X-ray projection data of the second energy spectrum applied thereto;

providing a dual energy image reconstructing unit configured to reconstruct tomographic images indicative of X-ray tube voltage-dependent information at X-ray absorption coefficients related to a distribution of atoms based on the X-ray projection data of the first energy spectrum and the X-ray projection data of the second energy spectrum; and providing an adjusting unit configured to adjust conditions related to the X-ray projection data of the first energy spectrum and for adjusting conditions related to the X-ray projection data of the second energy spectrum such that noise of the X-ray projection data of the first energy spectrum and noise of the X-ray projection data of the second energy spectrum are made approximately equal to each other.

19. A method of assembling an X-ray CT apparatus according to claim 18, wherein:

providing a dual energy image reconstructing unit further comprises providing a dual energy image reconstructing unit configured to:
reconstruct a first tomographic image and a second tomographic image based on the X-ray projection data of the first energy spectrum and the X-ray projection data of the second energy spectrum; and
reconstruct the tomographic images indicative of the X-ray tube voltage-dependent information at the X-ray absorption coefficients related to the distribution of the atoms based on the first tomographic image and the second tomographic image and,
wherein providing an adjusting unit further comprises providing an adjusting unit configured to adjust image reconstruction conditions for the first and second tomographic images, respectively, to optimize the tomographic images indicative of the X-ray tube voltage-dependent information.

* * * * *